US012616745B2

(12) United States Patent
Hatta et al.

(10) Patent No.: US 12,616,745 B2
(45) Date of Patent: May 5, 2026

(54) INFLUENZA VIRUS BACKBONE

(71) Applicant: FLUGEN, INC., Madison, WI (US)

(72) Inventors: Yasuko Hatta, Madison, WI (US); Michael J. Moser, Madison, WI (US); Pamuk Bilsel, Madison, WI (US)

(73) Assignee: FLUGEN, INC., Madison, WI (US)

( * ) Notice: Subject to any disclaimer, the term of this patent is extended or adjusted under 35 U.S.C. 154(b) by 836 days.

(21) Appl. No.: 17/617,258

(22) PCT Filed: Jun. 5, 2020

(86) PCT No.: PCT/US2020/036455
§ 371 (c)(1),
(2) Date: Dec. 7, 2021

(87) PCT Pub. No.: WO2020/247844
PCT Pub. Date: Dec. 10, 2020

(65) Prior Publication Data
US 2022/0241397 A1 Aug. 4, 2022

Related U.S. Application Data

(60) Provisional application No. 62/858,737, filed on Jun. 7, 2019.

(51) Int. Cl.
*A61K 39/145* (2006.01)
*A61P 31/16* (2006.01)
*C12N 7/00* (2006.01)
*A61K 39/00* (2006.01)

(52) U.S. Cl.
CPC ............ *A61K 39/145* (2013.01); *A61P 31/16* (2018.01); *C12N 7/00* (2013.01); *A61K 2039/5254* (2013.01); *A61K 2039/543* (2013.01); *A61K 2039/545* (2013.01); *A61K 2039/58* (2013.01); *A61K 2039/70* (2013.01)

(58) Field of Classification Search
CPC .............. A61K 39/145; A61K 2039/70; A61K 2039/5254; A61K 39/12; A61P 31/16; C12N 2760/16152
See application file for complete search history.

(56) References Cited

U.S. PATENT DOCUMENTS

| | | | |
|---|---|---|---|
| 6,270,958 B1 | 8/2001 | Olivo et al. | |
| 6,544,785 B1 | 4/2003 | Palese et al. | |
| 6,872,395 B2 | 3/2005 | Kawaoka | |
| 7,176,021 B2 | 2/2007 | Kawaoka | |
| 7,226,774 B2 | 6/2007 | Kawaoka | |
| 7,276,356 B1 | 10/2007 | Palese et al. | |
| 7,312,064 B2 | 12/2007 | Hoffmann | |
| 7,384,774 B2 | 6/2008 | Palese et al. | |
| 7,459,162 B2 | 12/2008 | Yang et al. | |
| 7,510,719 B2 | 3/2009 | Dang et al. | |
| 7,566,458 B2 | 7/2009 | Yang et al. | |
| 7,585,657 B2 | 9/2009 | Kawaoka | |
| 7,588,769 B2 | 9/2009 | Kawaoka | |
| 7,723,094 B2 | 5/2010 | Kawaoka et al. | |
| 7,790,434 B2 | 9/2010 | Duke et al. | |
| 7,959,930 B2 | 6/2011 | De Wit et al. | |
| 7,968,101 B2 | 6/2011 | Kawaoka et al. | |
| 7,972,843 B2 | 7/2011 | Hoffmann | |
| 7,993,924 B2 | 8/2011 | Billeter et al. | |
| 8,012,736 B2 | 9/2011 | Hoffman et al. | |
| 8,012,737 B2 | 9/2011 | Dang et al. | |
| 8,043,856 B2 | 10/2011 | Kawaoka et al. | |
| 8,048,430 B2 | 11/2011 | Yang et al. | |
| 8,057,806 B2 | 11/2011 | Kawaoka | |
| 8,163,523 B2 | 4/2012 | Bilsel et al. | |
| 8,202,726 B2 | 6/2012 | Liu et al. | |
| 8,288,145 B2 | 10/2012 | Röthl et al. | |
| 8,298,805 B2 | 10/2012 | Kawaoka | |
| 8,333,975 B2 | 12/2012 | Yang et al. | |
| 8,404,248 B2 | 3/2013 | Yang et al. | |
| 8,465,960 B2 | 6/2013 | Kawaoka et al. | |
| 8,475,806 B2 | 7/2013 | Kawaoka et al. | |
| 8,507,247 B2 | 8/2013 | Kawaoka et al. | |

(Continued)

FOREIGN PATENT DOCUMENTS

| | | |
|---|---|---|
| CN | 102864127 A | 1/2013 |
| CN | 102864128 A | 1/2013 |

(Continued)

OTHER PUBLICATIONS

U.S. Patent and Trademark Office, International Search Report for International Patent Application PCT/US2020/036455 (Sep. 30, 2020).
U.S. Appl. No. 18/017,371, filed Jan. 20, 2023.
U.S. Appl. No. 18/017,374, filed Jan. 20, 2023.
Ping et al., "Development of high-yield influenza A virus vaccine viruses," *Nat. Commun.*, 6: 8148 (2015).
Watanabe et al., "Influenza A Virus Lacking M2 Protein as a Live Attenuated Vaccine," *Journal of Virology*, 83(11): 5947-5950 (2009).

(Continued)

*Primary Examiner* — Bao Q Li

(74) *Attorney, Agent, or Firm* — LEYDIG, VOIT & MAYER, LTD.

(57) ABSTRACT

The invention provides an influenza virus that demonstrates enhanced growth in Vero cells. The influenza virus includes PB1, PB2, PA, NP, and NS gene segments encoding proteins having amino acid sequences with selected amino acids. Optionally, at least one of the PB1, PB2, and PA gene segments includes a cytosine to uracil promoter mutation at nucleotide position 4. The invention also provides a pharmaceutical formulation containing the influenza virus, as well as a method of eliciting an immune response in a mammal by administering the influenza virus to the mammal, and a method for generating the influenza virus.

33 Claims, 29 Drawing Sheets
Specification includes a Sequence Listing.

(56)  References Cited

U.S. PATENT DOCUMENTS

| | | | |
|---|---|---|---|
| 8,574,593 B2 | 11/2013 | Yang et al. | |
| 8,592,196 B2 | 11/2013 | Kittel et al. | |
| 8,597,661 B2 | 12/2013 | Kawaoka et al. | |
| 8,673,613 B2 | 3/2014 | Jin et al. | |
| 8,679,819 B2 | 3/2014 | Kawaoka | |
| 8,685,410 B2 | 4/2014 | Yang et al. | |
| 8,691,239 B2 | 4/2014 | Yang et al. | |
| 8,715,940 B2 | 5/2014 | Kawaoka et al. | |
| 8,859,208 B2 | 10/2014 | Kawaoka et al. | |
| 8,877,209 B2 | 11/2014 | Kawaoka et al. | |
| 8,877,210 B2 | 11/2014 | Yang et al. | |
| 8,877,448 B2 | 11/2014 | Kawaoka et al. | |
| 8,883,479 B2 | 11/2014 | Krenn et al. | |
| 9,023,603 B2 | 5/2015 | Kawaoka et al. | |
| 9,068,986 B2 | 6/2015 | Jin et al. | |
| 9,085,753 B2 | 7/2015 | Liu et al. | |
| 9,101,653 B2 | 8/2015 | Kawaoka et al. | |
| 9,109,013 B2 | 8/2015 | Kawaoka et al. | |
| 9,119,810 B2 | 9/2015 | Montelione et al. | |
| 9,157,096 B2 | 10/2015 | Kawaoka et al. | |
| 9,254,318 B2 | 2/2016 | Kawaoka et al. | |
| 9,284,533 B2 | 3/2016 | Bilsel et al. | |
| 9,474,798 B2 | 10/2016 | Watanabe et al. | |
| 9,580,693 B2 | 2/2017 | Kawaoka et al. | |
| 9,732,313 B2 | 8/2017 | Hirschel et al. | |
| 9,757,446 B2 | 9/2017 | LeFebvre et al. | |
| 9,890,363 B2 | 2/2018 | Kawaoka et al. | |
| 9,919,042 B2 | 3/2018 | Bilsel et al. | |
| 9,919,043 B2 | 3/2018 | Bilsel et al. | |
| 9,926,535 B2 | 3/2018 | Kawaoka et al. | |
| 9,950,057 B2 * | 4/2018 | Kawaoka | A61K 39/145 |
| 10,022,434 B2 | 7/2018 | Weiner et al. | |
| 10,053,671 B2 | 8/2018 | Kawaoka et al. | |
| 10,059,925 B2 | 8/2018 | Kawaoka et al. | |
| 10,119,124 B2 | 11/2018 | Watanabe et al. | |
| 10,130,697 B2 | 11/2018 | Watanabe et al. | |
| 10,172,934 B2 | 1/2019 | Kawaoka et al. | |
| 10,246,686 B2 | 4/2019 | Kawaoka et al. | |
| 10,358,630 B2 | 7/2019 | Kawaoka et al. | |
| 10,494,613 B2 | 12/2019 | Kawaoka et al. | |
| 10,500,267 B2 | 12/2019 | LeFebvre et al. | |
| 10,513,692 B2 | 12/2019 | Kawaoka et al. | |
| 10,570,376 B2 | 2/2020 | Peterka et al. | |
| 10,633,422 B2 | 4/2020 | Kawaoka et al. | |
| 10,808,229 B2 | 10/2020 | Kawaoka et al. | |
| 11,007,262 B2 | 5/2021 | Watanabe et al. | |
| 11,046,934 B2 | 6/2021 | Kawaoka et al. | |
| 11,180,737 B2 | 11/2021 | Kawaoka et al. | |
| 11,197,925 B2 | 12/2021 | Kawaoka et al. | |
| 2003/0035814 A1 | 2/2003 | Kawaoka et al. | |
| 2004/0180058 A1 | 9/2004 | Shneider et al. | |
| 2009/0246830 A1 | 10/2009 | Kawaoka et al. | |
| 2011/0300604 A1 | 12/2011 | Kawaoka et al. | |
| 2013/0115242 A1 | 5/2013 | Moules et al. | |
| 2013/0243804 A1 | 9/2013 | Stoloff et al. | |
| 2015/0017205 A1 | 1/2015 | Kawaoka et al. | |
| 2015/0166967 A1 | 6/2015 | Kawaoka et al. | |
| 2015/0368621 A1 | 12/2015 | Kawaoka et al. | |
| 2016/0002606 A1 | 1/2016 | Peterka et al. | |
| 2016/0284020 A1 | 9/2016 | Williams | |
| 2017/0198264 A1 | 7/2017 | Kawaoka et al. | |
| 2017/0216425 A1 | 8/2017 | Ahmed et al. | |
| 2017/0258888 A1 | 9/2017 | Kawaoka et al. | |
| 2017/0354730 A1 | 12/2017 | Kawaoka et al. | |
| 2018/0340152 A1 | 11/2018 | Kawaoka et al. | |
| 2019/0048324 A1 | 2/2019 | Kawaoka et al. | |
| 2019/0060441 A1 | 2/2019 | Bilsel et al. | |
| 2019/0167781 A1 | 6/2019 | Kawaoka et al. | |
| 2019/0184007 A1 | 6/2019 | Ahmed et al. | |
| 2020/0061182 A1 | 2/2020 | Bilsel et al. | |
| 2020/0188506 A1 | 6/2020 | Kawaoka et al. | |
| 2020/0263143 A1 | 8/2020 | Kawaoka et al. | |
| 2023/0256086 A1 | 8/2023 | Moser et al. | |
| 2023/0295582 A1 | 9/2023 | Moser et al. | |

FOREIGN PATENT DOCUMENTS

| | | | |
|---|---|---|---|
| CN | 102864129 A | 1/2013 | |
| WO | 2005115448 A2 | 12/2005 | |
| WO | 2006083286 A2 | 8/2006 | |
| WO | WO 2010/117786 A1 | 10/2010 | |
| WO | 2011014504 A1 | 2/2011 | |
| WO | 2015063085 A1 | 5/2015 | |
| WO | 2015142671 A2 | 9/2015 | |
| WO | WO 2017/007839 A1 | 1/2017 | |
| WO | 2017184626 A1 | 10/2017 | |
| WO | WO 2018/157028 A1 | 8/2018 | |
| WO | WO 2018/157047 A1 | 8/2018 | |
| WO | WO 2022/020460 A1 | 1/2022 | |
| WO | WO 2022/020469 A1 | 1/2022 | |

OTHER PUBLICATIONS

Clark, et al.,"Functional Evolution of Influenza Virus NS1 Protein in Currently Circulating Human 2009 Pandemic H1N1 Viruses," *Journal of Virology*, 91(17): 1-22 (Aug. 10, 2017).

Davis et al., "Identification of influenza A nucleoprotein body domain residues essential for viral RNA expression expose antiviral target," *Virology Journal*, 14(22): 1-13 (Feb. 7, 2017).

Globaldata Healthcare, "Influenza vaccine: FluGen has successful Phase II trial for M2SR," Feb. 22, 2019, XP093027811, Retrieved from the Internet Mar. 1, 2023 https://www.pharmaceutical-technology.com/comment/flugen-successbrings-the-reality-of-universal-influenza-vaccines-closer/.

Hatta et al., "M2SR, a novel live influenza vaccine, protects mice and ferrets against highly pathogenic avian influenza," *Vaccine* 35(33): 4177-4183 (2017).

Hu et al., "A Vero-cell-adapted vaccine donor strain of influenza A virus generated by serial passages," *Vaccine* 33(2): 374-381 (2014).

Liedmann et al., "Viral suppressors of the RIG-I-mediated inter-feron responses are pre-packaged in influenza virions," *Nature Communications*, 5(5645): 1-8 (Dec. 9, 2014).

Yamaji et al., "Mammalian Adaptive Mutations of the PA Protein of Highly Pathogenic Avian H5N1 Influenza Virus," *Journal of Virology*, 89(8): 4117-4133 (Jan. 28, 2015).

European Patent Office, Extended European Search Report in European Patent Application No. 20 818 294.9 (Mar. 13, 2023).

U.S. Patent and Trademark Office, International Search Report in International Patent Application No. PCT/US2021/042561 (Dec. 21, 2021).

U.S. Patent and Trademark Office, Written Opinion in International Patent Application No. PCT/US2021/042561 (Dec. 21, 2021).

U.S. Patent and Trademark Office, International Search Report in International Patent Application No. PCT/US2021/042572 (Nov. 10, 2021).

U.S. Patent and Trademark Office, Written Opinion in International Patent Application No. PCT/US2021/042572 (Nov. 10, 2021).

Furusawa et al., "Influenza Virus Polymerase Mutation Stabilizes a Foreign Gene Inserted into the Virus Genome by Enhancing the Transcription/Replication Efficiency of the Modified Segment," mBio 10(5): e01794-19 (2019).

Heaton et al., "In Vivo Bioluminescent Imaging of Influenza A Virus Infection and Characterization of Novel Cross- Protective Mono-clonal Antibodies," Journal of Virology, 87(15): 8272-8281 (2013).

Hoffmann et al., "Universal primer set for the full-length amplification of all influenza A viruses," Arch. Virol., 146: 2275-2289 (2001).

Jin et al., "Multiple amino acid residues confer temperature sensitivity to human influenza virus vaccine strains (FluMist) derived from cold-adapted A/Ann Arbor/6/60," Virology, 306: 18-24 (2003).

Manicassamy et al., "Analysis of in vivo dynamics of influenza virus infection in mice using a GFP reporter virus," PNAS, 107(25): 11531-11536 (2010).

Nogales et al., "A Novel Fluorescent and Bioluminescent Bireporter Influenza A Virus To Evaluate Viral Infections," Journal of Virology, 93(10): e00032-19 (2019).

Pan et al., "Development and application of bioluminescence imaging for the influenza A virus," J. Thorac. Dis., 10 (Suppl. 19): S2230-S2237 (2018).

(56) References Cited

OTHER PUBLICATIONS

Wang et al., "Generation of a Reassortant Influenza A Subtype H3N2 Virus Expressing Gaussia Luciferase," Viruses, 11(7): 665 (2019).
European Patent Office, Extended European Search Report in European Patent Application No. 21845261.3 (Sep. 30, 2024).
European Patent Office, Extended European Search Report in European Patent Application No. 21845413.0 (Oct. 14, 2024).
Japan Patent Office, Notice of Reasons for Refusal in Japanese Patent Application No. 504319-2023 (Jul. 29, 2025).

* cited by examiner

| | amino acid position with signal peptide (1-17 aa) | | | | | | | | | | | | |
|---|---|---|---|---|---|---|---|---|---|---|---|---|---|
| | | HA1 = 18-344 aa | | | | | | HA2 = 345-end aa | | | | | |
| Virus Name | aa 14 | aa 24 | aa 146 | aa 172 | aa 204 | aa 239 | aa 240 | aa 347 | aa 362 | aa 388 | aa 421 | aa 451 | aa 526 |
| 2013 Mass15 | gcc = A | Y | agc = S | G | D | D | cga = R | F | V | A | I | aat = N | R |
| 2015 MI45 | | Y | N | G | D | D | cga = R | F | tta = L | A | I | aat = N | R |
| 2015 Slovenia | | Y | N | G | D | D | cga = R | F | V | A | I | aat = N | aag = R or ggg = G |
| 2015 Lisboa | | cat = L | N | G | D | ggt = G | Q | F | V | A | gta = V | T | R |
| 2015 Scotland | | Y | N | G | D | D | cga = R | F | V | gcc = V | I | T | R |
| 2016 Montana 50 | | Y | N | gaa = E | gtc = V | D | Q | ttc = L | V | A | I | T | R |

FIG. 7A

Sing 2016 HA Mutations

| HA Name | Description | Sequence | HA1 (AA are full-length protein) | | | | | | HA2 (AA are full-length protein) | | | |
|---|---|---|---|---|---|---|---|---|---|---|---|---|
| | | | T216* | L210* | T319 | S221 | D241* | P243* | K467 | D435 | E339 | R472 |
| | | | T216K | L210P | T319I | S221P | D241G | P243H | K467E | D435N | E459K | R472G |
| Clinical | | Patient | C | T | C | T | A | C | A | G | G | A |
| V1 | Clin.+T216K, L210P | Egg P2/Vero P1 | A | C | C | T | A | C | A | G | G | A |
| V5 | V1-D241G | M2SR V1 P2 Round 1 HA | A | C | C | T | G | C | A | G | G | A |
| V1 | | M2SR V1 P3 Round 1 HA | A | C | C | T | A | C | A | G | G | A |
| V/5 R2 | | M2SR V1 P3 Round 2 HA | A | C | C | T | G | C | A | G | G | A |
| V2 | V1-D241G, D435N | Egg P2/Vero P1 | A | C | C | T | G | C | A | A | G | A |
| V6 | V2+P243H, K467E | M2SR V2 P2 Round 1 HA | A | C | T | T | G | H | E | A | G | G |
| V2 | V2+T319I, R472G | M2SR V2 P3 Round 1 HA | A | C | C | C | G | C | A | A | G | G |
| V8 | V2+K467E | M2SR V2 P3 Round 2 HA | A | C | G | T | A | C | A | A | G | A |
| V3 | Clin.+S221P, E459K | M2SR/Vero P4 | A | T | G | C | A | C | A | G | A | A |
| V4 | Clin.+E459K | M2SR/Vero P5 | C | T | G | T | A | C | A | G | A | A |

*Mutation may change glycosylation pattern

SEQUENCE LISTING

<160> NUMBER OF SEQ ID NOS: 20

<210> SEQ ID NO 1
<211> LENGTH: 1565
<212> TYPE: DNA
<213> ORGANISM: Influenza A virus
<220> FEATURE:
<221> NAME/KEY: misc_feature
<223> OTHER INFORMATION: NP gene segment (FGHY-1)

<400> SEQUENCE: 1

```
agcaaaagca gggtagataa tcactcactg agtgacatca aaatcatggc gtctcaaggc      60
accaaacgat cttacgaaca gatggagact gatggagaac gccagaatgc cactgaaatc     120
agagcatccg tcggaaaaat gattggtgga attggacgat tctacatcca aatgtgcacc     180
gaactcaaac tcagtgatta tgagggacgg ttgatccaaa acagcttaac aatagagaga     240
atggtgctct ctgcttttga cgaaaggaga aataaatacc ttgaagaaca tcccagtgcg     300
gggaaagatc ctaagaaaac tggaggacct atatacagga gagtaaacgg aaagtggatg     360
agagaactca tcctttatga caaagaagaa ttaaggcgaa tctggcgcca agctaataat     420
ggtgacgatg caacggctgg tctgactcac atgatgatct ggcattccaa tttgaatgat     480
gcaacttatc agaggacaag agctcttgtt cgcaccggaa tggatcccag gatgtgctct     540
ctgatgcaag gttcaactct ccctaggagg tctggagccg caggtgctgc agtcaaagga     600
```

-continued

```
gttggaacaa tggtgatgga attggtcaga atgatcaaac gtgggatcaa tgatcggaac      660
ttctggaggg gtgagaatgg acgaaaaaca agaattgctt atgaaagaat gtgcaacatt      720
ctcaaaggga aatttcaaac tgctgcacaa aaagcaatga tggatcaagt gagagagagc      780
cggaacccag ggaatgctga gttcgaagat ctcacttttc tagcacggtc tgcactcata      840
ttgagagggt cggttgctca caagtcctgc ctgcctgcct gtgtgtatgg acctgccgta      900
gccagtgggt acgactttga aaggaaggga tactctctag tcggaataga cccttttcaga      960 ctgcttcaaa acagccaagt gtacagccta atcagaccaa atgagaatcc agcacacaag     1020
agtcaactgg tgtggatggc atgccattct gccgcatttg aagatctaag agtattaagc     1080
ttcatcaaag ggacgaaggt gctcccaaga gggaagcttt ccactagagg agttcaaatt     1140
gcttccaatg aaaatatgga gactatggaa tcaagtacac ttgaactgag aagcaggtac     1200
tgggccataa ggaccagaag tggaggaaac accaatcaac agagggcatc tgcgggccaa     1260
atcagcatac aacctacgtt ctcagtacag agaaatctcc cttttgacag aacaaccatt     1320
atggcagcat tcaatgggaa tacagagggg agaacatctg acatgaggac cgaaatcata     1380
aggatgatgg aaagtgcaag accagaagat gtgtctttcc aggggcgggg agtcttcgag     1440
ctctcggacg aaaaggcagc gagcccgatc gtgccttcct ttgacatgag taatgaagga     1500
tcttatttct tcggagacaa tgcagaggag tacgacaatt aaagaaaaat acccttgttt     1560
ctact                                                                  1565
```

<210> SEQ ID NO 2
<211> LENGTH: 2341
<212> TYPE: DNA
<213> ORGANISM: Influenza A virus
<220> FEATURE:
<221> NAME/KEY: misc_feature
<223> OTHER INFORMATION: PB1 gene segment (FGHY-1)

<400> SEQUENCE: 2

```
agcaaaagca ggcaaaccat ttgaatggat gtcaatccga ccttacttt cttaaaagtg       60 ccagcacaaa atgctataag cacaactttc ccttatactg gagatcctcc ttacagccat      120
gggacaggaa caggatacac cttggatact gtcaacagga cacatcagta ctcagaaaag      180
ggaagatgga caacaaacac cgaaactgga gcaccgcaac tcaacccgat tgatgggcca      240
ctgccagaag acaatgaacc aagtggttat gcccaaacag attgtgtatt ggaggcgatg      300
gctttccttg aggaatccca tcctggtatt tttgaaaact cgtgtattga acgatggag       360 gttgttcagc aaacacgagt agacaagctg acacaaggcc gacagaccta tgactggact      420
ctaaatagaa accaacctgc tgcaacagca ttggccaaca aatagaagt gttcagatca       480 aatggcctca cggccaatga gtctggaagg ctcatagact tccttaagga tgtaatggag      540
tcaatgaaca agaagaaat gtggatcaca actcattttc agagaaagag acgggtgaga      600
gacaatatga ctaagaaaat gataacacag agaacaatgg gtaaaaagaa gcagagattg      660
aacaaaagga gttatctaat tagagcattg accctgaaca caatgaccaa agatgctgag      720
agagggaagc taaaacggag agcaattgca accccaggga tgcaaataag ggggtttgta      780
tactttgttg agacactggc aaggagtata tgtgagaaac ttgaacaatc agggttgcca      840
gttggaggca atgagaagaa agcaaagttg gcaaatgttg taaggaagat gatgaccaat      900
tctcaggaca ccgaactttc tttcaccatc actggagata acaccaaatg gaacgaaaat      960
cagaatcctc ggatgttttt ggccatgatc acatatatga ccagaaatca gcccgaatgg     1020
```

-continued

```
ttcagaaatg ttctaagtat tgctccaata atgttctcaa acaaaatggc gagactgggga      1080 aaagggtata tgtttgagag caagagtatg aaacttagaa ctcaaatacc tgcagaaatg      1140
ctagcaagca tcgatttgaa atatttcaat gattcaacaa gaaagaagat tgaaaaaatc      1200
cgaccgctct taatagaggg gactgcatca ttgagccctg gaatgatgat gggcatgttc      1260
aatatgttaa gcactgtatt aggcgtctcc atcctgaatc ttggacaaaa gagatacacc      1320
aagactactt actggtggga tggtcttcaa tcctctgacg attttgctct gattgtgaat      1380
gcacccaatc atgaagggat tcaagccgga gtcaacaggt tttatcgaac ctgtaagcta      1440
cttggaatca atatgagcaa gaaaaagtct tacataaaca gaacaggtac atttgaattc      1500
acaagttttt tctatcgtta tgggtttgtt gccaatttca gcatggagct tcccagtttt      1560
ggggtgtctg ggatcaacga gtcagcggac atgagtattg gagttactgt catcaaaaac      1620
aatatgataa acaatgatct tggtccagca acagctcaaa tggcccttca gttgttcatc      1680
aaagattaca ggtacacgta ccgatgccat ataggtgaca cacaaataca aacccgaaga      1740
tcatttgaaa taaagaaact gtgggagcaa acccgttcca aagctggact gctagtctcc      1800
gacggaggcc caaatttata caacattaga aatctccaca ttcctgaagt ctgcctaaaa      1860
tgggaattga tggatgagga ttaccagggg cgtttatgca acccactgaa cccatttgtc      1920
agccataaag aaattgaatc aatgaacaat gcagtgatga tgccagcaca tggtccagcc      1980
aaaaacatgg agtatgatgc tgttgcaaca acacactcct ggatcccaa aagaaatcga        2040 tccatcttga atacaagtca aagaggagta cttgaggatg aacaaatgta ccaaaggtgc       2100
tgcaatttat ttgaaaaatt cttccccagc agttcataca gaagaccagt cgggatatcc      2160
agtatggtgg aggctatggt ttccagagcc cgaattgatg cacggattga tttcgaatct      2220
ggaaggataa agaaagaaga gttcactgag atcatgaaga tctgttccac cattgaagag      2280
ctcagacggc aaaaatagtg aatttagctt gtccttcatg aaaaaatgcc ttgtttctac       2340
t                                                                        2341
```

<210> SEQ ID NO 3
<211> LENGTH: 1565
<212> TYPE: DNA
<213> ORGANISM: Influenza A
<220> FEATURE:
<221> NAME/KEY: misc_feature
<223> OTHER INFORMATION: NP gene segment (FGHY-2)

<400> SEQUENCE: 3

```
agcaaaagca gggtagataa tcactcactg agtgacatca aaatcatggc gtctcaaggc        60
accaaacgat cttacgaaca gatggagact gatggagaac gccagaatgc cactgaaatc       120
agagcatccg tcggaaaaat gattggtgga attggacgat tctacatcca aatgtgcacc       180
gaactcaaac tcagtgatta tgagggacgg ttgatccaaa acagcttaac aatagagaga       240
atggtgctct ctgcttttga cgaaaggaga aataaatacc ttgaagaaca tcccagtgcg       300
gggaaagatc ctaagaaaac tggaggacct atatacagga gagtaaacgg aaagtggatg       360
agagaactca tcctttatga caaagaagaa ttaaggcgaa tctggcgcca agctaataat       420
ggtgacgatg caacggctgg tctgactcac atgatgatct ggcattccaa tttgaatgat       480
gcaacttatc agaggacaag agctcttgtt cgcaccggaa tggatcccag gatgtgctct       540
ctgatgcaag gttcaactct ccctaggagg tctggagccg caggtgctgc agtcaaagga       600
gttggaacaa tggtgatgga attggtcaga atgatcaaac gtgggatcaa tgatcggaac       660
```

-continued

```
ttctggaggg gtgagaatgg acgaaaaaca agaattgctt atgaaagaat gtgcaacatt      720
ctcaaaggga aatttcaaac tgctgcacaa aaagcaatga tggatcaagt gagagagagc      780
cggaacccag ggaatgctga gttcgaagat ctcacttttc tagcacggtc tgcactcata      840
ttgagagggt cggttgctca caagtcctgc ctgcctgcct gtgtgtatgg acctgccgta      900
gccagtgggt acgactttga aagggaggga tactctctag tcggaataga ccctttcaga      960
ctgcttcaaa acagccgagt gtacagccta atcagaccaa atgagaatcc agcacacaag     1020
agtcaactgg tgtggatggc atgccattct gccgcatttg aagatctaag agtattaagc     1080
ttcatcaaag ggacgaaggt gctcccaaga gggaagcttt ccactagagg agttcaaatt     1140
gcttccaatg aaaatatgga gactatggaa tcaagtacac ttgaactgag aagcaggtac     1200
tgggccataa ggaccagaag tggaggaaac accaatcaac agagggcatc tgcgggccaa     1260
atcagcatac aacctacgtt ctcagtacag agaaatctcc cttttgacag aacaaccatt     1320
atggcagcat tcaatgggaa tacagagggg agaacatctg acatgaggac cgaaatcata     1380
aggatgatgg aaagtgcaag accagaagat gtgtctttcc aggggcgggg agtcttcgag     1440
ctctcggacg aaaaggcagc gagcccgatc gtgccttcct ttgacatgag taatgaagga     1500
tcttatttct cggagacaa tgcagaggag tacgacaatt aaagaaaaat acccttgttt     1560
ctact                                                                1565

<210> SEQ ID NO 4
<211> LENGTH: 2341
<212> TYPE: DNA
<213> ORGANISM: Influenza A
<220> FEATURE:
<221> NAME/KEY: misc_feature
<223> OTHER INFORMATION: PB1 gene segment (FGHY-2)

<400> SEQUENCE: 4
agcaaaagca ggcaaaccat ttgaatggat gtcaatccga ccttactttt cttaaaagtg       60
ccagcacaaa atgctataag cacaactttc ccttatactg gagatcctcc ttacagccat      120
gggacaggaa caggatacac cttggatact gtcaacagga cacatcagta ctcagaaaag      180
ggaagatgga caacaaacac cgaaactgga gcaccgcaac tcaacccgat tgatgggcca      240
ctgccagaag acaatgaacc aagtggttat gcccaaacag attgtgtatt ggaggcgatg      300
gctttccttg aggaatccca tcctggtatt tttgaaaact cgtgtattga aacgatggag      360
gttgttcagc aaaacacgag tagacaagct cacacaaggcc gacagaccta tgactggact      420
ctaaatagaa accaacctgc tgcaacagca ttggccaaca aatagaagt gttcagatca      480 aatggcctca cggccaatga gtctggaagg ctcatagact tccttaagga tgtaatggag      540
tcaatgaaca agaagaaat gtggatcaca actcattttc agagaaagag acgggtgaga      600
gacaatatga ctaagaaaat gataacacag agaacaatgg gtaaaaagaa gcagagattg      660
aacaaaagga gttatctaat tagagcattg accctgaaca caatgaccaa agatgctgag      720
agagggaagc taaaacggag agcaattgca accccaggga tgcaaataag ggggtttgta      780
tactttgttg agacactggc aaggagtata tgtgagaaac ttgaacaatc agggttgcca      840
gttggaggca atgagaagaa agcaaagttg gcaaatgttg taaggaagat gatgaccaat      900
tctcaggaca ccgaactttc tttcaccatc actggagata acaccaaatg gaacgaaaat      960
cagaatcctc ggatgtttttt ggccatgatc acatatatga ccagaaatca gcccgaatgg     1020
ttcagaaatg ttctaagtat tgctccaata atgttctcaa acaaaatggc gagactggga     1080
```

-continued

```
aaagggtata tgtttgagag caagagtatg aaacttagaa ctcaaatacc tgcagaaatg    1140
ctagcaagca tcgatttgaa atatttcaat gattcaacaa gaaagaagat tgaaaaaatc    1200
cgaccgctct aatagagggg gactgcatca ttgagccctg gaatgatgat gggcatgttc    1260
aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat ataggtgaca cacaaataca aacccgaaga    1740
tcatttgaaa taaagaaact gtgggagcaa acccgttcca aagctggact gctagtctcc    1800
gacggaggcc caaatttata caacattaga aatctccaca tttctgaagt ctgcctaaaa    1860
tgggaattga tggatgagga ttaccagggg cgtttatgca acccactgaa cccatttgtc    1920
agccataaag aaattgaatc aatgaacaat gcagtgatga tgccagcaca tggtccagcc    1980
aaaaacatgg agtatgatgc tgttgcaaca acacactcct ggatccccaa aagaaatcga    2040
tccatcttga atacaagtca agaggagta cttgaggatg aacaaatgta ccaaaggtgc    2100
tgcaatttat ttgaaaaatt cttccccagc agttcataca gaagaccagt cgggatatcc    2160
agtatggtgg aggctatggt ttccagagcc cgaattgatg cacggattga tttcgaatct    2220
ggaaggataa agaaagaaga gttcactgag atcatgaaga tctgttccac cattgaagag    2280
ctcagacggc aaaaatagtg aatttagctt gtccttcatg aaaaaatgcc ttgtttctac    2340
t                                                                    2341
```

<210> SEQ ID NO 5
<211> LENGTH: 2341
<212> TYPE: DNA
<213> ORGANISM: Influenza A
<220> FEATURE:
<221> NAME/KEY: misc_feature
<223> OTHER INFORMATION: PB2 gene segment (FGHY-2)

<400> SEQUENCE: 5

```
agcaaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg atcagaccg agtgatggta    300 tcacctctgg ctgtgacatg gtggaatagg aatggaccaa taacaaatac agttcattat    360
ccaaaaatct acaaaactta ttttgaaaga gtcgaaaggc taaagcatgg aaccttggc     420 cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccaga attgcaaaat ttctcctttg atggttgcat acatgttgga gagagaactg    660
gtccgcaaaa cgagattcct cccagtggct ggtggaacaa gcagtgtgta cattgaagtg    720
```

-continued

```
ttgcatttga ctcaaggaac atgctgggaa cagatgtata ctccaggagg ggaagtgagg     780
aatgatgatg ttgatcaaag cttgattatt gctgctagga acatagtgag aagagctgca     840
gtatcagcag atccactagc atctttattg gagatgtgcc acagcacaca gattggtgga     900
attaggatgg tagacatcct taggcagaac ccaacagaag agcaagccgt ggatatatgc     960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatatgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtca gaggtgatct gaatttcgtc aatagggcga atcaacgatt gaatcctatg    1320
catcaacttt taagacattt tcagaaggat gcgaaagtgc tttttcaaaa ttggggagtt    1380
gaacctatcg acaatgtgat gggaatgatt gggatattgc ccgacataac tccaagcatc    1440
gagatgtcaa tgagaggagt gagaatcagc aaaatgggtg tagatgagta ctccagcacg    1500
gagagggtag tggtgagcat tgaccgtttt ttgagagtcc gggaccaacg aggaaatgta    1560
ctactgtctc ccgaggaggt cagtgaaaca cagggaacag agaaactgac agtaacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca aagtagaatg    1920
cagttctcct catttactgt gaatgtgagg ggatcaggaa tgagaatact tgtaaggggc    1980
aattctcctg tattcaacta taacaaggcc acgaagagac tcacagttct cggaaaggat    2040
gctggcactt taactgaaga cccagatgaa ggcacagctg gagtggagtc cgctgttctg    2100
aggggattcc tcattctggg caaagaagac aagagatatg gccagcacat aagcatcaat    2160
gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
t                                                                    2341
```

<210> SEQ ID NO 6
<211> LENGTH: 498
<212> TYPE: PRT
<213> ORGANISM: Influenza A
<220> FEATURE:
<221> NAME/KEY: misc_feature
<223> OTHER INFORMATION: NP amino acid sequence (FGHY-1)

<400> SEQUENCE: 6

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60
```

-continued

```
Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Leu Arg Arg Ile Trp Arg Gln Ala Asn Asn Gly Asp Asp
            115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
            195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
            275                 280                 285

Tyr Asp Phe Glu Arg Lys Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
                420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480
```

-continued

```
Met Ser Asn Glu Gly Ser Tyr Phe Phe Gly Asp Asn Ala Glu Glu Tyr
                485                 490                 495

Asp Asn

<210> SEQ ID NO 7
<211> LENGTH: 757
<212> TYPE: PRT
<213> ORGANISM: Influenza A
<220> FEATURE:
<221> NAME/KEY: misc_feature
<223> OTHER INFORMATION: PB1 amino acid sequence (FGHY-1)

<400> SEQUENCE: 7

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Leu Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
                100                 105                 110

Val Val Gln Gln Thr Arg Val Asp Lys Leu Thr Gln Gly Arg Gln Thr
                115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Trp Ile Thr Thr His Phe Gln Arg Lys Arg Arg Val Arg
                180                 185                 190

Asp Asn Met Thr Lys Lys Met Ile Thr Gln Arg Thr Met Gly Lys Lys
                195                 200                 205

Lys Gln Arg Leu Asn Lys Arg Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335
```

-continued

```
Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asn
            450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Ile Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
```

-continued

```
         755

<210> SEQ ID NO 8
<211> LENGTH: 498
<212> TYPE: PRT
<213> ORGANISM: Influenza A
<220> FEATURE:
<221> NAME/KEY: misc_feature
<223> OTHER INFORMATION: NP amino acid sequence (FGHY-2)

<400> SEQUENCE: 8

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Leu Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Arg Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350
```

```
Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
                420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 9
<211> LENGTH: 757
<212> TYPE: PRT
<213> ORGANISM: Influenza A
<220> FEATURE:
<221> NAME/KEY: misc_feature
<223> OTHER INFORMATION: PB1 amino acid sequence (FGHY-2)

<400> SEQUENCE: 9

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Leu Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
                100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Trp Ile Thr Thr His Phe Gln Arg Lys Arg Arg Val Arg
                180                 185                 190

Asp Asn Met Thr Lys Lys Met Ile Thr Gln Arg Thr Met Gly Lys Lys
        195                 200                 205
```

```
Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
                355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Ile Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Ser Glu
                595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
```

-continued

```
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
                675                 680                 685

Tyr Gln Arg Cys Cys Asn Leu Phe Glu Lys Phe Phe Pro Ser Ser Ser
                690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
                740                 745                 750

Leu Arg Arg Gln Lys
          755

<210> SEQ ID NO 10
<211> LENGTH: 759
<212> TYPE: PRT
<213> ORGANISM: Influenza A
<220> FEATURE:
<221> NAME/KEY: misc_feature
<223> OTHER INFORMATION: PB2 amino acid sequence (FGHY-2)

<400> SEQUENCE: 10

Met Glu Arg Ile Lys Glu Leu Arg Asn Leu Met Ser Gln Ser Arg Thr
1                   5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
          35                  40                  45

Trp Met Met Ala Met Lys Tyr Pro Ile Thr Ala Asp Lys Arg Ile Thr
          50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
                100                 105                 110

Lys Ile Tyr Lys Thr Tyr Phe Glu Arg Val Glu Arg Leu Lys His Gly
          115                 120                 125

Thr Phe Gly Pro Val His Phe Arg Asn Gln Val Lys Ile Arg Arg Arg
          130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
                180                 185                 190

Leu Gln Asp Cys Lys Ile Ser Pro Leu Met Val Ala Tyr Met Leu Glu
          195                 200                 205

Arg Glu Leu Val Arg Lys Thr Arg Phe Leu Pro Val Ala Gly Gly Thr
          210                 215                 220
```

-continued

```
Ser Ser Val Tyr Ile Glu Val Leu His Leu Thr Gln Gly Thr Cys Trp
225             230             235             240

Glu Gln Met Tyr Thr Pro Gly Gly Glu Val Arg Asn Asp Asp Val Asp
                245             250             255

Gln Ser Leu Ile Ile Ala Ala Arg Asn Ile Val Arg Arg Ala Ala Val
            260             265             270

Ser Ala Asp Pro Leu Ala Ser Leu Leu Glu Met Cys His Ser Thr Gln
        275             280             285

Ile Gly Gly Ile Arg Met Val Asp Ile Leu Arg Gln Asn Pro Thr Glu
    290             295             300

Glu Gln Ala Val Asp Ile Cys Lys Ala Ala Met Gly Leu Arg Ile Ser
305             310             315             320

Ser Ser Phe Ser Phe Gly Gly Phe Thr Phe Lys Arg Thr Ser Gly Ser
            325             330             335

Ser Val Lys Arg Glu Glu Glu Val Leu Thr Gly Asn Leu Gln Thr Leu
            340             345             350

Lys Ile Arg Val His Glu Gly Tyr Glu Glu Phe Thr Met Val Gly Arg
        355             360             365

Arg Ala Thr Ala Ile Leu Arg Lys Ala Thr Arg Arg Leu Ile Gln Leu
    370             375             380

Ile Val Ser Gly Arg Asp Glu Gln Ser Ile Ala Glu Ala Ile Ile Val
385             390             395             400

Ala Met Val Phe Ser Gln Glu Asp Cys Met Ile Lys Ala Val Arg Gly
            405             410             415

Asp Leu Asn Phe Val Asn Arg Ala Asn Gln Arg Leu Asn Pro Met His
            420             425             430

Gln Leu Leu Arg His Phe Gln Lys Asp Ala Lys Val Leu Phe Gln Asn
        435             440             445

Trp Gly Val Glu Pro Ile Asp Asn Val Met Gly Met Ile Gly Ile Leu
    450             455             460

Pro Asp Ile Thr Pro Ser Ile Glu Met Ser Met Arg Gly Val Arg Ile
465             470             475             480

Ser Lys Met Gly Val Asp Glu Tyr Ser Ser Thr Glu Arg Val Val Val
            485             490             495

Ser Ile Asp Arg Phe Leu Arg Val Arg Asp Gln Arg Gly Asn Val Leu
            500             505             510

Leu Ser Pro Glu Glu Val Ser Glu Thr Gln Gly Thr Glu Lys Leu Thr
        515             520             525

Val Thr Tyr Ser Ser Ser Met Met Trp Glu Ile Asn Gly Pro Glu Ser
    530             535             540

Val Leu Val Asn Thr Tyr Gln Trp Ile Ile Arg Asn Trp Glu Thr Val
545             550             555             560

Lys Ile Gln Trp Ser Gln Asn Pro Thr Met Leu Tyr Asn Lys Met Glu
            565             570             575

Phe Glu Pro Phe Gln Ser Leu Val Pro Lys Ala Ile Arg Gly Gln Tyr
            580             585             590

Ser Gly Phe Val Arg Thr Leu Phe Gln Gln Met Arg Asp Val Leu Gly
        595             600             605

Thr Phe Asp Thr Ala Gln Ile Ile Lys Leu Leu Pro Phe Ala Ala Ala
    610             615             620

Pro Pro Lys Gln Ser Arg Met Gln Phe Ser Ser Phe Thr Val Asn Val
625             630             635             640

Arg Gly Ser Gly Met Arg Ile Leu Val Arg Gly Asn Ser Pro Val Phe
```

-continued

```
                 645                 650                 655
Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
                740                 745                 750

Arg Ile Arg Met Ala Ile Asn
        755
```

```
<210> SEQ ID NO 11
<211> LENGTH: 976
<212> TYPE: DNA
<213> ORGANISM: Influenza A
<220> FEATURE:
<221> NAME/KEY: misc_feature
<223> OTHER INFORMATION: M gene segment

<400> SEQUENCE: 11
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggaacgggg atccaaataa     300
catggacaaa gcagttaaac tgtataggaa gctcaagagg gagataacat tccatggggc     360
caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggtttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgattaata ggatcgtctt tttttcaaat gcatttaccg tcgctttaaa tacgactga     840 aaggagggcc ttctacggaa ggagtgccaa agtctatgag ggaagaatat cgaaaggaac     900
agcagagtgc tgtggatgct gacgatggtc attttgtcag catagagctg gagtaaaaaa     960
ctaccttgtt tctact                                                       976
```

```
<210> SEQ ID NO 12
<211> LENGTH: 24
<212> TYPE: PRT
<213> ORGANISM: Influenza A
<220> FEATURE:
<221> NAME/KEY: misc_feature
<223> OTHER INFORMATION: M2 amino acid sequence

<400> SEQUENCE: 12
```

```
Met Ser Leu Leu Thr Glu Val Glu Thr Pro Ile Arg Asn Glu Trp Gly
1               5                   10                  15

Cys Arg Cys Asn Gly Ser Ser Asp
            20

<210> SEQ ID NO 13
<211> LENGTH: 566
<212> TYPE: PRT
<213> ORGANISM: Influenza A
<220> FEATURE:
<221> NAME/KEY: misc_feature
<223> OTHER INFORMATION: HA amino acid sequence of Vero-adapted
      influenza A/Massachusetts/15/2013 (HA-MA15V)

<400> SEQUENCE: 13

Met Lys Ala Ile Leu Val Val Leu Leu Tyr Thr Phe Ala Ala Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
        130                 135                 140

Ser Ser Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
            195                 200                 205

Tyr Gln Asn Ala Asp Ala Tyr Val Phe Val Gly Thr Ser Arg Tyr Ser
        210                 215                 220

Lys Lys Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
```

-continued

```
                    325                 330                 335
Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Asn Leu Asp Tyr His Asp Ser Asn Val Lys Asn Leu Tyr Glu
        450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 14
<211> LENGTH: 2341
<212> TYPE: DNA
<213> ORGANISM: Influenza A
<220> FEATURE:
<221> NAME/KEY: misc_feature
<223> OTHER INFORMATION: PB2 gene segment (FGHY-1)

<400> SEQUENCE: 14

```
agcaaaagca ggtcaattat attcaatatg gaaagaataa aagaactacg aaatctaatg      60
tcgcagtctc gcacccgcga gatactcaca aaaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg gatcagaccg agtgatggta     300
tcacctctgg ctgtgacatg gtggaatagg aatggaccaa taacaaatac agttcattat     360
ccaaaaatct acaaaactta ttttgaaaga gtcgaaaggc taaagcatgg aaccttttggc    420 cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taaccaaaga gaagaaagaa     600
gaactccagg attgcaaaat ttctcctttg atggttgcat acatgttgga gagagaactg     660
```

```
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagagtcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg gccagcact aagcatcaat   2160 gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

```
<210> SEQ ID NO 15
<211> LENGTH: 759
<212> TYPE: PRT
<213> ORGANISM: Influenza A
<220> FEATURE:
<221> NAME/KEY: misc_feature
<223> OTHER INFORMATION: PB2 amino acid sequence (FGHY-1)

<400> SEQUENCE: 15

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45
```

```
Trp Met Met Ala Met Lys Tyr Pro Ile Thr Ala Asp Lys Arg Ile Thr
    50              55                  60

Glu Met Ile Pro Glu Arg Asn Glu Gln Gly Gln Thr Leu Trp Ser Lys
65              70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
            115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
            195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
            275                 280                 285

Ile Gly Gly Ile Arg Met Val Asp Ile Leu Arg Gln Asn Pro Thr Glu
            290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
            355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
            435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
```

-continued

```
465              470              475              480

Ser Lys Met Gly Val Asp Glu Tyr Ser Ser Thr Glu Arg Val Val Val
             485              490              495

Ser Ile Asp Arg Phe Leu Arg Val Arg Asp Gln Arg Gly Asn Val Leu
             500              505              510

Leu Ser Pro Glu Glu Val Ser Glu Thr Gln Gly Thr Glu Lys Leu Thr
             515              520              525

Ile Thr Tyr Ser Ser Ser Met Met Trp Glu Ile Asn Gly Pro Glu Ser
             530              535              540

Val Leu Val Asn Thr Tyr Gln Trp Ile Ile Arg Asn Trp Glu Thr Val
545              550              555              560

Lys Ile Gln Trp Ser Gln Asn Pro Thr Met Leu Tyr Asn Lys Met Glu
             565              570              575

Phe Glu Pro Phe Gln Ser Leu Val Pro Lys Ala Ile Arg Gly Gln Tyr
             580              585              590

Ser Gly Phe Val Arg Thr Leu Phe Gln Gln Met Arg Asp Val Leu Gly
             595              600              605

Thr Phe Asp Thr Ala Gln Ile Ile Lys Leu Leu Pro Phe Ala Ala Ala
             610              615              620

Pro Pro Lys Gln Ser Arg Met Gln Phe Ser Ser Phe Thr Val Asn Val
625              630              635              640

Arg Gly Ser Gly Met Arg Ile Leu Val Arg Gly Asn Ser Pro Val Phe
             645              650              655

Asn Tyr Asn Lys Ala Thr Lys Arg Leu Thr Val Leu Gly Lys Asp Ala
             660              665              670

Gly Thr Leu Thr Glu Asp Pro Asp Glu Gly Thr Ala Gly Val Glu Ser
             675              680              685

Ala Val Leu Arg Gly Phe Leu Ile Leu Gly Lys Glu Asp Lys Arg Tyr
             690              695              700

Gly Pro Ala Leu Ser Ile Asn Glu Leu Ser Asn Leu Ala Lys Gly Glu
705              710              715              720

Lys Ala Asn Val Leu Ile Gly Gln Gly Asp Val Val Leu Val Met Lys
             725              730              735

Arg Lys Arg Asp Ser Ser Ile Leu Thr Asp Ser Gln Thr Ala Thr Lys
             740              745              750

Arg Ile Arg Met Ala Ile Asn
             755
```

<210> SEQ ID NO 16
<211> LENGTH: 2233
<212> TYPE: DNA
<213> ORGANISM: Influenza A
<220> FEATURE:
<221> NAME/KEY: misc_feature
<223> OTHER INFORMATION: PA gene segment (FGHY-1 and FGHY-2)

<400> SEQUENCE: 16

```
agcaaaagca ggtactgatc caaaatggaa gattttgtgc gacaatgctt caatccgatg     60
attgtcgagc ttgcggaaaa aacaatgaaa gagtatgggg aggacctgaa aatcgaaaca    120
aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
```

-continued

```
aaggagaata gattcatcga aattggagta acaaggagag aagttcacat atactatctg      420
gaaaaggcca ataaaattaa atctgagaaa acacacatcc acattttctc gttcactggg      480
gaagaaatgg ccacaaaggc agactacact ctcgatgaag aaagcagggc taggatcaaa      540
accagactat tcaccataag acaagaaatg gccagcagag gcctctggga ttcctttcgt      600
cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa acaacaccac gaccacttag acttccgaat      840
gggcctccct gttctcagcg gtccaaattc ctgctgatgg atgccttaaa attaagcatt      900
gaggacccaa gtcatgaagg agagggaata ccgctatatg atgcaatcaa atgcatgaga      960
acattctttg gatggaagga acccaatgtt gttaaaccac acgaaaaggg aataaatcca     1020
aattatcttc tgtcatggaa gcaagtactg gcagaactgc aggacattga gaatgaggag     1080
aaaattccaa agactaaaaa tatgaagaaa acaagtcagc taaagtgggc acttggtgag     1140
aacatggcac cagaaaaggt agactttgac gactgtaaag atgtaggtga tttgaagcaa     1200
tatgatagta tgaaccaga attgaagtcg cttgcaagtt ggattcagaa tgagtttaac     1260
aaggcatgcg aactgacaga ttcaagctgg atagagctcg atgagattgg agaagatgtg     1320
gctccaattg aacacattgc aagcatgaga aggaattatt tcacatcaga ggtgtctcac     1380
tgcagagcca cagaatacat aatgaaggga gtgtacatca atactgcctt gcttaatgca     1440
tcttgtgcag caatggatga tttccaatta attccaatga taagcaagtg tagaactaag     1500
gagggaaggc gaaagaccaa cttgtatggt ttcatcataa aaggaagatc ccacttaagg     1560
aatgacaccg acgtggtaaa ctttgtgagc atggagtttt ctctcactga cccaagactt     1620
gaaccacata atgggagaa gtactgtgtt cttgagatag gagatatgct tataagaagt     1680
gccataggcc aggtttcaag gcccatgttc ttgtatgtga aacaaatgg aacctcaaaa     1740 attaaaatga atggggaat ggagatgagg cgttgcctcc tccagtcact tcaacaaatt     1800
gagagtatga ttgaagctga gtcctctgtc aaagagaaag acatgaccaa agagttcttt     1860
gagaacaaat cagaaacatg gcccattgga gagtccccca aaggagtgga ggaaagttcc     1920
attgggaagg tctgcaggac ttttattagca aagtcggtat tcaacagctt gtatgcatct     1980
ccacaactag aaggattttc agctgaatca agaaaactgc ttcttatcgt tcaggctctt     2040
agggacaacc tggaacctgg gacctttgat cttgggggggc tatatgaagc aattgaggag     2100
tgcctgatta atgatccctg ggttttgctt aatgcttctt ggttcaactc cttccttaca     2160
catgcattga gttagttgtg gcagtgctac tatttgctat ccatactgtc caaaaaagta     2220
ccttgtttct act                                                        2233
```

```
<210> SEQ ID NO 17
<211> LENGTH: 716
<212> TYPE: PRT
<213> ORGANISM: Influenza A
<220> FEATURE:
<221> NAME/KEY: misc_feature
<223> OTHER INFORMATION: PA amino acid sequence (FGHY-1 and FGHY-2)

<400> SEQUENCE: 17

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
```

-continued

```
                  20                  25                  30
Asn Lys Phe Ala Ala Ile Cys Thr His Leu Glu Val Cys Phe Met Tyr
        35                  40                  45
Ser Asp Phe His Phe Ile Asn Glu Gln Gly Glu Ser Ile Ile Val Glu
        50                  55                  60
Leu Gly Asp Pro Asn Ala Leu Leu Lys His Arg Phe Glu Ile Ile Glu
65                  70                  75                  80
Gly Arg Asp Arg Thr Met Ala Trp Thr Val Val Asn Ser Ile Cys Asn
                85                  90                  95
Thr Thr Gly Ala Glu Lys Pro Lys Phe Leu Pro Asp Leu Tyr Asp Tyr
                100                 105                 110
Lys Glu Asn Arg Phe Ile Glu Ile Gly Val Thr Arg Arg Glu Val His
        115                 120                 125
Ile Tyr Tyr Leu Glu Lys Ala Asn Lys Ile Lys Ser Glu Lys Thr His
        130                 135                 140
Ile His Ile Phe Ser Phe Thr Gly Glu Glu Met Ala Thr Lys Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Ser Arg Gly Leu Trp Asp Ser Phe Arg
                180                 185                 190
Gln Ser Glu Arg Gly Glu Glu Thr Ile Glu Glu Arg Phe Glu Ile Thr
        195                 200                 205
Gly Thr Met Arg Lys Leu Ala Asp Gln Ser Leu Pro Pro Asn Phe Ser
        210                 215                 220
Ser Leu Glu Asn Phe Arg Ala Tyr Val Asp Gly Phe Glu Pro Asn Gly
225                 230                 235                 240
Tyr Ile Glu Gly Lys Leu Ser Gln Met Ser Lys Glu Val Asn Ala Arg
                245                 250                 255
Ile Glu Pro Phe Leu Lys Thr Thr Pro Arg Pro Leu Arg Leu Pro Asn
                260                 265                 270
Gly Pro Pro Cys Ser Gln Arg Ser Lys Phe Leu Leu Met Asp Ala Leu
        275                 280                 285
Lys Leu Ser Ile Glu Asp Pro Ser His Glu Gly Glu Gly Ile Pro Leu
        290                 295                 300
Tyr Asp Ala Ile Lys Cys Met Arg Thr Phe Phe Gly Trp Lys Glu Pro
305                 310                 315                 320
Asn Val Val Lys Pro His Glu Lys Gly Ile Asn Pro Asn Tyr Leu Leu
                325                 330                 335
Ser Trp Lys Gln Val Leu Ala Glu Leu Gln Asp Ile Glu Asn Glu Glu
                340                 345                 350
Lys Ile Pro Lys Thr Lys Asn Met Lys Lys Thr Ser Gln Leu Lys Trp
        355                 360                 365
Ala Leu Gly Glu Asn Met Ala Pro Glu Lys Val Asp Phe Asp Asp Cys
        370                 375                 380
Lys Asp Val Gly Asp Leu Lys Gln Tyr Asp Ser Asp Glu Pro Glu Leu
385                 390                 395                 400
Lys Ser Leu Ala Ser Trp Ile Gln Asn Glu Phe Asn Lys Ala Cys Glu
                405                 410                 415
Leu Thr Asp Ser Ser Trp Ile Glu Leu Asp Glu Ile Gly Glu Asp Val
                420                 425                 430
Ala Pro Ile Glu His Ile Ala Ser Met Arg Arg Asn Tyr Phe Thr Ser
        435                 440                 445
```

-continued

```
Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
        530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
        610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
        690                 695                 700

Ser Trp Phe Asn Ser Phe Leu Thr His Ala Leu Ser
705                 710                 715
```

```
<210> SEQ ID NO 18
<211> LENGTH: 890
<212> TYPE: DNA
<213> ORGANISM: Influenza A
<220> FEATURE:
<221> NAME/KEY: misc_feature
<223> OTHER INFORMATION: NS gene segment (FGHY-1 and FGHY-2)

<400> SEQUENCE: 18
agcaaaagca gggtgacaaa aacataatgg atccaaacac tgtgtcaagc tttcaggtag      60
attgctttct ttggcatgtc cgcaaacgag ttgcagacca agaactaggc gatcccccat     120
tccttgatcg gcttcgccga gatcagaaat ccctaagagg aaggggcagt actctcggtc     180
tggacatcaa gacagccaca cgtgctggaa agcagatagt ggagcggatt ctgaaagaag     240
aatccgatga ggcacttaaa atgaccatgg cctctgtacc tgcgtcgcgt tacctaactg     300
acatgactct tgaggaaatg tcaagggact ggtccatgct catacccaag cagaaagtgg     360
caggccctct ttgtatcaaa atggaccagg cgatcatgga taagaacatc atactgaaag     420
cgaacttcag tgtgattttt gaccggctgg agactctaat attgctaagg gctttcaccg     480
```

-continued

```
aagagggagc aattgttggc gaaatttcac cattgccttc tcttccagga catactgctg        540
aggatgtcaa aaatgcagtt ggagtcctca tcggaggact tgaatggaat gataacacag        600
ttcgagtctc tgaaactcta cagagattcg cttggagaag cagtaatgag aatgggagac        660
ctccactcac tccaaaacag aaacgagaaa tggcgggaac aattaggtca gaagtttgaa        720
gaaataagat ggttgattga agaagtgaga cacaaactga agataacaga gaatagtttt        780
gagcaaataa catttatgca agccttacat ctattgcttg aagtggagca agagataaga        840
actttctcgt ttcagcttat ttagtactaa aaaacaccct tgtttctact             890
```

<210> SEQ ID NO 19
<211> LENGTH: 230
<212> TYPE: PRT
<213> ORGANISM: Influenza A
<220> FEATURE:
<221> NAME/KEY: misc_feature
<223> OTHER INFORMATION: NS1 amino acid sequence

<400> SEQUENCE: 19

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
                180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230
```

<210> SEQ ID NO 20
<211> LENGTH: 121
<212> TYPE: PRT
<213> ORGANISM: Influenza A
<220> FEATURE:
<221> NAME/KEY: misc_feature
<223> OTHER INFORMATION: NS2 amino acid sequence (FGHY-1 and FGHY-2

-continued

```
<400> SEQUENCE: 20

Met Asp Pro Asn Thr Val Ser Ser Phe Gln Asp Ile Leu Leu Arg Met
1               5                   10                  15

Ser Lys Met Gln Leu Glu Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Ile Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120
```

INFLUENZA VIRUS BACKBONE

CROSS-REFERENCE TO RELATED APPLICATIONS

This patent application claims the benefit of U.S. Provisional Patent Application 62/858,737, filed on Jun. 7, 2019, which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 73,647 bytes ASCII (Text) file named "758243Sequence-Listing.txt." created Dec. 2, 2021.

BACKGROUND OF THE INVENTION

Influenza, i.e., the "flu," is a highly contagious viral infection that claims the lives of hundreds of thousands of humans globally each year. There are four types of influenza viruses (i.e., A, B, C, and D) categorized based on their core proteins, although seasonal epidemics are most often caused by circulating Influenza A and B viruses.

While vaccines are the best way to prevent influenza, influenza vaccines must be re-formulated often, as the influenza virus is subject to antigenic drift and antigenic shift. Moreover, because influenza viruses, particularly Influenza A, generally exhibit a high rate of mutation and evolution, influenza vaccine strains may mismatch circulating strains, resulting in minimal vaccine effectiveness. However, when circulating flu viruses are well-matched to the flu vaccine, vaccination can reduce the risk of flu-related illness by 40%-60% among the overall population. Accordingly, researchers have been studying vaccines that can induce cross-protective immunity between different influenza subtypes. One such example is a vaccine comprising a live, attenuated influenza virus that does not express a functional M2 protein (e.g., the M2SR vaccine).

Influenza vaccines are preferably propagated in Madin-Darby canine kidney (MDCK) cells and African Green Monkey (Vero) cells, as mammalian-cell cultures provide advantages over egg-based production. These advantages include lower costs, faster production time, and a reduced risk of antigenic mutation in the virus. For example, the M2SR vaccine is propagated in Vero cells that stably express M2 protein. However, vaccine production in cell cultures has often resulted in undesirable yields. Moreover, MDCK cells are generally more permissive than Vero cells, such that vaccine production in Vero cells is comparatively inefficient.

Modifications to the virus backbone, i.e., the six internal gene segments consisting of PB1, PB2, PA, NP, M, and NS, have been shown to boost vaccine production. For example, the high-yield vaccine backbone "PR8-HY" developed and described in Ping et al., *Nature Communications*, 6: 8148 (2015), comprises specific amino acid mutations in the PB1, PB2, PA, NP, and NS1 proteins, and was expected to improve the titers of pandemic and seasonal influenza vaccines in both cell and egg culture systems. However, these modifications described in the art have been ineffective in increasing viral growth in Vero cells, particularly under preferred manufacturing conditions. Therefore a need exists to enhance viral growth in Vero cells, such that vaccines, like the M2SR vaccine, can be produced more efficiently and effectively.

BRIEF SUMMARY OF THE INVENTION

The invention provides an influenza virus having enhanced growth in Vero cells. The influenza virus comprises gene segments encoding proteins, e.g., the PB1, PB2, PA, NP, and NS1 proteins, having amino acid sequences comprising selected amino acids. For example, the PB1 protein comprises a leucine at position 40 and a tryptophan at position 180, and at least one of an asparagine at position 464 or a serine at position 607. The PB2 protein comprises a valine at position 504, and optionally an isoleucine at position 467 and a valine at position 529. The PA protein comprises a lysine at position 401. The NP protein comprises a leucine at position 116, and at least one of a lysine at position 294 or an arginine at position 311. The NS1 protein comprises a proline at position 30 and a lysine at position 118. Furthermore, at least one of the PB1, PB2, and PA gene segments optionally comprises a cytosine to uracil promoter mutation at nucleotide position 4.

The invention also provides a pharmaceutical formulation comprising the influenza virus, a method of eliciting an immune response in a mammal comprising administering the influenza virus to the mammal, and a method of generating the influenza virus.

BRIEF DESCRIPTION OF THE DRAWINGS

FIG. 7A is a table that shows HA mutations in Vero-adapted H1N1 viruses.

FIG. 7B is a table that shows HA mutations in Vero-adapted H3N2 viruses.

FIG. 9B depicts the proportion of cells expressing high NP levels to cells expressing low NP levels in different cell lines after infection with Sing10 viruses having different backbones (i.e., FGHY1, UW-PR8 ("HG")) on Day 1 post-infection.

DETAILED DESCRIPTION OF THE INVENTION

Figure 1A:
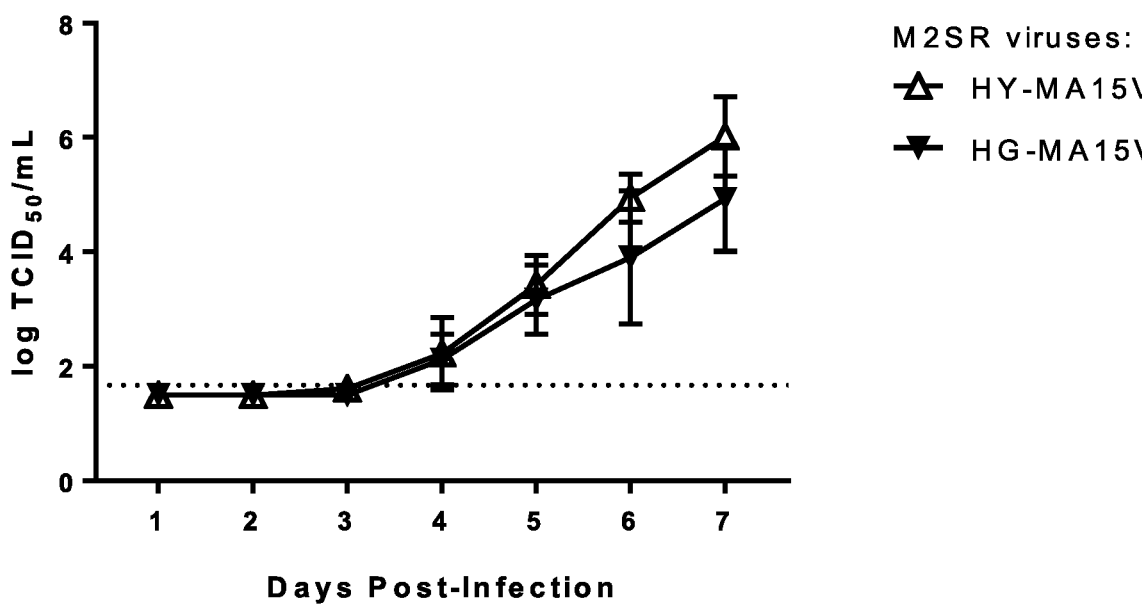
FIG. 1A is a graph of virus titer (log $TCID_{50}$/ml) versus time (days post-infection) depicting the growth curve for A/Massachusetts/15/2013 M2SR viruses comprising a Vero-adapted HA protein (i.e., M2SR-MA15V viruses) comprising UW-PR8 ("HG") and PR8-HY ("HY") backbones in Vero cells.

The influenza virus of the invention may be any type of influenza virus. For example, the influenza virus may be any subtype of Influenza A. In some embodiments, the influenza virus may be a pandemic Influenza A virus (e.g., H5N1). In other embodiments, the influenza virus may be a seasonal Influenza A virus (e.g., H1N1 or H3N2). In some embodiments, the influenza virus may be a recombinant influenza virus. As used herein, a recombinant influenza virus (e.g., a reassortant influenza virus) is an influenza virus comprising genetic material (e.g., gene segments) derived from a genetically distinct influenza virus (e.g., heterologous gene segments). The influenza virus may also be an isolated influenza virus.

As used herein, the term "gene segment" refers to the nucleotide sequence that encodes a viral protein. The gene segment may be represented by the cDNA (complementary DNA) sequence encoding the viral RNA (vRNA), i.e., SEQ ID NOs: 1-5, 11, 14, 16, 18, that encodes the viral protein.

As used herein, the term "backbone" refers to the influenza gene segments encoding the PB1, PB2, PA, NP, NS1 and/or NS2, and M proteins. The gene segments of the present invention encode proteins having selected amino acids.

As used herein, the term "selected amino acid" refers to a specific amino acid in a particular position of an amino acid sequence. In some embodiments, the selected amino acid is the result of a genetic mutation to a parent amino acid sequence. The parent amino acid sequence may be identical to the amino acid sequence comprising the selected amino acid, except for the position corresponding to the selected amino acid.

The Influenza Virus (A) Backbone Proteins

The PB1 (polymerase base protein 1) gene segment of the invention may encode a protein, i.e., a PB1 protein, comprising at least one selected amino acid. In a preferred embodiment, the selected amino acids comprise a leucine at position 40 and a tryptophan at position 180. The selected amino acids of the PB1 protein further comprise at least one of an asparagine at position 464 or a serine at position 607. The PB1 gene segment may optionally comprise a cytosine to uracil promoter mutation at nucleotide position 4.

The selected amino acids may be acquired by genetic mutation to a parent PB1 sequence, e.g., a sequence identical to the PB1 amino acid sequence of the invention, except for the positions corresponding to the selected amino acids. The amino acid position 464 of the PB1 protein is located in the palm region of the influenza PB1 protein and connects RNA-dependent RNA polymerase activity domains. Generally, the aspartic acid at position 464 is highly conserved among influenza viruses isolated in eggs and MDCK cells. Although the role of this amino acid has not been identified, the observed amino acid change to asparagine (N) at this position may affect PB1 protein conformation and may affect interaction with a host cell factor and, therefore, polymerase activity in Vero cells. Moreover, since histidine at position 465 of the PB1 protein interacts with glutamic acid at position 243 of the PA protein, the amino acid change at position 464 of PB1 may alter interactions between PB1 and PA. The function of the amino acid at position 607 of the PB1 protein is also unknown; however, this amino acid is located between the RNA-dependent RNA polymerase region and the PB2 binding region, suggesting that it may alter interactions between PB1 and PB2, thereby affecting polymerase activity in Vero cells.

The PB2 (polymerase base protein 2) gene segment of the invention may also encode a protein, i.e., a PB2 protein, comprising at least one selected amino acid. In a preferred embodiment, the selected amino acids comprise a valine at position 504 and optionally an isoleucine at position 467 and a valine at position 529. The PB2 gene segment may optionally comprise a cytosine to uracil promoter mutation at nucleotide position 4. The amino acids position 467 and 529 of the PB2 protein are in the PB2-C portion. Specifically, the amino acid at portion 467 is located in the cap-binding region of the PB2 protein, and the amino acid at position 529 is located in the cap-627 linker domain. In some influenza viruses, the PB2 protein binds the cap structure of host capped RNA and utilizes the cap from the host RNA in order to make influenza mRNAs. This process is known as "cap-snatching." Moreover, the amino acid at position 627 of PB2 is known to be a key determinant in host range and viral pathogenicity. Therefore, amino acid changes proximate to a cap-binding region may affect the efficiency of viral mRNA synthesis.

The PA (polymerase acidic protein) gene segment of the invention may also encode a protein, i.e., a PA protein, comprising at least one selected amino acid. In a preferred embodiment, the selected amino acids comprise a lysine at position 401. The PA gene segment may optionally comprise a cytosine to uracil promoter mutation at nucleotide position 4.

The NP (nucleoprotein) gene segment of the invention may also encode a protein, i.e., an NP protein, comprising at least one selected amino acid. In a preferred embodiment, the selected amino acids comprise a leucine at position 116 and at least one of a lysine at position 294 or an arginine at position 311. The amino acid positions 294 and 311 of the NP protein are located in the body of the NP protein, such that they neither serve as nuclear localization signals nor nuclear export signals.

The NS (non-structural) gene segment of the invention may also encode a protein, i.e., an NS1 and/or NS2 protein, comprising at least one selected amino acid. In a preferred embodiment, the selected amino acids comprise a proline at position 30 (NS1 protein) and a lysine at position 118 (NS1 protein).

In one embodiment of the invention, the influenza virus comprises a PB1 gene segment encoding a protein, i.e., a PB1 protein, having selected amino acids at positions 40, 180, and 464, i.e., a leucine at position 40, a tryptophan at position 180, and an asparagine at position 464. The PB1 gene segment may have a nucleotide sequence represented by SEQ ID NO: 2. The PB1 gene segment may encode a protein, i.e., a PB1 protein, having an amino acid sequence of SEQ ID NO: 7. In another aspect of the embodiment, the influenza virus may comprise a PB2 gene segment encoding a protein, i.e., a PB2 protein, having a selected amino acid at position 504, i.e., a valine at position 504. The PB2 gene segment may have a nucleotide sequence represented by SEQ ID NO: 14. The PB2 gene segment may encode a protein, i.e., a PB2 protein, having an amino acid sequence of SEQ ID NO: 15. The NP gene segment of the embodiment may encode a protein, i.e., an NP protein, having selected amino acids at positions 116 and 294, i.e., a leucine at position 116 and a lysine at position 294. The NP gene segment may have a nucleotide sequence represented by SEQ ID NO: 1. The NP gene segment may encode a protein, i.e., an NP protein, having an amino acid sequence of SEQ ID NO: 6. The PA and NS gene segments of the embodiment may also encode proteins, i.e., a PA protein and NS1 and/or NS2 protein, comprising selected amino acids at position 401 (PA protein), position 30 (NS1 protein), and position 118 (NS1 protein), i.e., a lysine at position 401 (PA protein), a proline at position 30 (NS1 protein), and a lysine at position 118 (NS1 protein). The PA gene segment may have a nucleotide sequence represented by SEQ ID NO: 16. The PA gene segment may encode a protein, i.e., a PA protein, having an amino acid sequence of SEQ ID NO: 17. The NS gene segment may have a nucleotide sequence represented by SEQ ID NO: 18. The NS gene segment may encode a protein, i.e., an NS1 protein, having an amino acid sequence of SEQ ID NO: 19. The NS gene segment may encode a protein, i.e., an NS2 protein, having an amino acid sequence of SEQ ID NO: 20. The PB1, PB2, and PA gene segments of the embodiment may also comprise a cytosine to uracil promoter mutation at nucleotide position 4.

In another embodiment of the invention, the influenza virus comprises a PB1 gene segment encoding a protein, i.e., a PB1 protein, having selected amino acids at positions 40, 180, and 607, i.e., a leucine at position 40, a tryptophan at position 180, and a serine at position 607. The PB1 gene segment may have a nucleotide sequence represented by SEQ ID NO: 4. The PB1 gene segment may encode a protein, i.e., a PB1 protein, having an amino acid sequence of SEQ ID NO: 9. In another aspect of the embodiment, the influenza virus may comprise a PB2 gene segment encoding a protein, i.e., PB2 protein, having selected amino acids at positions 504, 467, and 529, i.e., a valine at position 504, an isoleucine at position 467, and a valine at position 529. The PB2 gene segment may have a nucleotide sequence represented by SEQ ID NO: 5. The PB2 gene segment may encode a protein, i.e., a PB2 protein, having an amino acid sequence of SEQ ID NO: 10. The NP gene segment of the embodiment may encode a protein, i.e., an NP protein, having selected amino acids at positions 116 and 311, i.e., a leucine at position 116 and an arginine at position 311. The NP gene segment may have a nucleotide sequence represented by SEQ ID NO: 3. The NP gene segment may encode a protein, i.e., an NP protein, having an amino acid sequence of SEQ ID NO: 8. The PA and NS gene segments may also encode proteins, i.e., a PA protein and NS1 and/or NS2 protein, comprising selected amino acids at position 401 (PA protein), position 30 (NS1 protein), and position 118 (NS1 protein), i.e., a lysine at position 401 (PA protein), a proline at position 30 (NS1 protein), and a lysine at position 118 (NS1 protein). The PA gene segment may have a nucleotide sequence represented by SEQ ID NO: 16. The PA gene segment may encode a protein, i.e., a PA protein, having an amino acid sequence of SEQ ID NO: 17. The NS gene segment may have a nucleotide sequence represented by SEQ ID NO: 18. The NS gene segment may encode a protein, i.e., an NS1 protein, having an amino acid sequence of SEQ ID NO: 19. The NS gene segment may encode a protein, i.e., an NS2 protein, having an amino acid sequence of SEQ ID NO: 20. The PB1, PB2, and PA gene segments of the embodiment may also comprise a cytosine to uracil promoter mutation at nucleotide position 4.

The selected amino acids of the embodiments, particularly in most proteins of the backbone, confer enhanced growth properties onto the influenza virus, as compared to an influenza virus that is the same except without the selected amino acids, under the same conditions. For example, the influenza virus of the invention exhibits enhanced growth in Vero cells.

The influenza virus of the invention may also comprise an M (membrane protein) gene segment. In one embodiment of the invention, the M gene segment may be a mutant gene segment from Influenza A, such that the virus lacks expression of functional M2 protein. Such a virus is herein referred to as an "M2SR" virus. The M2SR virus is a single replication influenza virus. The M gene segment of the M2SR virus may be represented by SEQ ID NO: 11. The M gene segment may encode a protein, e.g., a truncated M2 protein, having the amino acid sequence of SEQ ID NO: 12. The M2SR virus may be propagated in Vero cells that stably express the M2 protein (i.e., M2VeroA cells) to allow for multicycle replication. High yield in Vero cells is not dependent on mutation in the M gene segment. Therefore, the influenza virus of the invention may comprise an M gene segment that encodes a functional M2 protein.

(B) Surface Proteins

In a further embodiment of the invention, the influenza virus comprises an NA (neuraminidase) and HA (hemagglutinin) gene segment. In one embodiment of the invention, the HA gene segment may encode an HA protein having an amino acid sequence comprising at least one selected amino acid (e.g., an amino acid mutation) in the HAI subunit of the protein and/or at least one selected amino acid (e.g., amino acid mutation) in the HA2 subunit of the protein. For example, the at least one amino acid mutation in the HA2 subunit may be an asparagine at position 107. Such mutations may also contribute to enhanced growth of the virus during production.

In one embodiment of the invention, the PB1, PB2, PA, NP, and NS gene segments are derived from a single influenza strain. The HA gene segment may be derived from an influenza strain different from the single influenza strain from which the PB1, PB2, PA, NP, and NS gene segments are derived. Likewise, the NA gene segment may be derived from an influenza strain different from the single influenza strain from which the PB1, PB2, PA, NP, and NS gene segments are derived. Accordingly, the influenza virus of the invention may be a pandemic influenza virus (e.g., H5N1, H7N9) or a seasonal influenza virus (e.g., H1N1, H3N2, Influenza B).

(C) Properties of the Influenza Virus

The backbone of the inventive influenza virus confers high growth properties onto influenza viruses, particularly in Vero cells, regardless of the type of influenza virus (e.g., seasonal or pandemic influenza viruses). The inventive influenza virus exhibits high yields even in manufacturing processes using low multiplicity of infection (MOI) (e.g., 0.001). MOI refers to the average number of agent (e.g., virus) per infection target (e.g., cell). A lower MOI is used when multiple cycles of infection are required (e.g., virus vaccine production). Current Good Manufacturing Practice regulations are enforced by the FDA and generally necessitate use of the lowest MOI that still produces high yields of the virus. This is because master seed stocks are costly, and toxicity resulting from noninfectious particles and excess cellular proteins can decrease virus production.

In a further embodiment of the invention, the influenza virus is genetically stable, such that the selected amino acids of the backbone proteins, particularly the PB1, PB2, PA, NP, and NS1 proteins, are highly conserved, even when propagated at low MOI. For example, in one embodiment of the invention, the selected amino acids are conserved in at least one of the PB1, PB2, and NP proteins after at least one, at least two, at least three, at least four, at least five, at least six, at least seven, at least eight, at least nine, at least ten, or more than ten serial passages in a Vero cell line. In one embodiment, the Vero cell line may comprise Vero cells that stably express the M2 ion channel protein of Influenza A virus (i.e., M2VeroA cells). In another embodiment of the invention, the Vero cell line may comprise Vero cells that stably express the BM2 ion channel protein of Influenza B virus (i.e., BM2Vero cells). BM2 is considered to be a functional counterpart to Influenza A virus M2. In such an embodiment, the selected amino acids may be conserved even when the influenza virus is an Influenza A virus.

Genetically modified Vero cells (i.e., those that express influenza M2 or BM2 proteins) behave like normal Vero cells and support growth of Influenza A or B viruses comparable to normal Vero cells. Virus titers for M2SR viruses in M2VeroA cells are comparable to replicating influenza viruses that express functional M2 in unmodified Vero cell lines. Further, virus titers for BM2SR viruses (i.e., influenza viruses that comprise a mutant M gene segment from Influenza B and consequently do not express a functional BM2 protein) in BM2Vero cells are comparable to replicating influenza viruses that express functional BM2 in unmodified Vero cell lines. Accordingly, M2SR and BM2SR viruses behave like replicating influenza viruses in the M2VeroA and BM2Vero cell lines.

In one embodiment of the invention, the influenza virus is capable of replication in human cells.

Method of Generating the Influenza Virus

Also provided herewith is a method of generating an influenza virus, wherein the generated influenza virus comprises PB1, PB2, PA, NP, and NS gene segments that express proteins having selected amino acids, i.e., the recombinant influenza virus of the invention as disclosed herein.

In one embodiment of the inventive method, the method of generating the recombinant influenza virus comprises serially passaging a recombinant influenza virus (e.g., a first influenza virus) in Vero cells to generate the generated influenza virus (e.g., a second influenza virus). The first influenza virus may comprise PB1, PB2, PA, NP, and NS gene segments that express proteins, i.e., PB1, PB2, PA, NP, and NS1 proteins having selected amino acids, as described with respect to the inventive influenza virus. For example, the first influenza virus may comprise a PB1 gene segment encoding a protein, i.e., a PB1 protein, comprising a leucine at position 40, a tryptophan at position 180, an aspartic acid at position 464, and a proline at position 607. The PB2 gene segment of the first influenza virus may encode a protein, i.e., a PB2 protein, comprising a methionine at position 467, a valine at position 504, and an isoleucine at position 529. The PA gene segment of the first influenza virus may encode a protein, i.e., a PA protein, comprising a lysine at position 401. The NP gene segment of the first influenza virus may encode a protein, i.e., an NP protein, comprising a leucine at position 116, a glutamic acid at position 294, and a glutamine at position 311. The NS gene segment of the first influenza virus may encode a protein, i.e., an NS1 protein, comprising proline at position 30 and lysine at position 118. The PB1, PB2, and PA gene segments of the first influenza virus may optionally comprise a uracil at nucleotide position 4. In one embodiment of the invention, the second influenza virus (e.g., the generated influenza virus) is generated after at least four or at least five serial passages of the first influenza virus in Vero cells.

The influenza virus of the invention may also be generated using standard virus rescue techniques. For example, in one embodiment of the invention, one or more plasmids into which cDNAs for each of the eight viral gene segments (i.e., PB1, PB2, PA, NP, M, NS, HA, and NA) are cloned are transfected into eukaryotic host cells, wherein each cDNA sequence is flanked by an RNA polymerase I promoter and an RNA polymerase I terminator (i.e., pPolI plasmids). The gene segments encoding the PB1, PB2, PA, NP, and NS1 and/or NS2 proteins may encode proteins having the selected amino acids of the invention. The gene segment encoding the M2 or BM2 protein may comprise the mutant M2 or BM2 gene segment, such that the gene segment does not encode functional M2 or BM2. The host cell may also be transfected with one or more expression plasmids encoding the viral proteins (e.g., at least one or more of the PA, PB1, PB2, and NP proteins, or at least one or more of the PB1, PB2, PA, NP, M, NS1 and/or NS2, HA, and NA proteins). The eight influenza vRNAs (i.e., gene segments) are then synthesized after transfection of at least one or more plasmids into the host cell. The co-transfected viral polymerases and nucleoproteins assemble the vRNAs into functional vRNPs (i.e., viral ribonucleoprotein complexes) that are replicated and transcribed, ultimately forming the recombinant influenza virus of the invention. This plasmid-based reverse genetics system is further detailed by Neumann et al., *Proc. Natl. Acad. Sci. USA*, 96: 9345-9350 (1999). The influenza virus of the invention may also be generated using other methods known in the art, such as, but not limited to, a ribonucleoprotein (RNP) transfection system, as described in U.S. Pat. No. 9,284,533.

Pharmaceutical Formulation

The invention provides a pharmaceutical formulation (e.g., a vaccine or other immunogenic composition) comprising the inventive influenza virus as described herein.

The pharmaceutical formulation can further comprise at least one pharmaceutically acceptable carrier or excipient. As used herein, the term "pharmaceutically acceptable carrier or excipient" refers to any component of the pharmaceutical formulation other than the inventive influenza virus. The pharmaceutically acceptable carrier or excipient can enhance efficacy of the inventive influenza virus or maintain stability of the pharmaceutical formulation, desirably without significantly inactivating the inventive influenza virus.

The at least one pharmaceutically acceptable carrier or excipient may be any suitable pharmaceutically acceptable carrier or excipient, many of which are known in the art. Exemplary pharmaceutically acceptable carriers or excipients include components that maintain a pH of the pharmaceutical formulation (e.g., buffers), adjust tonicity (e.g., tonicity modifying agents such as an inorganic salt), improve protein (e.g., virus) stability and/or immunogenicity, improve mucoadhesion, prevent protein aggregation, and/or preserve the pharmaceutical formulation (e.g., preservatives). For example, the pharmaceutically acceptable carrier or excipient may comprise at least one of an inorganic salt, surfactant, amino acid, polymer or polymeric compound (e.g., protein, polysaccharide, or hydrogel), chelating agent, sugar, polyol, and/or adjuvant (e.g., any substance that augments a specific immune response), many of which are known in the art. A particular carrier or excipient may serve more than one purpose in the pharmaceutical formulation, and, thus, the following embodiments are not limited to the descriptions recited herein.

Any suitable buffer can be present in the pharmaceutical formulation. In one embodiment, the buffer comprises at least one of an imidazole buffer, a potassium phosphate buffer, phosphate-buffered saline (PBS), dulbecco's phosphate-buffered saline (DPBS) (e.g., 1×DPBS), a histidine buffer, a sodium citrate buffer, and sucrose phosphate glutamate buffer (SPG). PBS and/or DPBS preparations may comprise, for example, sodium chloride, potassium chloride, potassium phosphate monobasic, and sodium phosphate dibasic, and may optionally further comprise calcium chloride and/or magnesium chloride. In some embodiments, the PBS and/or DPBS preparations comprise 136.9 mM sodium chloride, 2.67 mM potassium chloride, 1.47 mM potassium phosphate monobasic, and 8.1 mM sodium phosphate dibasic, although any suitable PBS and/or DPBS preparation, many of which are known in the art, may be used as a buffer in the pharmaceutical formulation.

The buffer can be present in the pharmaceutical formulation in any suitable concentration. The buffer can be present in the pharmaceutical formulation at a concentration of 0.1 mM or more, 1 mM or more, 10 mM or more, 20 mM or more, 30 mM or more, 40 mM or more, 50 mM or more, 60 mM or more, 70 mM or more, 80 mM or more, 90 mM or more, 100 mM or more, 120 mM or more, 140 mM or more, 160 mM or more, 180 mM or more, 200 mM or more, 250 mM or more, 300 mM or more, 350 mM or more, 400 mM or more, 450 mM or more, or 500 mM or more. Alternatively, or in addition, the buffer can be present in the pharmaceutical formulation at a concentration of 1000 mM or less, 500 mM or less, 450 mM or less, 400 mM or less, 350 mM or less, 300 mM or less, 250 mM or less, 200 mM or less, 180 mM or less, 160 mM or less, 140 mM or less, 120 mM or less, 100 mM or less, 90 mM or less, 80 mM or less, 70 mM or less, 60 mM or less, 50 mM or less, 40 mM or less, 30 mM or less, 20 mM or less, 10 mM or less, or 1 mM or less. The buffer can be present in the pharmaceutical formulation at any concentration within a range bounded by any of the aforementioned endpoints. For example, the buffer can be present in the pharmaceutical formulation at a concentration of 0.1 mM to 1000 mM, 0.1 mM to 500 mM, 0.1 mM to 100 mM, 1 mM to 1000 mM, 1 mM to 500 mM, 1 mM to 100 mM, 100 mM to 1000 mM, 100 mM to 500 mM, and the like.

In further embodiments, the buffer is present in the pharmaceutical formulation at a percentage concentration (e.g., volume/volume percentage (% v/v); weight/volume percentage (% w/v); or weight/weight percentage (% w/w)). The buffer can be present in the pharmaceutical formulation at a percentage concentration of 0.1% or more, 1% or more, 5% or more, 10% or more, 15% or more, 20% or more, 30% or more, 40% or more, or 50% or more. Alternatively, or in addition, the buffer can be present in the pharmaceutical formulation at a percentage concentration of 60% or less, 50% or less, 40% or less, 30% or less, 20% or less, 15% or less, 10% or less, 5% or less, or 1% or less. The buffer can be present in the pharmaceutical formulation at any percentage concentration within a range bounded by any of the foregoing endpoints. For example, the buffer can be present in the pharmaceutical formulation at a percentage concentration of 0.1% to 60%, 1% to 60%, 10% to 60%, 0.1% to 50%, 1% to 50%, 10% to 50%, 20% to 60%, 20% to 50%, 20% to 40%, 20% to 30%, 30% to 40%, 40% to 50%, and the like.

The buffer can maintain the pH of the pharmaceutical formulation at any suitable pH. The buffer can maintain the pH of the pharmaceutical formulation at a pH of, for example, 4 or higher, 4.5 or higher, 5 or higher, 5.5 or higher, 6 or higher, 6.5 or higher, 7 or higher, or 7.5 or higher. Alternatively, or in addition, the buffer can maintain the pH of the pharmaceutical formulation at a pH of, for example, 8 or lower, 7.5 or lower, 7 or lower, 6.5 or lower, 6 or lower, 5.5 or lower, 5 or lower, or 4.5 or lower. The buffer can maintain the pH of the pharmaceutical formulation at a pH within a range bounded by any of the foregoing endpoints. For example, the buffer can maintain the pH of the pharmaceutical formulation at a pH of 4 to 8, 4.5 to 8, 5 to 8, 5.5 to 8, 6 to 8, 6.5 to 8, 7 to 8, 7.5 to 8, 4 to 7.5, 5 to 7.5, 6 to 7.5, 7 to 7.5, 4 to 7, 5 to 7, 6 to 7, and the like.

Any suitable tonicity modifying agent can be present in the pharmaceutical formulation. In certain embodiments, one or more inorganic salts are present in the pharmaceutical formulation as tonicity modifying agents. The inorganic salt(s) may be at least one of sodium chloride (NaCl), magnesium sulfate ($MgSO_4$), and magnesium chloride ($MgCl_2$). The tonicity modifying agent, e.g., inorganic salt (s), can be present in the pharmaceutical formulation in any suitable amount. The tonicity modifying agent, e.g., inorganic salt(s), can be present in the pharmaceutical formulation at a concentration of 0.1 mM or more, 0.2 mM or more, 0.4 mM or more, 0.6 mM or more, 0.8 mM or more, 1 mM or more, 1.2 mM or more, 1.4 mM or more 1.6 mM or more, 1.8 mM or more, 2 mM or more, 3 mM or more, 4 mM or more, 5 mM or more, 6 mM or more, 7 mM or more, 8 mM or more, 9 mM or more, 10 mM or more, 20 mM or more, 30 mM or more, 40 mM or more, 50 mM or more, 100 mM or more, 200 mM or more, 300 mM or more, 400 mM or more, 500 mM or more, 600 mM or more, 700 mM or more, 800 mM or more, 900 mM or more, 1000 mM or more, or 1500 mM or more. Alternatively, or in addition, the tonicity modifying agent, e.g., inorganic salt(s), can be present in the pharmaceutical formulation at a concentration of 2000 mM or less, 1500 mM or less, 1000 mM or less, 900 mM or less, 800 mM or less, 700 mM or less, 600 mM or less, 500 mM or less, 450 mM or less, 400 mM or less, 350 mM or less, 300 mM or less, 250 mM or less, 200 mM or less, 150 mM or less, 100 mM or less, 50 mM or less, 45 mM or less, 40 mM or less, 35 mM or less, 30 mM or less, 25 mM or less, 20 mM or less, 10 mM or less, 9 mM or less, 8 mM or less, 7 mM or less, 6 mM or less, 5 mM or less, 4 mM or less, 3 mM or less, 2 mM or less, 1.8 mM or less, 1.6 mM or less, 1.4 mM or less, 1.2 mM or less, 1 mM or less, 0.8 mM or less, 0.6 mM or less, 0.4 mM or less, or 0.2 mM or less. The tonicity modifying agent, e.g., inorganic salt(s), can be present in the pharmaceutical formulation at any concentration within a range bounded by any of the aforementioned endpoints. For example, the tonicity modifying agent, e.g., inorganic salt(s), can be present in the pharmaceutical formulation at a concentration of 0.1 mM to 2000 mM, 0.1 mM to 1500 mM, 0.1 mM to 1000 mM, 0.1 mM to 500 mM, 0.1 mM to 250 mM, 0.1 mM to 100 mM, 0.1 to 50 mM, 0.1 mM to 10 mM, 1 mM to 2000 mM, 1 mM to 1500 mM, 1 mM to 1000 mM, 1 mM to 500 mM, 1 mM to 250 mM, 1 mM to 100 mM, 1 mM to 50 mM, 1 mM to 10 mM, 10 mM to 2000 mM, 10 mM to 1500 mM, 10 mM to 1000 mM, 10 mM to 500 mM, 10 mM to 250 mM, 10 mM to 100 mM, 10 mM to 50 mM, 100 mM to 2000 mM, 100 mM to 1500 mM, 100 mM to 1000 mM, 100 mM to 500 mM, 100 mM to 250 mM, 500 mM to 2000 mM, 500 mM to 1500 mM, 500 mM to 1000 mM, and the like.

In further embodiments, the inorganic salt is present in the pharmaceutical formulation at a percentage concentration (e.g., volume/volume percentage (% v/v); weight/volume percentage (% w/v); or weight/weight percentage (% w/w)). The tonicity modifying agent, e.g., inorganic salt(s), be present in the pharmaceutical formulation at a percentage concentration of 0.1% or more, 1% or more, 2% or more, 3% or more, 4% or more, 5% or more, 6% or more, 7% or more, 8% or more, 9% or more, or 10% or more. Alternatively, or in addition, the tonicity modifying agent, e.g., inorganic salt(s), can be present in the pharmaceutical formulation at a percentage concentration of 10% or less, 9% or less, 8% or less, 7% or less, 6% or less, 5% or less, 4% or less, 3% or less, 2% or less, or 1% or less. The tonicity modifying agent, e.g., inorganic salt(s), can be present in the pharmaceutical formulation at any percentage concentration within a range bounded by any of the foregoing endpoints. For example, the tonicity modifying agent, e.g., inorganic salt (s), can be present in the pharmaceutical formulation at a percentage concentration of 0.1% to 1%, 0.1% to 2%, 0.1% to 5%, 0.1% to 10%, 1% to 2%, 1% to 5%, 1% to 10%, 2% to 10%, 3% to 10%, 4% to 10%, 5% to 10%, and the like.

Any suitable surfactant can be present in the pharmaceutical formulation. In certain embodiments, the surfactant can comprise at least one of polysorbate 20, polysorbate 80, sodium deoxycholate, and poloxamer 188. The surfactant can be present in the pharmaceutical formulation in any suitable amount. In some embodiments, the surfactant is present in the pharmaceutical formulation at a percent concentration (e.g., volume/volume percentage (% v/v); weight/volume percentage (% w/v); or weight/weight percentage (% w/w)). The surfactant can be present in the pharmaceutical formulation at a percentage concentration of 0.01% or more, 0.02% or more, 0.03% or more, 0.04% or more, 0.05% or more, 0.06% or more, 0.07% or more, 0.08% or more, 0.09% or more, 0.1% or more, 0.2% or more, 0.3% or more, 0.4% or more, 0.5% or more, 0.6% or more, 0.7% or more, 0.8% or more, 0.9% or more, or 1% or more. Alternatively, or in addition, the surfactant can be present in the pharmaceutical formulation at a percentage concentration of 1% or less, 0.9% or less, 0.8% or less, 0.7% or less, 0.6% or less, 0.5% or less, 0.4% or less, 0.3% or less, 0.2% or less, or 0.1% or less. The surfactant can be present in the pharmaceutical formulation at any percentage concentration within a range bounded by any of the foregoing endpoints. For example, the surfactant can be present in the pharmaceutical formulation at a percentage concentration of 0.01% to 1%, 0.01% to 0.1%, 0.05% to 1%, 0.05% to 0.1%, 0.1% to 1%, 0.1% to 0.5%, 0.2% to 1%, 0.5% to 1%, and the like.

Any suitable amino acids can be present in the pharmaceutical formulation. In certain embodiments, the amino acid may be one or more of arginine, glutamic acid or glutamate, asparagine, histidine, and glycine. The amino acid(s) can be present in the pharmaceutical formulation in any suitable amount. The amino acid(s) can be present in the pharmaceutical formulation at a concentration of 1 mM or more, 2 mM or more, 3 mM or more, 5 mM or more, 6 mM or more, 7 mM or more, 8 mM or more, 9 mM or more, or 10 mM or more. Alternatively, or in addition, the amino acid(s) can be present in the pharmaceutical formulation at a concentration of about 100 mM or less, 90 mM or less, 80 mM or less, 70 mM or less, 60 mM or less, 50 mM or less, 40 mM or less, 30 mM or less, 20 mM or less, or 10 mM or less. The amino acid(s) can be present in the pharmaceutical formulation at any concentration within a range bounded by any of the foregoing endpoints. For example, the amino acid(s) can be present in the pharmaceutical formulation at a concentration of 1 mM to 10 mM, 1 mM to 50 mM, 1 mM to 100 mM, 5 mM to 50 mM, 10 mM to 50 mM, 20 mM to 50 mM, and the like.

In some embodiments, the amino acid(s) is present in the pharmaceutical formulation at a percentage concentration (e.g., volume/volume percentage (% v/v); weight/volume percentage (% w/v); or weight/weight percentage (% w/w)). The amino acid(s) can be present in the pharmaceutical formulation at a percentage concentration of 0.1% or more, 0.2% or more, 0.3% or more, 0.4% or more, 0.5% or more, 0.6% or more, 0.7% or more, 0.8% or more, 0.9% or more, 1% or more, 2% or more, 3% or more, 4% or more, or 5% or more. Alternatively, or in addition, the amino acid(s) can be present in the pharmaceutical formulation at a percentage concentration of 10% or less, 9% or less, 8% or less, 7% or less, 6% or less, 5% or less, 4% or less, 3% or less, 2% or less, or 1% or less. The amino acid(s) can be present in the pharmaceutical formulation at any percentage concentration within a range bounded by any of the foregoing endpoints.

For example, the amino acid(s) can be present in the pharmaceutical formulation at a percentage concentration of 0.1% to 10%, 0.2% to 10%, 0.5% to 10%, 0.1% to 5%, 0.1% to 2%, 0.2% to 2%, 0.5% to 1%, and the like.

Any suitable polymers or polymeric compounds can be present in the pharmaceutical formulation. The polymer or polymeric compound can be, for example, a protein, a polysaccharide, a hydrogel, or any other suitable polymer or polymeric compound, many of which are known in the art. For example, the polymer or polymeric compound can be recombinant human serum albumin (rHSA), serum albumin (SA), gelatin, hydroxyethyl starch (HES), chitosan, dextran (DEX70K, DEX40K), and polyvinylpyrrolidone (PVP40K).

The polymer(s) or polymeric compound(s) can be present in the pharmaceutical formulation in any suitable amount. The polymer(s) or polymeric compound(s) can be present in the pharmaceutical formulation at a percentage concentration (e.g., volume/volume percentage (% v/v); weight/volume percentage (% w/v); or weight/weight percentage (% w/w)). The polymer(s) or polymeric compound(s) can be present in the pharmaceutical formulation at a percentage concentration of 0.1% or more, 0.2% or more, 0.3% or more, 0.4% or more, 0.5% or more, 0.6% or more, 0.7% or more, 0.8% or more, 0.9% or more, 1% or more, 2% or more, 3% or more, 4% or more, or 5% or more. Alternatively, or in addition, the polymer(s) or polymeric compound(s) can be present in the pharmaceutical formulation at a percentage concentration of 10% or less, 9% or less, 8% or less, 7% or less, 6% or less, 5% or less, 4% or less, 3% or less, 2% or less, or 1% or less. The polymer(s) or polymeric compound(s) can be present in the pharmaceutical formulation at any percentage concentration within a range bounded by any of the foregoing endpoints. For example, the polymer(s) or polymeric compound(s) can be present in the pharmaceutical formulation at a percentage concentration of 0.1% to 10%, 0.2% to 10%, 0.5% to 10%, 0.1% to 5%, 0.1% to 2%, 0.2% to 2%, 0.5 to 2%, 0.1% to 1%, 0.2% to 1%, 0.5% to 1%, and the like.

Any suitable chelating agent can be present in the pharmaceutical formulation. The chelating agent can be, for example, ethylenediaminetetraacetic acid (EDTA), an amidoxime compound (AOX), and/or dithiothreitol (DTT). The chelating agent can be present in the pharmaceutical formulation at any suitable concentration. The chelating agent can be present in the pharmaceutical formulation at a concentration of 10 μM or more, 20 μM or more, 30 μM or more, 40 μM or more, 50 μM or more, 60 μM or more, 70 μM or more, 80 μM or more, 90 μM or more, 100 μM or more, 120 μM or more, or 150 μM or more. Alternatively, or in addition, the chelating agent can be present in the pharmaceutical formulation at a concentration of 500 μM or less, 400 μM or less, 300 μM or less, 200 μM or less, 150 μM or less, 140 μM or less, 130 μM or less, 120 μM or less, 110 μM or less, 100 μM or less, 80 μM or less, 70 μM or less, 60 μM or less, or 50 μM or less. The chelating agent can be present in the pharmaceutical formulation at any concentration within a range bounded by any of the foregoing endpoints. For example, the chelating agent can be present in the pharmaceutical formulation at a concentration of 10 μM to 500 μM, 10 μM to 200 μM, 10 μM to 150 μM, 10 μM to 100 μM, 50 μM to 500 μM, 50 μM to 200 μM, 50 μM to 150 μM, 50 μM to 100 μM, and the like.

Any suitable sugar can be present in the pharmaceutical formulation. The sugar can be, for example, one or more of sucrose, trehalose, mannose, and lactose. The sugar(s) can be present in the pharmaceutical formulation at any suitable concentration. The sugar(s) can be present in the pharmaceutical formulation at a concentration of 0.1 mM or more, 0.2 mM or more, 0.4 mM or more, 0.6 mM or more, 0.8 mM or more, 1 mM or more, 1.2 mM or more 1.4 mM or more 1.6 mM or more 1.8 mM or more, 2 mM or more 3 mM or more 4 mM or more, 5 mM or more, 6 mM or more, 7 mM or more, 8 mM or more, 9 mM or more, 10 mM or more, 20 mM or more, 30 mM or more, 40 mM or more, 50 mM or more, 60 mM or more, 70 mM or more, 80 mM or more, 90 mM or more, or 100 mM or more, 200 mM or more, 300 mM or more, 400 mM or more, 500 mM or more, 600 mM or more, 700 mM or more, 800 mM or more, 900 mM or more, 1000 mM or more, or 1500 mM or more. Alternatively, or in addition, the sugar(s) can be present in the pharmaceutical formulation at a concentration of 2000 mM or less, 1500 mM or less, 1000 mM or less, 900 mM or less, 800 mM or less, 700 mM or less, 600 mM or less, 500 mM or less, 450 mM or less, 400 mM or less, 350 mM or less, 300 mM or less, 250 mM or less, 200 mM or less, 150 mM or less, 100 mM or less, 50 mM or less, 45 mM or less, 40 mM or less, 35 mM or less, 30 mM or less, 25 mM or less, 20 mM or less, 10 mM or less, 9 mM or less, 8 mM or less, 7 mM or less, 6 mM or less, 5 mM or less, 4 mM or less, 3 mM or less, 2 mM or less, 1.8 mM or less, 1.6 mM or less, 1.4 mM or less, 1.2 mM or less, 1 mM or less, 0.8 mM or less, 0.6 mM or less, 0.4 mM or less, or 0.2 mM or less. The sugar(s) can be present in the pharmaceutical formulation at any concentration within a range bounded by any of the foregoing endpoints. For example, the sugar(s) can be present in the pharmaceutical formulation at a concentration of 0.1 mM to 2000 mM, 0.1 mM to 1500 mM, 0.1 mM to 1000 mM, 0.1 mM to 500 mM, 0.1 mM to 250 mM, 0.1 mM to 100 mM, 0.1 to 50 mM, 0.1 mM to 10 mM, 1 mM to 2000 mM, 1 mM to 1500 mM, 1 mM to 1000 mM, 1 mM to 500 mM, 1 mM to 250 mM, 1 mM to 100 mM, 1 mM to 50 mM, 1 mM to 10 mM, 10 mM to 2000 mM, 10 mM to 1500 mM, 10 mM to 1000 mM, 10 mM to 500 mM, 10 mM to 250 mM, 10 mM to 100 mM, 10 mM to 50 mM, 100 mM to 2000 mM, 100 mM to 1500 mM, 100 mM to 1000 mM, 100 mM to 500 mM, 100 mM to 250 mM, 500 mM to 2000 mM, 500 mM to 1500 mM, 500 mM to 1000 mM, and the like.

In other embodiments, the sugar(s) is present in the pharmaceutical formulation at a percentage concentration (e.g., volume/volume percentage (% v/v); weight/volume percentage (% w/v); or weight/weight percentage (% w/w)). The sugar(s) can be present in the pharmaceutical formulation at a percentage concentration of 0.1% or more, 1% or more, 5% or more, 10% or more, 15% or more, 20% or more, 30% or more, 40% or more. Alternatively, or in addition, the sugar(s) can be present in the pharmaceutical formulation at a percentage concentration of 50% or less, 40% or less, 30% or less, 20% or less, 15% or less, 10% or less, 5% or less, or 1% or less. The sugar(s) can be present in the pharmaceutical formulation at any percentage concentration within a range bounded by any of the foregoing endpoints. For example, the sugar(s) can be present in the pharmaceutical formulation at a percentage concentration of 0.1% to 50%, 1% to 50%, 10% to 50%, 0.1% to 20%, 1% to 20%, 10% to 20%, 0.1% to 10%, 1% to 10%, and the like.

Any suitable polyol can be present in the pharmaceutical formulation. The polyol can be, for example, sorbitol and/or mannitol. The polyol can be present in the pharmaceutical formulation at any suitable concentration. The polyol can be present in the pharmaceutical formulation at a concentration of 0.1 mM or more, 1 mM or more, 10 mM or more, 20 mM or more, 30 mM or more, 40 mM or more, 50 mM or more, 60 mM or more, 70 mM or more, 80 mM or more, 90 mM or more, 100 mM or more, 120 mM or more, 140 mM or more, 160 mM or more, 180 mM or more, 200 mM or more, 250 mM or more, 300 mM or more, 350 mM or more, 400 mM or more, 450 mM or more, or 500 mM or more. Alternatively, or in addition, the polyol can be present in the pharmaceutical formulation at a concentration of 1000 mM or less, 500 mM or less, 450 mM or less, 400 mM or less, 350 mM or less, 300 mM or less, 250 mM or less, 200 mM or less, 180 mM or less, 160 mM or less, 140 mM or less, 120 mM or less, 100 mM or less, 90 mM or less, 80 mM or less, 70 mM or less, 60 mM or less, 50 mM or less, 40 mM or less, 30 mM or less, 20 mM or less, 10 mM or less, or 1 mM or less. The polyol can be present in the pharmaceutical formulation at any concentration within a range bounded by any of the foregoing endpoints. For example, the polyol can be present in the pharmaceutical formulation at a concentration of 0.1 mM to 1000 mM, 0.1 mM to 500 mM, 0.1 mM to 100 mM, 1 mM to 1000 mM, 1 mM to 500 mM, 1 mM to 100 mM, 100 mM to 1000 mM, 100 mM to 500 mM, and the like.

In other embodiments, the polyol is present in the pharmaceutical formulation at a percentage concentration (e.g., volume/volume percentage (% v/v); weight/volume percentage (% w/v); or weight/weight percentage (% w/w)). The polyol can be present in the pharmaceutical formulation at a percentage concentration of 0.1% or more, 1% or more, 2% or more, 3% or more, 4% or more, or 5% or more, 10% or more, 15% or more, 20% or more, 25% or more, 30% or more, 35% or more, 40% or more, 45% or more. Alternatively, or in addition, the polyol can be present in the pharmaceutical formulation at a percentage concentration of 50% or less, 45% or less, 40% or less, 35% or less, 30% or less, 25% or less, 20% or less, 15% or less, 10% or less, 5% or less, 4% or less, 3% or less, 2% or less, or 1% or less. The polyol can be present in the pharmaceutical formulation at any percentage concentration within a range bounded by any of the foregoing endpoints. For example, the polyol can be present in the pharmaceutical formulation at a percentage concentration of 0.1% to 50%, 1% to 50%, 5% to 50%, 10% to 50%, 15% to 50%, 0.1% to 25%, 1% to 25%, 5% to 25%, 10% to 25%, 15% to 25%, 0.1% to 15%, 1% to 15%, 5% to 15%, 10% to 15%, 0.1% to 10%, 1% to 10%, 5% to 10%, 0.1% to 5%, 1% to 5%, and the like.

In one embodiment, the pharmaceutical formulation comprises the inventive influenza virus, 0.5 M sucrose, 0.1 M or 0.5 M mannose, 0.3 M or 0.5 M trehalose, 50% SPG, and 0.05% polysorbate-20. In another embodiment, the pharmaceutical formulation comprises the inventive influenza virus, 0.5 M sucrose, 0.3 M trehalose, and 0.05% polysorbate-20.

The at least one pharmaceutically acceptable carrier or excipient can be a component that serves to bind the ingredients of the pharmaceutical formulation (e.g., a binder). The binder may include, but is not limited to, proteins (e.g., gelatin), polymers (e.g., polyethylene glycol, polyvinylpyrrolidone), and/or polysaccharides or derivatives thereof (e.g., starch and cellulose). The at least one pharmaceutically acceptable carrier or excipient can be a component that increases bulk of the pharmaceutical formulation (e.g., a bulking agent, diluent, and/or filler). Such bulking agents may include, but are not limited to, polysaccharides or derivatives thereof, sugars, and/or inorganic compounds. The pharmaceutically acceptable carrier or excipient can be a component that enhances taste and/or appearance of the pharmaceutical formulation (e.g., a flavor, sweetener, and/or color). The pharmaceutically acceptable carrier or excipient can be a component that moisture-proofs the pharmaceutical formulation by absorbing or adsorbing liquids or gases (e.g., a sorbent). A sorbent includes, but is not limited to, starch, calcium phosphate, and/or colloidal silicon dioxide. The pharmaceutically acceptable carrier or excipient can be a component that promotes dissolution of the pharmaceutical formulation (e.g., a disintegrant), such as a starch, cellulose and/or any other polymer known in the art, or derivative thereof (e.g., cross-linked polyvinylpyrrolidone or sodium carboxymethylcellulose).

In some embodiments, the pharmaceutically acceptable carrier or excipient is a component that reduces interparticle adhesion and/or optimizes product flow in and during manufacture of a pharmaceutical formulation (e.g., a glidant). Examples of glidants include, but are not limited to, talc, colloidal silicon dioxide, and corn starch. The pharmaceutically acceptable carrier or excipient can be a component that provides non-sticking properties, such as reducing adhesion between the ingredients and, for example, the punch faces or lubricant in and during manufacture of a pharmaceutical formulation (e.g., an anti-adherent), particularly when the pharmaceutical formulation is formulated as an oral preparation. For example, the anti-adherent may comprise magnesium stearate. In other embodiments, the pharmaceutically acceptable carrier or excipient can be a component that reduces clumping of ingredients and/or reduce friction between, for example, the surface of a pharmaceutical formulation, i.e., formulated as an oral preparation, and the die wall during manufacture (e.g., a lubricant). Both water-soluble or water-insoluble lubricants may be used according to certain embodiments, such as magnesium stearate, stearic acid, vegetable oil, mineral oil, polyethylene glycol, and/or sodium lauryl sulfate. The pharmaceutically acceptable carrier or excipient can be a component that acts as a coating agent. Coating agents include, but are not limited to, gelatin and/or cellulose-based coating agents (e.g., hydroxypropyl methylcellulose).

Other suitable binders, flavors, sweeteners, colors, disintegrants, glidants, anti-adherents, lubricants, and coating agents are well known and readily identifiable in the art.

The pharmaceutical formulation can further comprise a therapeutic agent (e.g., a chemotherapeutic or anti-inflammatory agent). The pharmaceutical formulation can also comprise an agent that triggers an immune response separate from the influenza virus. Such additional components other than the inventive influenza virus can be present in any suitable amount(s).

The additional components can be mixed with the other components to form the pharmaceutical formulation prior to presentation to the immune system. The additional components can also be presented to the immune system separately from the pharmaceutical formulation. For example, the additional components and the pharmaceutical formulation can be presented to the immune system (e.g., administered to an organism) separately. When the additional components and the pharmaceutical formulation are administered separately, the additional components and the pharmaceutical formulation can be administered to the same site of the organism being immunized.

In one embodiment of the pharmaceutical formulation, the pharmaceutical formulation is a virus vaccine. The virus vaccine may be a live, attenuated virus vaccine or an inactivated virus vaccine (e.g., a whole virus vaccine, split virus vaccine, or subunit vaccine). The virus vaccine may be formulated as a monovalent vaccine, a bivalent vaccine, a trivalent vaccine, or a quadrivalent vaccine. For example, the vaccine may comprise multiple embodiments of the inventive influenza virus. In some embodiments, the vaccine may further comprise at least one influenza virus different from the influenza virus of the invention.

The virus vaccine can be formulated into a composition for any suitable means of administration. For example, the virus vaccine can be formulated as an oral preparation (e.g., capsule, tablet, or oral film), a spray (e.g., nasal spray), or any composition suitable for intranasal administration, or parenteral administration, e.g., intravenous, intramuscular, or subcutaneous administration, such as an aqueous or non-aqueous emulsion, solution, or suspension.

Method of Eliciting an Immune Response

The invention provides a method of eliciting an immune response in a mammal comprising administering the inventive influenza virus to the mammal. In one embodiment, the influenza virus comprises a PB1 gene segment, a PB2 gene segment, a PA gene segment, an NP gene segment, and an NS gene segment, encoding proteins, i.e., a PB1 protein, a PB2 protein, a PA protein, an NP protein, and an NS1 protein, respectively, comprising selected amino acids, i.e., the influenza virus of the invention as described herein.

The mammal may be, for example, a human or primate, but is not limited thereto.

In one embodiment of the invention, the inventive influenza virus is administered in a pharmaceutical formulation (e.g., a vaccine or other immunogenic composition), as described herein. The pharmaceutical formulation can be administered intranasally. In another embodiment, the pharmaceutical formulation is administered intramuscularly. The pharmaceutical formulation also can be administered subcutaneously or orally.

The dosing regimen of the pharmaceutical formulation, e.g., the virus vaccine, may depend on the age, weight, sex, and medical history of the mammal. For example, in one embodiment, a single dose of an attenuated virus vaccine to a human can contain about $10^3$, $10^4$, $10^5$, $10^6$, $10^7$, $10^8$, $10^9$, $10^{10}$, $10^{11}$, or $10^{12}$, or any range between two of the foregoing values, particle forming units (PFU), focus forming units (FFU), or TCID50 of the inventive influenza virus. In some embodiments, the regimen for preventing or treating an influenza virus comprises administering the pharmaceutical formulation as a single treatment. The pharmaceutical formulation also can be administered more than once, e.g., the dosing regimen can comprise a booster dosage. For example, the booster dose of the pharmaceutical formulation can be administered over a period ranging from 7 days or more, e.g., 8 days or more, 9 days or more, 10 days or more, 11 days or more, 12 days or more, 13 days or more, 14 days or more, 3 weeks or more, 4 weeks or more, 1 month or more, 2 months or more, 3 months or more, 4 months or more, 5 months or more, 6 months or more, 7 months or more, 8 months or more, 9 months or more, 10 months or more, 11 months or more, 1 year or more, 2 years or more, 3 years or more, 4 years or more, or five years or more, after the initial dose.

EMBODIMENTS

The invention provides the following embodiments:

(1) An influenza virus comprising PB1, PB2, PA, NP, and NS gene segments, wherein (a) the PB1 gene segment encodes a PB1 protein having an amino acid sequence comprising selected amino acids, wherein the selected amino acids comprise a leucine at position 40 and a tryptophan at position 180, and at least one of an asparagine at position 464 or a serine at position 607, and wherein the PB1 gene segment optionally comprises a cytosine to uracil promoter mutation at nucleotide position 4; (b) the PB2 gene segment encodes a PB2 protein having an amino acid sequence comprising selected amino acids, wherein the selected amino acids comprise a valine at position 504, and optionally an isoleucine at position 467 and a valine at position 529, and wherein the PB2 gene segment optionally comprises a cytosine to uracil promoter mutation at nucleotide position 4; (c) the PA gene segment encodes a PA protein having an amino acid sequence comprising selected amino acids, wherein the selected amino acids comprise a lysine at position 401, and wherein the PA gene segment optionally comprises a cytosine to uracil promoter mutation at nucleotide position 4; (d) the NP gene segment encodes an NP protein having an amino acid sequence comprising selected amino acids, wherein the selected amino acids comprise a leucine at position 116, and at least one of a lysine at position 294 or an arginine at position 311; and (e) the NS gene segment encodes an NS1 protein having amino acid sequence comprising selected amino acids, wherein the selected amino acids comprise a proline at position 30 and a lysine at position 118.

(2) The influenza virus of embodiment (1), wherein (a) the PB1 gene segment encodes a PB1 protein having an amino acid sequence comprising selected amino acids, wherein the selected amino acids are a leucine at position 40, a tryptophan at position 180, and an asparagine at position 464, and wherein the PB1 gene segment optionally comprises a cytosine to uracil promoter mutation at nucleotide position 4; (b) the PB2 gene segment encodes a PB2 protein having an amino acid sequence comprising selected amino acids, wherein the selected amino acids are a valine at position 504, and wherein the PB2 gene segment optionally comprises a cytosine to uracil promoter mutation at nucleotide position 4; (c) the NP gene segment encodes an NP protein having an amino acid sequence comprising selected amino acids, wherein the selected amino acids are a leucine at position 116 and a lysine at position 294.

(3) The influenza virus of embodiments (1) or (2), wherein the PB1 gene segment has a nucleotide sequence represented by SEQ ID NO: 2.

(4) The influenza virus of any one of embodiments (1)-(3), wherein the NP gene segment has a nucleotide sequence represented by SEQ ID NO: 1.

(5) The influenza virus of any one of embodiments (1)-(4), wherein the PB1 gene segment encodes a PB1 protein having an amino acid sequence of SEQ ID NO: 7.

(6) The influenza virus of any one of embodiments (1)-(5), wherein the NP gene segment encodes an NP protein having an amino acid sequence of SEQ ID NO: 6.

(7) The influenza virus of any one of embodiments (1)-(6), wherein the selected amino acids are conserved in at least one of the PB1 and NP proteins after at least ten serial passages in a Vero cell line.

(8) The influenza virus of any one of embodiments (1)-(7), wherein the selected amino acids are conserved in at least one of the PB1 and NP proteins after at least ten serial passages in a Vero cell line that stably expresses the M2 ion channel protein of influenza A virus.

(9) The influenza virus of any one of embodiments (1)-(8), wherein the influenza virus is an influenza A virus, and the selected amino acids are conserved in at least one of the PB1 and NP proteins after at least ten serial passages in a Vero cell line that stably expresses the BM2 ion channel protein of influenza B virus.

(10) The influenza virus of embodiment (1), wherein (a) the PB1 gene segment encodes a PB1 protein having an amino acid sequence comprising selected amino acids, wherein the selected amino acids are a leucine at position 40, a tryptophan at position 180, and a serine at position 607 and wherein the PB1 gene segment optionally comprises a cytosine to uracil promoter mutation at nucleotide position 4; (b) the PB2 gene segment encodes a PB2 protein having an amino acid sequence comprising selected amino acids, wherein the selected amino acids are a valine at position 504, an isoleucine at position 467 and a valine at position 529, and wherein the PB2 gene segment optionally comprises a cytosine to uracil promoter mutation at nucleotide position 4; and (c) the NP gene segment encodes an NP protein having an amino acid sequence comprising selected amino acids, wherein the selected amino acids are a leucine at position 116 and an arginine at position 311.

(11) The influenza virus of embodiment (1) or (10), wherein the PB1 gene segment has a nucleotide sequence represented by SEQ ID NO: 4.

(12) The influenza virus of any one of embodiments (1), (10), and (11), wherein the PB2 gene segment has a nucleotide sequence represented by SEQ ID NO: 5.

(13) The influenza virus of any one of embodiments (1) and (10)-(12), wherein the NP gene segment has a nucleotide sequence represented by SEQ ID NO: 3.

(14) The influenza virus of any one of embodiments (1) and (10)-(13), wherein the PB1 gene segment encodes a PB1 protein having an amino acid sequence of SEQ ID NO: 9.

(15) The influenza virus of any one of embodiments (1) and (10)-(14), wherein the PB2 gene segment encodes a PB2 protein having an amino acid sequence of SEQ ID NO: 10.

(16) The influenza virus of any one of embodiments (1) and (10)-(15), wherein the NP gene segment encodes an NP protein having an amino acid sequence of SEQ ID NO: 8.

(17) The influenza virus of any one of embodiments (1) and (10)-(16), wherein the selected amino acids are conserved in at least one of the PB1, PB2, and NP proteins after at least ten serial passages of the virus in a Vero cell line.

(18) The influenza virus of any one of embodiments (1) and (10)-(17), wherein the selected amino acids are conserved in at least the PB1, PB2, and NP proteins after at least ten serial passages in a Vero cell line that stably expresses the M2 ion channel protein of influenza A virus.

(19) The influenza virus of any one of embodiments (1)-(18), wherein at least one of the PB1, PB2, and PA genes segments comprises a cytosine to uracil promoter mutation at nucleotide position 4.

(20) The influenza virus of any one of embodiments (1)-(19), wherein the influenza virus is a recombinant influenza virus.

(21) The influenza virus of any one of embodiments (1)-(20), wherein the virus further comprises an NA gene segment and an HA gene segment.

(22) The influenza virus of embodiment (21), wherein the HA gene segment encodes an HA protein having an amino acid sequence comprising at least one amino acid mutation in HAI.

(23) The influenza virus of embodiment (21) or (22), wherein the HA gene segment encodes an HA protein having an amino acid sequence comprising at least one amino acid mutation in HA2.

(24) The influenza virus of embodiment (23), wherein the at least one amino acid mutation in HA2 is an asparagine at position 107.

(25) The influenza virus of any one of embodiments (21)-(24), wherein the PB1, PB2, PA, NP, and NS gene segments are derived from a single influenza strain.

(26) The influenza virus of embodiment (25), wherein the HA gene segment is derived from an influenza strain different from the single influenza strain from which the PB1, PB2, PA, NP, and NS gene segments are derived.

(27) The influenza virus of embodiment (25) or (26), wherein the NA gene segment is derived from an influenza strain different from the single influenza strain from which the PB1, PB2, PA, NP, and NS gene segments are derived.

(28) The influenza virus of any one of embodiments (1)-(27), further comprising a mutant M gene segment.

(29) The influenza virus of embodiment (28), wherein the influenza virus does not encode a functional M2 protein.

(30) The influenza virus of any one of embodiments (1)-(29), wherein the virus is capable of replication in human cells.

(31) The influenza virus of any one of embodiments (1)-(30), wherein the virus has enhanced growth as compared to an influenza virus that is the same except without the selected amino acids in Vero cells under the same conditions.

(32) A pharmaceutical formulation comprising the influenza virus of any one of embodiments (1)-(32).

(33) The pharmaceutical formulation of embodiment (32), wherein the pharmaceutical formulation is a vaccine.

(34) The pharmaceutical formulation of embodiment (33), wherein the vaccine is formulated as a monovalent vaccine.

(39) The pharmaceutical formulation of embodiment (33), wherein the vaccine is formulated as a bivalent vaccine.

(40) The pharmaceutical formulation of embodiment (33), wherein the vaccine is formulated as a trivalent vaccine.

(41) The pharmaceutical formulation of embodiment (33), wherein the vaccine is formulated as a quadrivalent vaccine.

(42) A method of eliciting an immune response in a mammal, the method comprising administering the influenza virus of any one of embodiments (1)-(31) or the pharmaceutical formulation of any one of embodiments (32)-(41) to the mammal, thereby eliciting an immune response in the mammal.

(43) The method of embodiment (42), wherein the mammal is a human.

(44) A method of generating the influenza virus of any one of embodiments (1)-(31), the method comprising serially passaging an influenza virus in a Vero cell line.

EXAMPLES

The following examples further illustrate the invention but, of course, should not be construed as in any way limiting its scope.

Example 1

This example compares the growth of viruses having different backbones in Vero cells.

The high-yield PR8 ("PR8-HY") backbone described in Ping et al., *Nature Communications,* 6: 8148 (2015), which comprises mutated backbone gene segments derived from influenza A strain A/Puerto Rico/8/1934 ("PR8"), was used to generate M2SR viruses encoding the HA and NA from two different influenza viruses representing two influenza A subtypes that are in seasonal vaccines: A/Massachusetts/15/2013 (MA15; H1N1) and A/Brisbane/10/2007 (Bris10, H3N2).

Specifically, cDNAs encoding the HA and NA gene segments from these viruses were transfected along with cDNAs encoding the PR8-HY backbone gene segments and the M2SR M gene segment (SEQ ID NO: 11). The HA derived from MA15 was Vero-adapted (MA15V), as described in Example 8. The two generated viruses were HY-M2SR-MA15V and Bris10 M2SR-HY. The viruses were generated by standard virus rescue techniques, as described herein, and amplified in MDCK cells that stably express M2 (i.e., M2CK cells).

Influenza A viral RNA (vRNA) segments, i.e., PB1, PB2, PA, NP, NS vRNA segments, and an M vRNA segment lacking the entire M2 open reading frame (ORF), from an influenza PR8-HY backbone, as well as the HA and NA vRNA segments of influenza A/Brisbane/10/2007 (Bris10, H3N2) or A/Massachusetts/15/2013 (MA15V), were cloned into an RNA Polymerase I expression cassette (Sarawar et al., *Vaccine,* 34: 5090-5098 (2016) and Neumann et al., *Proc. Natl. Acad. Sci. USA,* 96: 9345-9350 (1999)). Resulting plasmids were transfected into 293T cells along with viral polymerase subunit and NP expression plasmids, and viruses released into supernatant were amplified in M2CK cells.

The growth of influenza viruses with the PR8-HY backbone and the original high growth ("HG") M2SR backbone (i.e., "the UW-PR8 backbone") also described in Ping et al., *Nature Communications,* 6: 8148 (2015), were compared in M2 Vero cells. To examine the growth of these viruses for comparison, M2VeroA cell monolayers in 6 cm dishes were infected with each virus at an MOI of 0.001 using standard procedures. Infected cells were incubated at 35° C. for 5 days. Aliquots were taken from the supernatant each day, and virus titer was determined by $TCID_{50}$ assay using the Reed and Muench method (Reed & Muench, *Am. J. Hygiene,* 27: 493-497 (1938)).

Figure 1B:
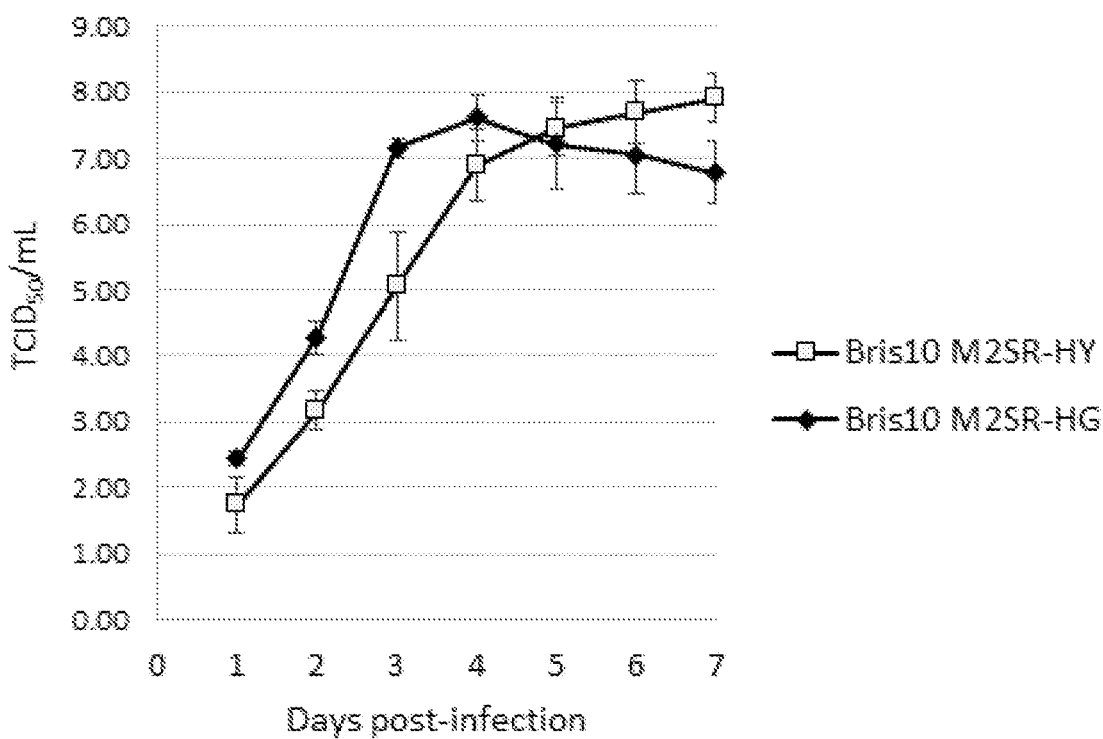
FIG. 1B is a graph of virus titer ($TCID_{50}$/ml) versus time (days post-infection) depicting the growth curve for A/Brisbane/10/2007 M2SR viruses (i.e., Bris10 M2SR) comprising HG and HY backbones in Vero cells.

The results are shown as growth curves in FIG. 1A and FIG. 1B. These results demonstrate that neither HY-M2SR-MA15V nor Bris10 M2SR-HY grew any better than the UW-PR8 backbone in M2VeroA cells, which indicates that the PR8-HY backbone does not enhance viral growth in Vero cells.

Figure 1C:
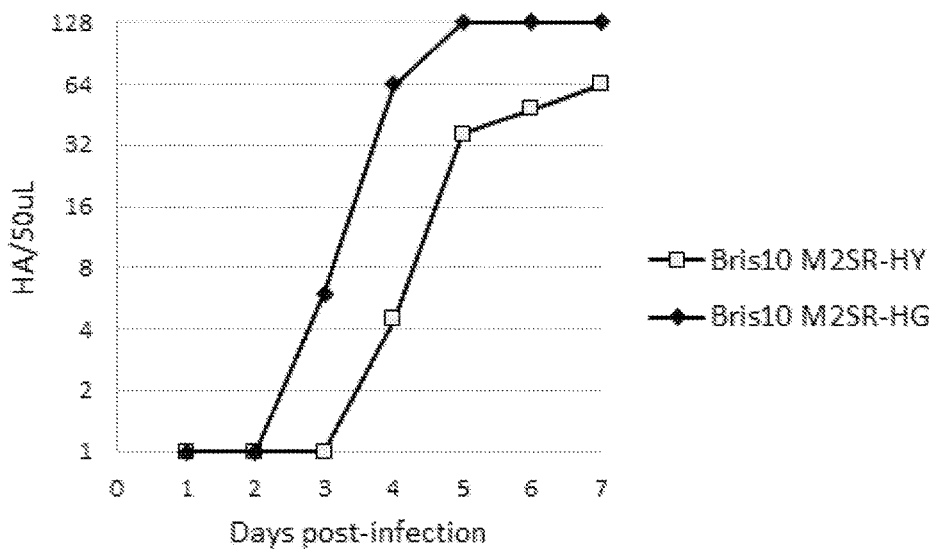
FIG. 1C is a graph of HA titer (HA/50 µl) versus time (days post-infection) for the Bris10 M2SR-HG and Bris10 M2SR-HY viruses in Vero cells.

Since it was observed that the H3N2 viruses (i.e., Bris10 M2SR-HY and Bris10 M2SR-HG) grew to higher titers than the H1N1 viruses (i.e., HY-M2SR-MA15V and HG-M2SR-MA15), the supernatant of the H3N2 viruses was evaluated by hemagglutination (HA) assay to determine if the PR8-HY and UW-PR8 backbones demonstrated differences in the HA titer. As shown in FIG. 1C, the HA titer of the Bris10

M2SR-HY was lower than that of the Bris10 M2SR-HG, further suggesting that the PR8-HY backbone does not enhance viral growth in Vero cells.

To confirm that HY-M2SR-MA15V and Bris10 M2SR-HY were not outliers, but rather were representative of other viruses having the H1N1 and H3N2 subtypes, additional strains were used to generate M2SR viruses with PR8-HY and UW-PR8 backbones. These viruses were then tested for growth using the same method for examining growth of the HY-M2SR-MA15V and Bris10 M2SR-HY viruses described herein. Table 1 recites a summary of all of the strains tested.

TABLE 1

| | | HG (UW-PR8) Backbone v. HY (PR8-HY) Backbone | | | | | |
|---|---|---|---|---|---|---|---|
| Influenza | HA and | | Virus Titer (Log $TCID_{50}$/mL ± SD) | | | | |
| Subtype | NA Strain | Backbone | Day 1 | Day 2 | Day 3 | Day 4 | Day 5 |
| H1N1 | MA15V | HG | 1.50 ± 0.00 | 1.50 ± 0.00 | 1.50 ± 0.00 | 2.12 ± 0.36 | 3.17 ± 0.49 |
| | | HY | 1.50 ± 0.00 | 1.50 ± 0.00 | 1.61 ± 0.08 | 2.22 ± 0.52 | 3.42 ± 0.42 |
| H1N1 | MI45 | HG | 1.50 ± 0.00 | 1.56 ± 0.08 | 1.50 ± 0.00 | 1.50 ± 0.00 | 1.50 ± 0.00 |
| | | HY | 1.56 ± 0.08 | 1.50 ± 0.00 | 1.50 ± 0.00 | 1.56 ± 0.08 | 1.50 ± 0.00 |
| H3N2 | HK4801 | HG | 1.56 ± 0.08 | 2.00 ± 0.41 | 2.00 ± 0.27 | 2.39 ± 0.55 | 3.44 ± 0.34 |
| | | HY | 2.67 ± 0.27 | 3.61 ± 0.28 | 3.72 ± 0.21 | 5.37 ± 0.50 | 6.92 ± 0.42 |
| H3N2 | Bris10 | HG | 2.44 ± 0.08 | 4.28 ± 0.21 | 7.15 ± 0.11 | 7.61 ± 0.28 | 7.22 ± 0.57 |
| | | HY | 1.74 ± 0.34 | 3.17 ± 0.24 | 5.06 ± 0.67 | 6.89 ± 0.44 | 7.45 ± 0.32 |
| H5N1 | avVN1203 | HG | 1.66 ± 0.02 | 2.83 ± 0.24 | 2.89 ± 0.44 | 5.00 ± 0.27 | 7.34 ± 0.47 |
| | | HY | 2.39 ± 0.08 | 3.28 ± 0.34 | 3.60 ± 0.07 | 6.13 ± 0.45 | 8.15 ± 0.46 |

As is apparent from the results presented in Table 1, the PR8-HY backbone does not enhance viral growth in Vero cells as compared to the UW-PR8 backbone for the H1N1, H3N2, and H5N1 virus strains. These results also demonstrate that the PR8-HY backbone is not a suitable backbone for producing influenza vaccines.

Example 2

This example demonstrates the generation of viruses capable of enhanced growth in Vero cells. To generate these viruses, two M2SR viruses comprising either NA and Vero-adapted HA derived from A/Massachusetts/15/2013 (i.e., MA15V M2SR virus) or NA and HA derived from A/California/07/2009 (i.e., CA07 M2SR virus) and comprising the PR8-HY backbone (i.e., HY-M2SR-MA15V and HY-M2SR-CA07) were serially passaged in M2VeroA cells.

The viruses were serially diluted 10-fold and adsorbed onto M2VeroA cells in TC-6 plates using standard influenza virus techniques. However, before virus infection, the cell culture medium was removed, and the cells were washed with PBS. After 60 minutes adsorption at 35° C., virus growth medium containing trypsin/TPCK was added. Cultures were incubated at 35° C. for 4-7 days. Culture supernatant was harvested from the highest dilution well that displayed cytopathic effect and HA activity. Cytopathic effect (CPE) was determined by visual inspection of the monolayer under low power of an optical microscope to detect rounding or other structural changes. HA activity was determined by a standard hemagglutination assay as described in the WHO Manual (*Manual for the laboratory diagnosis and virological surveillance of influenza*, 2011).

Fifty μL of a 0.5% suspension of turkey red blood cells (Innovative Research, Novi, MN) were added to serial 2-fold dilutions of culture supernatant, and then hemagglutination was assessed after 30 min incubation at room temperature. The reciprocal of the highest dilution of culture supernatant that agglutinated the red blood cells was recorded as the HA titer for that sample.

The harvest supernatant was then serially diluted again and used to infect fresh M2VeroA monolayers. The passage history is recited in Table 2.

TABLE 2

| Passage history for HY-M2SR-MA15 and HY-M2SR-CA07 to generate FGHY-1 and FGHY-2 | | | | | | | |
|---|---|---|---|---|---|---|---|
| Passage number in M2VeroA cells | | | P1 60 mm dish, MOI 0.1 | P2 | P3 Serial 10-fold Dilution in TC-6 well plates | P4 | P5 |
| M2SR-HY-CA07 | Harvest Post-infection | Dilution harvested | $10^{-3}$ | $10^{-6}$ | | $10^{-7}$ | $10^{-6}$ |
| | | HA Titer/ 50 μl | 8 | 64 | | >128 | 64 |
| M2SR-HY-MA15V | Harvest Post-infection | Dilution harvested | $10^{-4}$ | $10^{-6}$ | | $10^{-4}$ | $10^{-6}$ |
| | | HA Titer/ 50 μl | 16 | 8 | | 32 | 32 |

As passage number increased, the virus was harvested at higher dilutions, indicating that the virus was growing to higher titers in the Vero cells. Therefore, the process was stopped at passage 5 to evaluate in a growth curve study whether the passage 5 (p5) viruses did indeed grow to higher titers than the starting (p0) viruses.

The p0 viruses and the (p5) viruses were evaluated in growth curves in M2VeroA cells. The (p0) viruses were the HY-M2SR-MA15V and HY-M2SR-CA07 viruses. The (p5) viruses were named the FGHY1-M2SR-MA15V and FGHY2-M2SR-CA07 viruses. FGHY1 and FGHY2 specifically refer to the backbones of the p5 viruses.

Figure 2:
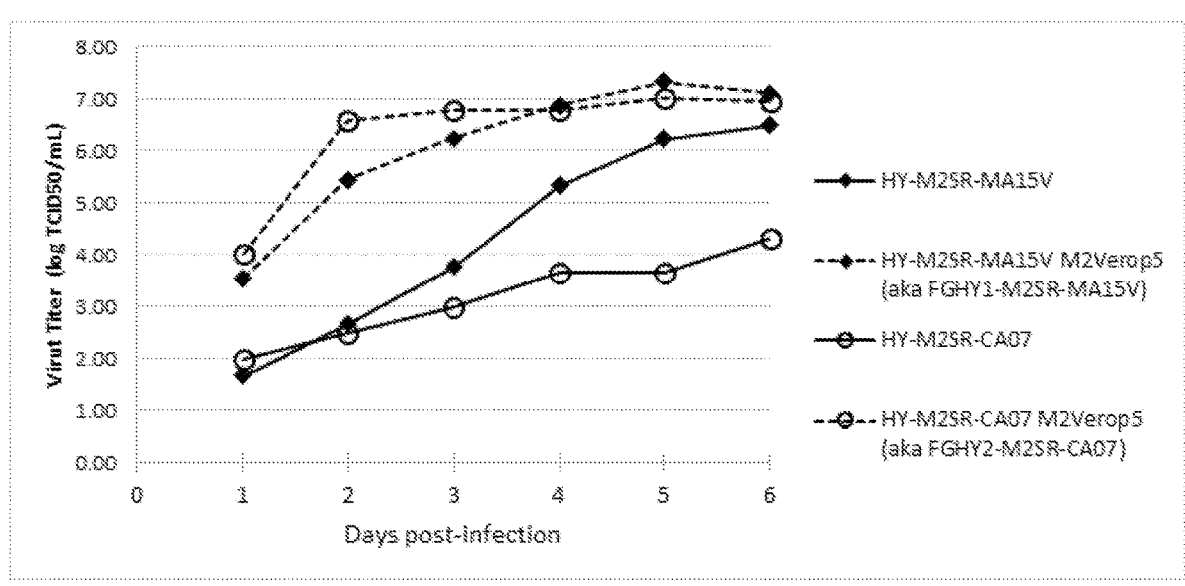
FIG. 2 is a graph of virus titer (log $TCID_{50}$/ml) versus time (days post-infection) depicting the growth curves for FGHY1-M2SR-MA15V and FGHY2-M2SR-CA07 viruses in Vero cells compared to the growth curves of HY-M2SR-MA15V and HY-M2SR-CA07 viruses.

To evaluate the growth curves, cell monolayers were infected at an MOI=0.001 and incubated for 6 days in a 35° C. $CO_2$ incubator. Aliquots were taken daily for virus titer determination using the TCID50 assay. The resulting growth curves are depicted in FIG. 2. As shown by the dashed lines in FIG. 2, the passage 5 (p5) viruses demonstrated higher virus titers and faster growth kinetics than the starting (p0) viruses.

Example 3

This example identifies the mutations that resulted in the increased growth characteristics associated with the passage 5 viruses (i.e., FGHY1-M2SR-MA15V and FGHY2-M2SR-CA07) in the M2VeroA cells of Example 2.

HY-M2SR-MA15V and HY-M2SR-CA07 were serially passaged according to the method of Example 2, and the entire virus genome sequence was determined for passage 6 (p6) viruses, i.e., FGHY1-M2SR-MA15V and FGHY2-M2SR-CA07. Specifically, viral RNA was extracted from supernatant of virus infected cells using a Macherey-Nagel, NU CLEO SPIN (ID RNA extraction kit, and cDNA was generated with a 12 base pair universal primer that amplifies all eight segments of the viral genome in a multi-segment reverse transcription reaction, followed by amplification of the influenza genes using primers as described in Hoffmann et al., *Arch. Virol.*, 146: 2275-2289 (2001). Gene specific primers were used to obtain bulk cDNA sequences. The cDNA sequences obtained were then aligned to the starting plasmid sequences that served as the reference sequences using a sequence comparison algorithm with program parameters designated to highlight non-identical residues. Table 3 shows the amino acid changes that were observed in each of the genes, as compared to the UW-PR8 backbone and the PR8-HY backbone.

As seen in Table 3, the backbones of the FGHY1-M2SR-MA15V and FGHY2-M2SR-CA07 viruses comprise different mutations, such that the FGHY1 and FGHY2 backbones are distinct. For example, FGHY1 comprises mutations in the PB1 protein at amino acid position 464, and the NP protein at amino acid position 294, as compared to the PR8-HY backbone, while FGHY2 comprises mutations in the PB1 protein at amino acid portion 607, the PB2 protein at amino acid positions 467 and 529, and the NP protein at amino acid position 311, as compared to the PR8-HY backbone.

TABLE 3

| | | | | Virus Backbone | |
|---|---|---|---|---|---|
| Viral Protein | Position* | UW-PR8 | PR8-HY | HY-M2SR-MA15V p6 (FGHY1) | HY-M2SR-CA07 p6 (FGYH2) |
| PB1 | nt 4 | C | U | U | U |
| | aa 40 | M | L | L | L |
| | aa 180 | G | W | W | W |
| | aa 464 | D | D | N | D |
| | aa 607 | P | P | P | *S* |
| PB2 | nt 4 | C | U | U | U |
| | aa 504 | I | V | V | V |
| | aa 467 | M | M | M | *I* |
| | aa 529 | I | I | I | *V* |
| PA | nt 4 | C | U | U | U |
| | aa 401 | R | K | K | K |
| NP | aa 116 | I | L | L | L |
| | aa 294 | E | E | *K* | E |
| | aa 311 | Q | Q | Q | *R* |
| NS1 | aa 30 | A | P | P | P |
| | aa 118 | R | K | K | K |

*nt: nucleotide position, aa: amino acid position

FGHY1-M2SR-MA15V and FGHY2-M2SR-CA07 further comprised Vero-adapted mutations in HA2. Specifically, as described in Example 8, FGHY1-M2SR-MA15V comprised a Vero-adapted mutation at position 107 in HA2, wherein the threonine changed to an asparagine. The amino acid sequence of Vero-adapted HA-MA15V is SEQ ID NO: 13. After serial passaging, FGHY2-M2SR-CA07 developed a mutation at position 496 in HA, as indicated in Table 5B.

To confirm that the amino acid changes observed in the FGHY1-M2SR-MA15V and FGHY2-M2SR-CA07 viruses confer high yield properties, FGHY1-M2SR-MA15V and FGHY2-M2SR-MA15V viruses were recreated using the virus rescue techniques described herein.

Specifically, individual backbone genes were cloned into pPolI plasmids using standard molecular techniques known in the art. These genes included the PB1 and NP genes of HY-M2SR-MA15V p6 (i.e., FGHY-PB1 and FGHY1-NP), which are identified by SEQ ID NO: 2 and SEQ ID NO: 1, respectively, and the PB1, PB2, and NP genes of HY-M2SR-CA07 (i.e., FGHY2-PB1, FGHY2-PB2, and FGHY2-NP), identified by SEQ ID NO: 4, SEQ ID NO: 5, and SEQ ID NO: 3, respectively. M2SR viruses were then generated by using plasmid-based influenza virus rescue methods similar to the methods described in Example 1. The viruses further comprised HA-MA15V and NA-MA15.

The generated M2SR viruses (i.e., FGHY1-M2SR-MA15V and FGHY2-M2SR-MA15V) were then assessed for growth kinetics in M2VeroA cells. As comparators, the standard M2SR backbone (UW-PR8) and PR8-HY viruses were used (i.e., HG-M2SR-MA15V and HY-M2SR-MA15V, respectively). M2VeroA cells grown in 6 cm dishes were infected at a multiplicity of infection (MOI) of 0.001. Virus growth medium containing trypsin/TPCK (1 μg/mL) was added, and the cells were incubated at 35° C. for 7 days. Aliquots were taken each day and stored at −80° C. until virus titer determination.

Figure 3:
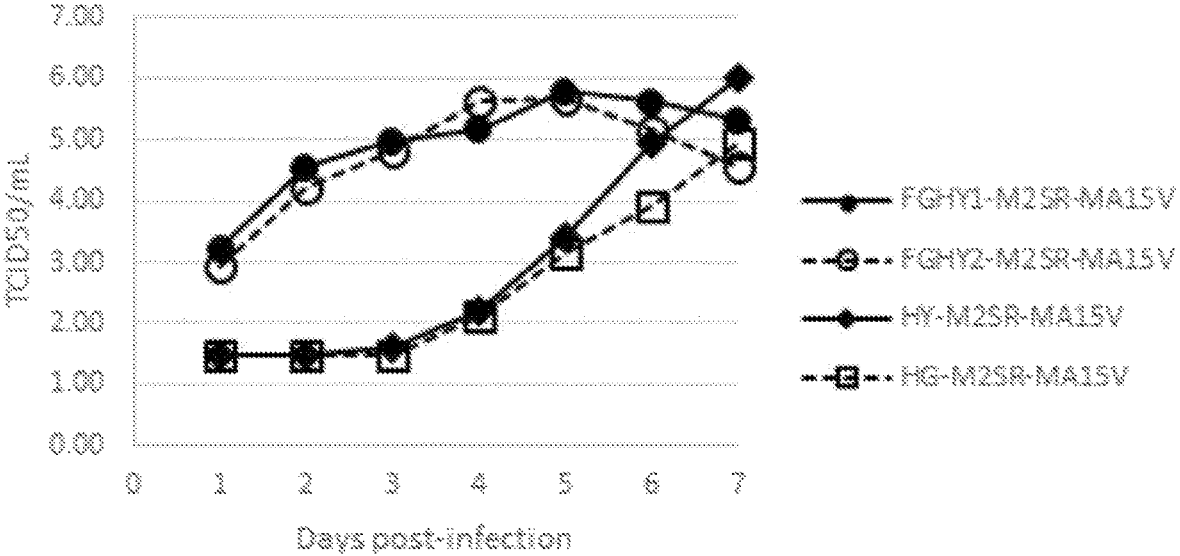
FIG. 3 is a graph of virus titer ($TCID_{50}$/ml) versus time (days post-infection) depicting the growth curves for FGHY1-M2SR-MA15V and FGHY2-M2SR-MA15V viruses in Vero cells compared to the growth curves of HG-M2SR-MA15V and HY-M2SR-MA15V viruses.

The resulting growth curves are depicted in FIG. 3. As shown in FIG. 3, FGHY1-M2SR-MA15V and FGHY2-M2SR-MA15V grew faster than HG-M2SR-MA15V and HY-M2SR-MA15V. FGHY1-M2SR-MA15V and FGHY2-M2SR-MA15V also reached peak titer sooner and plateaued 2-3 days earlier than HG-M2SR-MA15V and HY-M2SR-MA15V. These results indicate that the amino acid mutations found in the passaged viruses (i.e., viruses with the FGHY1 and FGHY2 backbones) confer high-yield characteristics and facilitate infection in M2VeroA cells at a low multiplicity of infection, which is a highly desirable trait in vaccine manufacturing.

Example 4

This example demonstrates that the mutations in the PB1 and NP proteins for FGHY1 and the PB1, PB2, and NP proteins for FGHY2 are responsible for conferring the high growth properties of the influenza viruses, independent of the HA and NA subtypes. Therefore, this example shows that the FGHY1 and FGHY2 backbones can be updated with different influenza HA and NA for seasonal and pandemic influenza vaccine production.

M2SR viruses with seasonal influenza H3N2 HA and NA (A/Brisbane/10/2007) were generated by standard influenza virus rescue techniques described herein. Four M2SR viruses were generated, namely comparators HY-M2SR-Bris10 (PR8-HY backbone) and HG-M2SR-Bris10 (UW-PR8 backbone) in addition to FGHY1-M2SR-Bris10 and FGHY2-M2SR-Bris10. All viruses expressed the H3N2 HA and NA proteins. The HA and NA proteins comprised no Vero-adapted mutations.

Figure 4A:
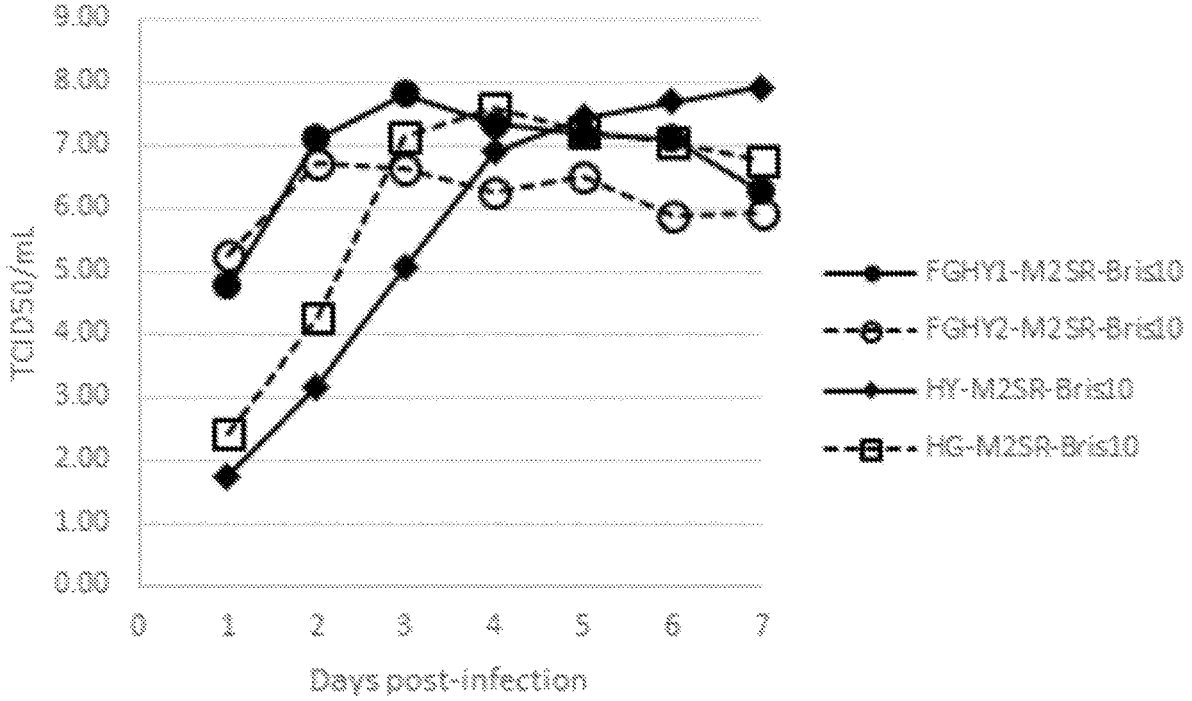
FIG. 4A is a graph of virus titer ($TCID_{50}$/ml) versus time (days post-infection) depicting the growth curves for FGHY1-M2SR-Bris10 and FGHY2-M2SR-Bris10 viruses in Vero cells compared to the growth curves for HY-M2SR-Bris10 and HG-M2SR-Bris10 viruses.
Figure 4B:
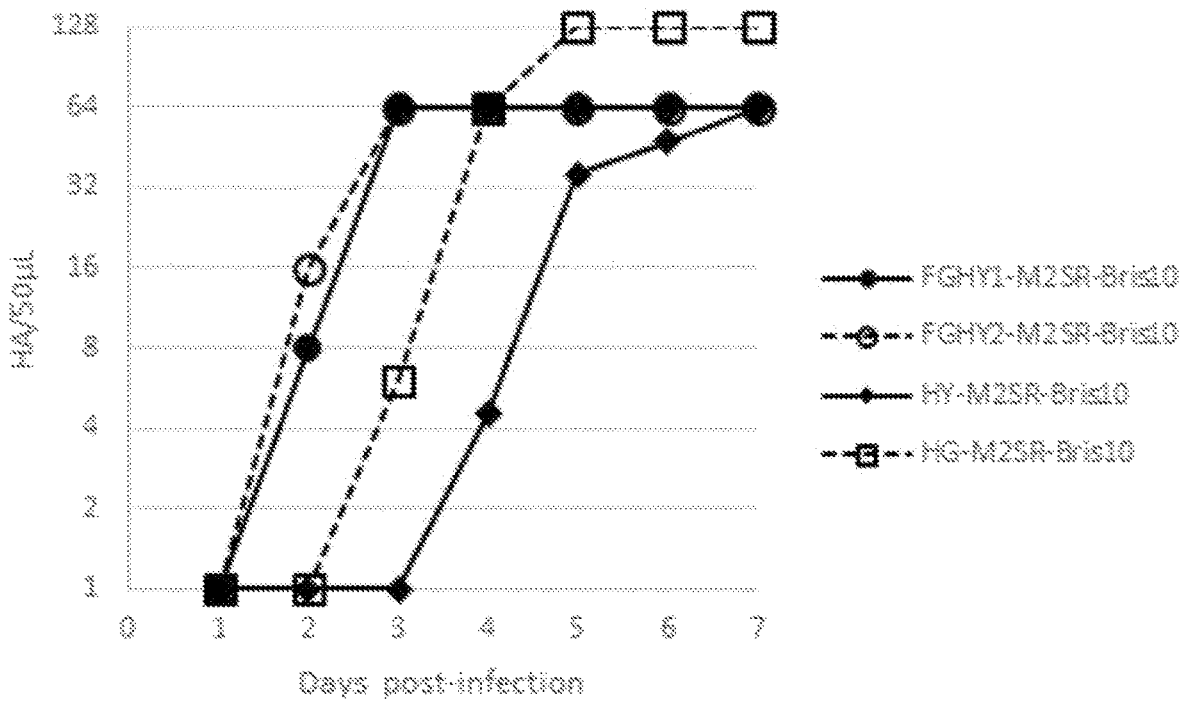
FIG. 4B is a graph of HA titer (HA/50 µl) versus time (days post-infection) for FGHY1-M2SR-Bris10 and FGHY2-M2SR-Bris10 viruses in Vero cells compared to HY-M2SR-Bris10 and HG-M2SR-Bris10 viruses.

Virus growth evaluations were conducted in M2VeroA cells infected at an MOI=0.001. Aliquots were harvested daily, and virus titer was determined by $TCID_{50}$ assay. Supernatants were also evaluated by hemagglutination assay to evaluate HA production. The resulting growth curves are depicted in FIGS. 4A and 4B with respect to virus titers and HA titers, respectively. As shown in FIG. 4A, both FGHY1-M2SR-Bris10 and FGHY2-M2SR-Bris10 grew to higher virus titers sooner than the HY-M2SR-Bris10 and HG-M2SR-Bris10. In addition, as show in FIG. 4B, both FGHY1-M2SR-Bris10 and FGHY2-M2SR-Bris10 demonstrated rapid HA titer kinetics relative to the other two viruses.

These results demonstrate that viruses comprising the FGHY1 and FGHY2 backbones grow faster than the viruses comprising either the UW-PR8 or PR8-HY backbone, independent of the subtype of the HA and NA surface proteins. FGHY1 and FGHY2 backbones enable viruses possessing seasonal influenza A virus HAs and NAs to grow faster in Vero cells for both infectious virus production and HA production (i.e., live or inactivated vaccines). The FGHY1 and FGHY2 backbones also enable viruses possessing pandemic HAs and NAs to grow faster in Vero cells.

M2SR viruses were generated comprising a FGHY1 backbone, as well as HAs and NAs of multiple influenza A subtypes, i.e., seasonal (H1N1, H3N2) and pandemic (H5N1). Growth studies were conducted in M2VeroA cells as described earlier at an MOI=0.001, which compared M2SR viruses comprising the UW-PR8, PR8-HY and FGHY1 backbones. The resulting growth curves are depicted in FIGS. 5A, 5B, and 5C for the H1N1 (MI45), H3N2 (HK4801), and H5N1 (avVN1203) viruses, respectively.

As is apparent from the presented data, the FGHY1 backbone exhibited faster growth kinetics and higher titers, further showing that the FGHY1 backbone provides growth advantages, and indicating that it is suitable to be used for vaccine production.

Figure 5A:
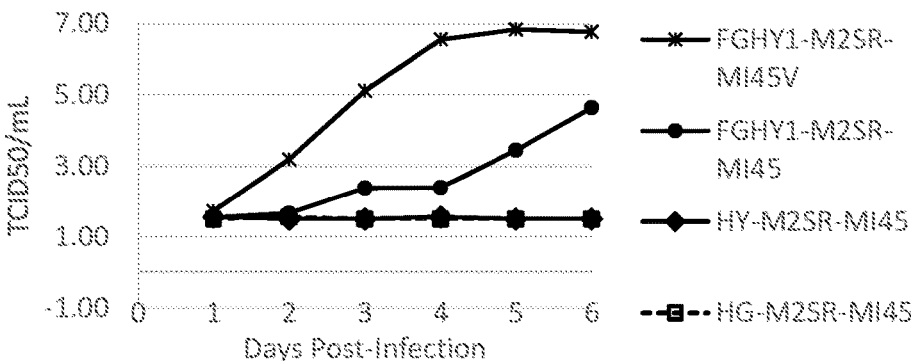
FIG. 5A is a graph of virus titer ($TCID_{50}$/ml) versus time (days post-infection) depicting the growth curve for an A/Michigan/45/2015 M2SR virus comprising a Vero-adapted HA protein and an FGHY1 backbone (i.e., FGHY1-M2SR-MI45V virus) in Vero cells compared to the growth curves for FGHY1-M2SR-MI45, HY-M2SR-MI45, and HG-M2SR-MI45 viruses.
Figure 5B:
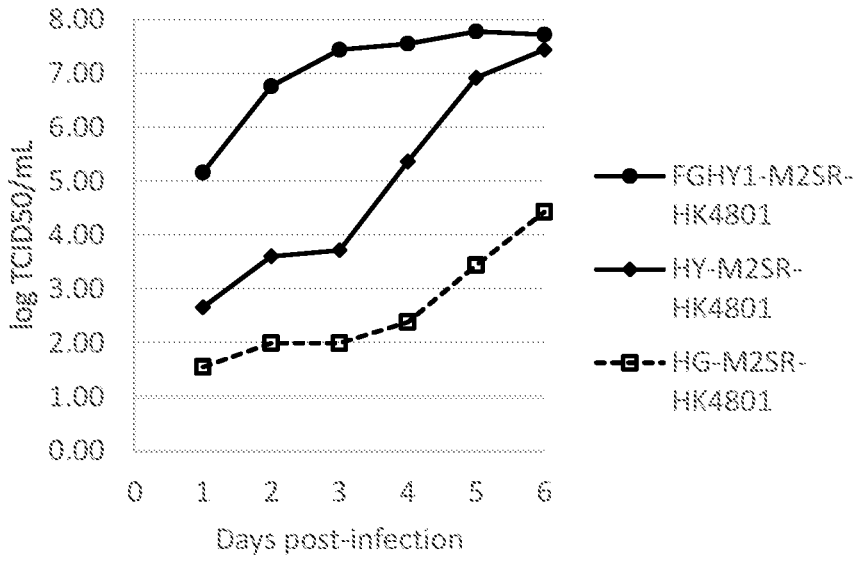
FIG. 5B is a graph of virus titer (log $TCID_{50}/ml$) versus time (days post-infection) depicting the growth curve for an A/Hong Kong/4801/2014 M2SR virus comprising an FGHY1 backbone (i.e., FGHY1-M2SR-HK4801 virus) in Vero cells compared to the growth curves for HY-M2SR-HK4801 and HG-M2SR-HK4801 viruses.
Figure 5C:
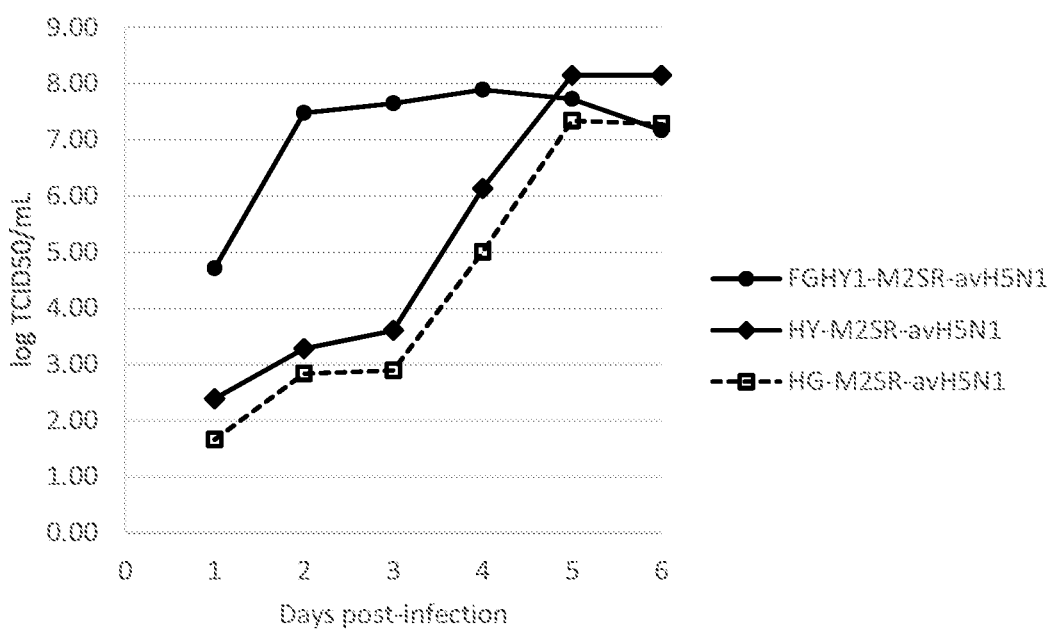
FIG. 5C is a graph of virus titer (log $TCID_{50}/ml$) versus time (days post-infection) depicting the growth curve for an A/Vietnam/1203/04 M2SR virus comprising an FGHY1 backbone (i.e., FGHY1-M2SR-avVN1203 virus) in Vero cells compared to the growth curves for HY-M2SR-avVN1203 and HG-M2SR-avVN1203 viruses.

FIG. 5A further depicts a comparison between a FGHY1-M2SR-MI45 virus and a FGHY1-M2SR-MI45V virus, i.e., a virus further comprising a Vero-adapted mutation at position 107 in HA2, wherein the threonine was changed to an asparagine. Therefore, the results shown in FIG. 5A also demonstrate that a Vero-adapted mutation in the HA protein can further provide enhanced growth effects of the backbone described herein.

Example 5

This example demonstrates that, while viruses comprising the UW-PR8 and HY-PR8 backbones grow in MDCK cells, such viruses exhibit lower growth in Vero cells. Meanwhile, viruses comprising the FGHY1 backbone exhibit higher yields in Vero cells.

Figure 6:
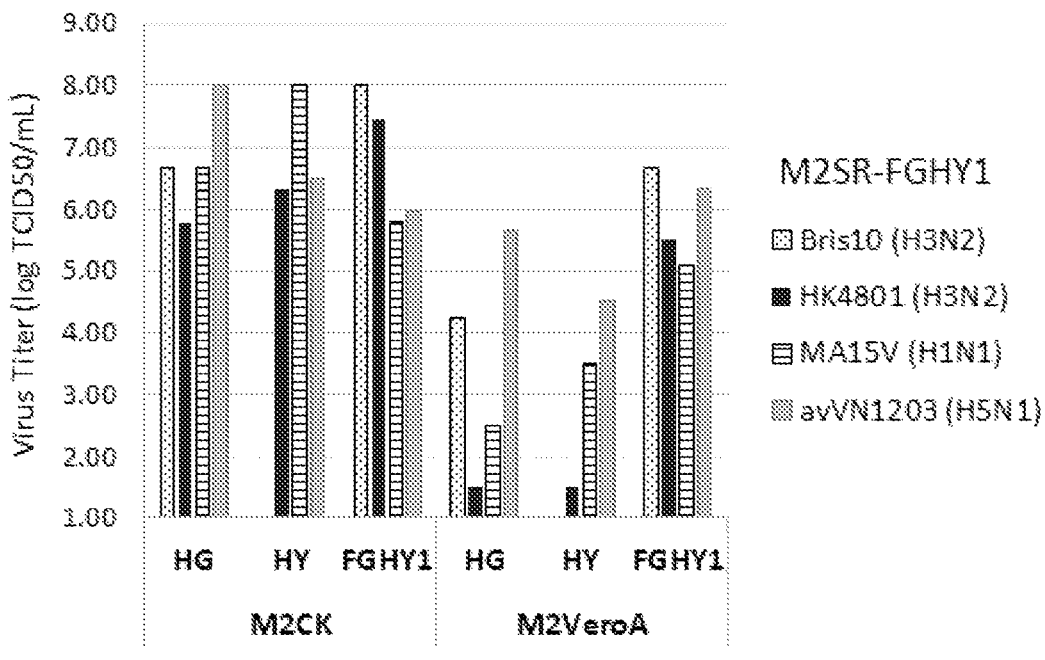
FIG. 6 is a graph depicting virus titer (log $TCID_{50}/ml$) of seasonal and pandemic flu subtype M2SR viruses comprising the HG (i.e., UW-PR8), HY (i.e., PR8-HY), and FGHY1 backbones in M2CK cells and M2VeroA cells.

FIG. 6 depicts virus titers of M2SR viruses (i.e., Bris10 (H3N2), HK4801 (H3N2), MA15V (H1N1), and avVN1203 (H5N1)) comprising different backbones (i.e., UW-PR8, HY-PR8, and FGHY1) grown in M2CK and M2VeroA cells for 4 days. The viruses were generated using standard influenza virus rescue techniques and assessed using methods similar to the methods detailed in Examples 1-4. The data presented in FIG. 6 demonstrates that the FGHY1 backbone specifically supports the growth of seasonal and pandemic flu subtype viruses in Vero cells, as compared to MDCK cells.

Similarly, the data presented in Table 4 demonstrates that FGHY1 enhances growth of multiple subtypes of virus in Vero cells, thereby producing titers closer to the titers produced in MDCK cells.

TABLE 4

| | | Virus Titer (Log $TCID_{50}$/ml) | | Fold Difference |
|---|---|---|---|---|
| HA:NA Subtype | Backbone | M2CK | M2Vero | (log M2CK/M2Vero) |
| Bris10 (H3N2) | HG | 6.67 | 4.23 | 2.44 |
| | HY | Not done | Not done | Not done |
| | FGHY1 | 8 | 6.67 | 1.33 |
| avVN1203 (H5N1) | HG | 8 | 5.67 | 2.33 |
| | HY | 6.5 | 4.5 | 2 |
| | FGHY1 | 5.95 | 6.34 | −0.39 |
| MA15v (H1N1) | HG | 6.67 | 2.5 | 4.17 |
| | HY | 8 | 3.5 | 4.5 |
| | FGHY1 | 5.79 | 5.08 | 0.71 |
| HK4801 (H3N2) | HG | 5.77 | 1.5 | 4.27 |
| | HY | 6.33 | 1.5 | 4.83 |
| | FGHY1 | 7.45 | 5.5 | 1.95 |

*Growth of Virus Subtypes in Vero Cells*

Note:
1.50 log $TCID_{50}$/mL represents virus titer below limit of detection (1.67 log $TCID_{50}$/mL)

These results indicate that the mutations in the FGHY1 backbone overcome the host restrictions in Vero cells, such that Vero cells can behave more like MDCK cells for vaccine production.

Example 6A

This example assesses the genetic stability of the FGHY1 and FGHY2 backbones.

HY-M2SR-MA15 and HY-M2SR-CA07 viruses, generated by the virus rescue techniques described herein, were passaged twice in M2CK cells, and then 20 times and 9 times, respectively, in M2VeroA cells. At each passage, the harvested tissue culture supernatant from the previous passage was serially diluted 10-fold from 1:10 to 1:10,000,000 and used to infect fresh monolayers of M2VeroA cells. Post-infection, the culture supernatant was examined for CPE and HA titer. Supernatant was harvested from the highest dilution that displayed CPE and HA titer anywhere between days 3 and 7 post-infection. FGHY1-M2SR-MA15 and FGHY2-M2SR-CA07 were generated at passage 4 in the Vero cells.

At the end of the passaging, the nucleotide sequences were determined for the entire virus genome and compared to the starting sequence from passage 4 in the Vero cells (i.e., FGHY1-M2SR-MA15 and FGHY2-M2SR-CA07). The results are set forth in Tables 5A and 5B.

TABLE 5A

| | | | | HY-M2SR-MA15 | |
|---|---|---|---|---|---|
| Viral Protein | Position* | UW-PR8 | M2CK p2 | +M2VeroA total P4 (FGHY1) | +M2VeroA total P20 |
| PB1 | nt 4 | C | U | U | U |
| | aa 40 | M | L | L | L |
| | aa 180 | G | W | W | W |
| | aa 464 | D | D | N | N |

TABLE 5A-continued

| | | | | HY-M2SR-MA15 | |
| --- | --- | --- | --- | --- | --- |
| Viral Protein | Position* | UW-PR8 | M2CK p2 | +M2VeroA total P4 (FGHY1) | +M2VeroA total P20 |
| PB2 | nt 4 | C | U | U | U |
| | aa 504 | I | V | V | V |
| PA | nt 4 | C | U | U | U |
| | aa 401 | R | K | K | K |
| NP | aa 116 | I | L | L | L |
| | aa 194 | S | S | S | N |
| | aa 294 | E | E | *K* | *K* |
| NS1 | aa 30 | A | P | P | P |
| | aa 118 | R | K | K | K |
| NA | nt 62 | T | T | T | T/C (silent) |
| | aa 203 | n/a | V | V | A |
| | nt 665 | n/a | T | T | C (silent) |
| | nt 846 | n/a | T | C (silent) | T |
| HA | aa 173 | n/a | N | N | D |
| | aa362 | n/a | V | V | *L* |

TABLE 5B

| | | | | HY-M2SR-CA07 | |
| --- | --- | --- | --- | --- | --- |
| Viral Protein | Position* | UW-PR8 | M2CK p2 | +M2VeroA total P4 (FGHY2) | +M2VeroA total P9 |
| PB1 | nt 4 | C | U | U | U |
| | aa 40 | M | L | L | L |
| | aa 180 | G | W | W | W |
| | aa 607 | P | P | *S* | *S* |
| PB2 | nt 4 | C | U | U | U |
| | aa 504 | I | V | V | V |
| | aa 467 | M | M | *I* | *I* |
| | aa 529 | I | I | *V* | *V* |
| PA | nt 4 | C | U | U | U |
| | aa 401 | R | K | K | K |
| NP | aa 116 | I | L | L | L |
| | aa 311 | Q | Q | *R* | *R* |
| NS1 | aa 30 | A | P | P | P |
| | aa 118 | R | K | K | K |
| NA | aa 136 | n/a | Q | P | P |
| | nt 1379 | n/a | G | G | A (silent) |
| HA | aa 496 | n/a | V | V | L/V |

As is apparent from the results set forth in Table 5A, after 16 additional passages in M2VeroA cells, HY-M2SR-MA15 retained the same amino acid changes in the PB1 and NP proteins. The NP protein acquired one additional mutation at amino acid position 50, namely from a serine to an asparagine. As is apparent from the results set forth in Table 5B, after 5 additional passages in M2VeroA cells, HY-M2SR-CA07 also retained the same mutations in the PB1, PB2, and NP proteins as the starting virus. These results demonstrate that FGHY1-M2SR and FGHY2-M2SR backbones are stable in M2VeroA cells and therefore suitable to use as a vaccine backbone.

Example 6B

To further demonstrate stability of the FGHY1 backbone, Influenza A/Hong Kong/4801/2014 FGHY1 M2SR (H3N2) was serially passaged in BM2Vero cells. BM2Vero cells are Vero cells that express influenza BM2 protein, i.e., the ion channel protein of the influenza B serotype. Strong selective pressures against the A virus interacting with the BM2 protein were expected However, after 13 passages, the virus genome was sequenced. Surprisingly, only silent amino acid mutations were observed. The results, set out in Table 6, further exemplify the stability of the FGHY1 backbone.

TABLE 6

| | | Stability of FGHY1-M2SR-HK4801 Virus in BM2 Vero Cells |
| --- | --- | --- |
| Segment | Gene | M2SR Hong Kong/4801/2014 BM2Vero P13 |
| 1 | PB2 | 2 silent mutations: t795c, t1386c |
| 2 | PB1 | Matches plasmid |
| 3 | PA | 1 silent mutations: t1563c |
| 4 | HA | 1 silent mutations: g750a |
| 5 | NP | Matches plasmid |
| 6 | NA | Matches plasmid |
| 7 | M | Matches plasmid |
| 8 | NS | Matches plasmid |

Example 7

This example demonstrates that an M2SR-FGHY1 virus is capable of replication in human cells, such that enhanced growth in Vero cells is not species-specific.

The original M2SR backbone (UW-PR8) has been tested in human subjects (ClinicalTrials.gov Identifier: NCT02822105) and shown to elicit immune responses indicating that it is functional in human cells. Therefore, the original backbone was used as a comparator to determine whether the M2SR-FGHY1 is capable of replication in human cells and, by extension, viable as a clinical candidate.

The two viruses tested encoded for the HA and NA of the H3N2 influenza virus A/Hong Kong/4801/2014 (HK4801). The two viruses, M2SR-Original-HK4801 (Lot #B17A12YH1) and M2SR-FGHY1-HK4801 (Lot #B17A23YH1), were tested for infection in A549 cells (ATCC CCL-185), which is a human lung epithelial cell line, in 96-well plates using an infected cell NP-enzyme-linked immunosorbent assay (ELISA) protocol as described in WHO influenza manual.

On day 2 post-infection, the cells were stained for intracellular influenza nucleoprotein (NP) with an anti-NP monoclonal antibody and processed as an ELISA to determine TCID50 titer. A standard TCID50 assay was conducted in M2CK cells to obtain virus titers for each virus in order to normalize the A549 titers to the M2CK titers. Table 7 recites the virus titer for each virus in each cell line and the ratio between the two cell lines. The ratio for the two viruses is similar, thereby indicating that the M2SR-FGHY1-HK4801 grows in the human cell line similar to M2SR-Original-HK4801.

TABLE 7

| | Virus Titer ($\log$ TCID$_{50}$/mL) | | Ratio ($\log$ A549/ |
| --- | --- | --- | --- |
| Virus Titer of M2SR-HK4801 Viruses in A549 and M2CK Cells | | | |
| | A549 | M2CK | M2CK Titer) |
| M2SR-Original-HK4801 | 7.33 | 8.43 | −1.1 |
| M2SR-FGHY1-HK4801 | 6.50 | 7.92 | −1.4 |

Example 8

This example demonstrates that passaging wild-type virus in Vero cells may allow for better virus growth by acquiring mutations in the HA gene segment (e.g., the HA2 region of H1N1pdm).

Influenza A/Massachusetts/15/2013(H1N1) (MA15) (e.g., the parent virus) was obtained from International Reagent Resource (IRR, Catalog #FR-1319, Lot #62525202), passaged in Vero cells, and amplified in MDCK cells. Viral RNA in tissue culture supernatants of passage 8 were extracted, and the nucleotide and corresponding amino acid sequences of the HA and NA segments were determined. The HA sequence from passage 8 comprised one amino acid change from the parent virus, which was the amino acid at position 451 (SEQ ID NO: 13) (i.e., position 107 in HA2). Specifically, the threonine changed to an asparagine. Two separate independent passaging from independent wells resulted in the same adaptive mutation.

This Vero-adapted HA2 mutation from MA15 (MA15V) (SEQ ID NO: 13) is similar to the mutation described in Example 4 with respect to the Vero-adapted HA derived from MI45 (MI45V). As evidenced by FIG. 5A, such mutation facilitates virus growth in Vero cells.

Other amino acid changes in HA (e.g., HA2) of Vero passaged influenza HA (e.g., H1N1pdm HA) have been shown to stabilize the HA protein in lower pH, further helping the virus with infection into Vero cells. See, for example, Cotter, Jin, and Chen, *PLoS Pathog*, 10(1): e1003831 (2014); Maurer-Stroh et al., *PLoS Curr*, 2: RRN1162 (2010); and Russier et al., *PNAS*, 113(6): 1636-1641 (2016). Therefore, the HA mutations describe herein may also affect HA protein stability in lower pH.

FIG. 7A is a table that depicts mutations in the amino acid sequences of the HA protein in H1N1 viruses that have emerged during Vero adaptations. Specifically, Table 7A depicts the Vero-adapted mutations from the MA15V (2013 Mass 15) and M145V (2015 MI45) described herein. The table of FIG. 7A further depicts Vero-adapted HA derived from influenza viruses passaged 6 times in Vero cells, i.e., A/Slovenia/2903/2015 (2015 Slovenia), A/Lisboa/32/2015 (2015 Lisboa), A/Scotland/P2/2015 (2015 Scotland), and A/Montana/50/2016 (2016 Montana 50).

FIG. 7B is a table that depicts mutations in the nucleic acid sequence and the consequent mutations in the amino acid sequence of the Vero-adapted HA derived from an H3N2 virus (i.e., A/Singapore/INFIMI-1-16-0019/2016). As evidenced by the table of FIG. 7B, the possible amino acid mutations for each HA set out therein are as follows: T176K, L210P, T2191, S221P, D241G, P243H, K407E, D435N, E459K, and/or R472G. The "Clinical" HA correlates to the wild-type HA. The HA names V1 through V8 correlate with the different HA sequences obtained with various passages. The shaded boxes indicate a nucleotide mutation that results in an amino acid mutation. The source column describes the passage history of the starting virus.

Figure 7C:
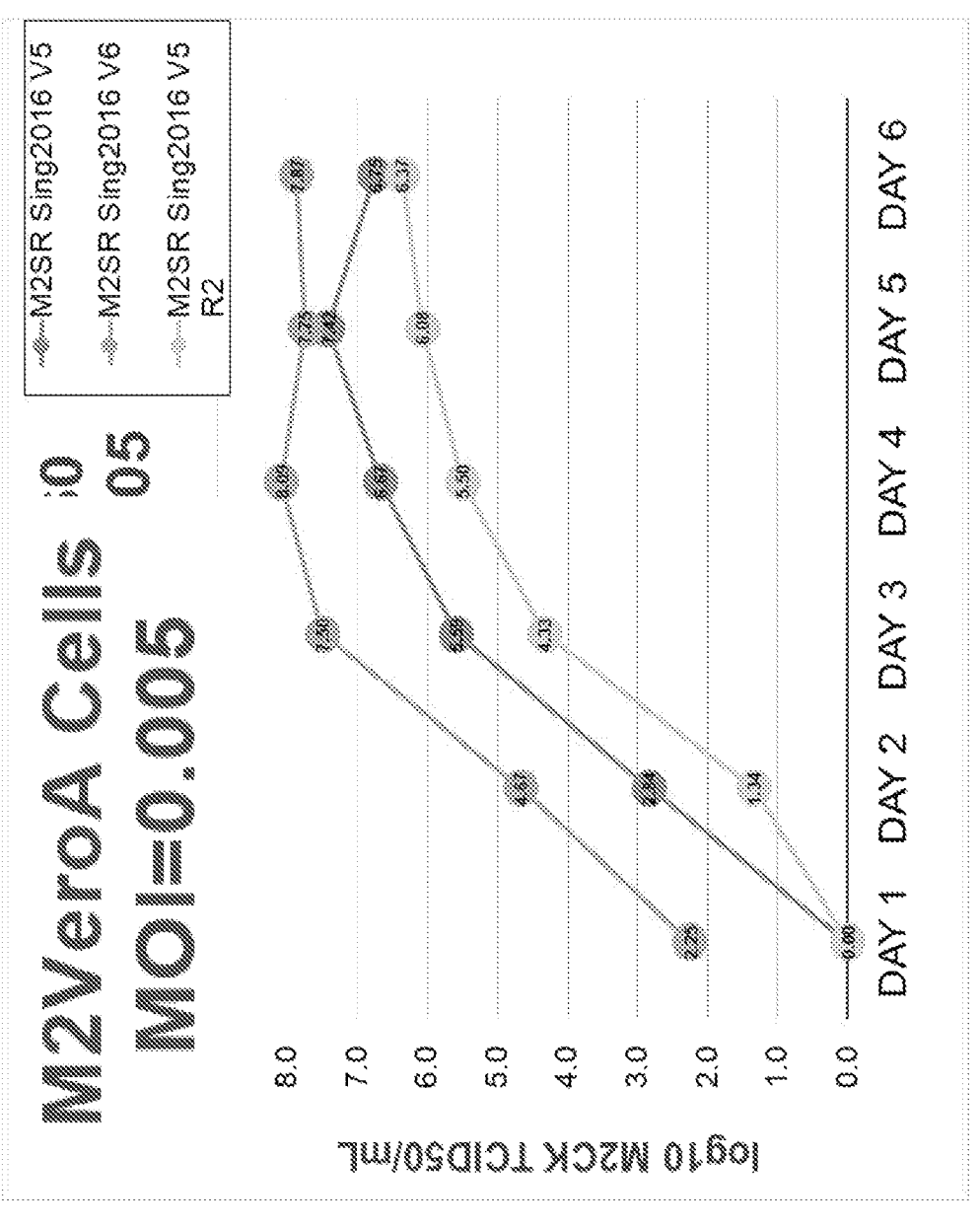
FIG. 7C is a graph of virus titer ($\log_{10}$ M2CK $TCID_{50}/ml$) versus time (days post-infection) depicting the growth curves for A/Singapore/INFIMH-16-0019/2016 M2SR viruses (i.e., M2SR Sing2016 viruses) comprising different Vero-adapted HA mutations.

FIG. 7C depicts the growth curves of M2SR Sing2016 viruses comprising different HA mutations, as shown in FIG. 7B (i.e., M2SR Sing2016 V5, M2SR Sing2016 V5 R2, and M2SR Sing2016 V6), in M2VeroA cells. These viruses also comprised the FGHY1 backbone. M2VeroA cell monolayers were infected with each virus at an MOI of 0.005. Infectious supernatants were collected at the indicated time-points, and virus titer was determined by $TCID_{50}$ assay in M2CK cells. The M2SR Sing2016 having the most Vero-adapted mutations (i.e., M2SR Sing2016 V6) exhibited the highest growth.

Example 9

This example demonstrates that FGHY1-M2SR viruses are attenuated in vivo.

Seven-week-old BALB/c, female mice were immunized intranasally with one of the following viral mutants: H1N1 FGHY1-M2SR, H3N2 FGHY1-M2SR (both of which contained the mutant M segment as set forth in SEQ ID NO: 11). These mutants were administered at a dose of $1 \times 10^6$ $TCID_{50}$ per mouse. A control group of mice were given SPG. The mice were observed for 14 days after immunization for any change in body weight and symptoms of infection.

Figure 10:
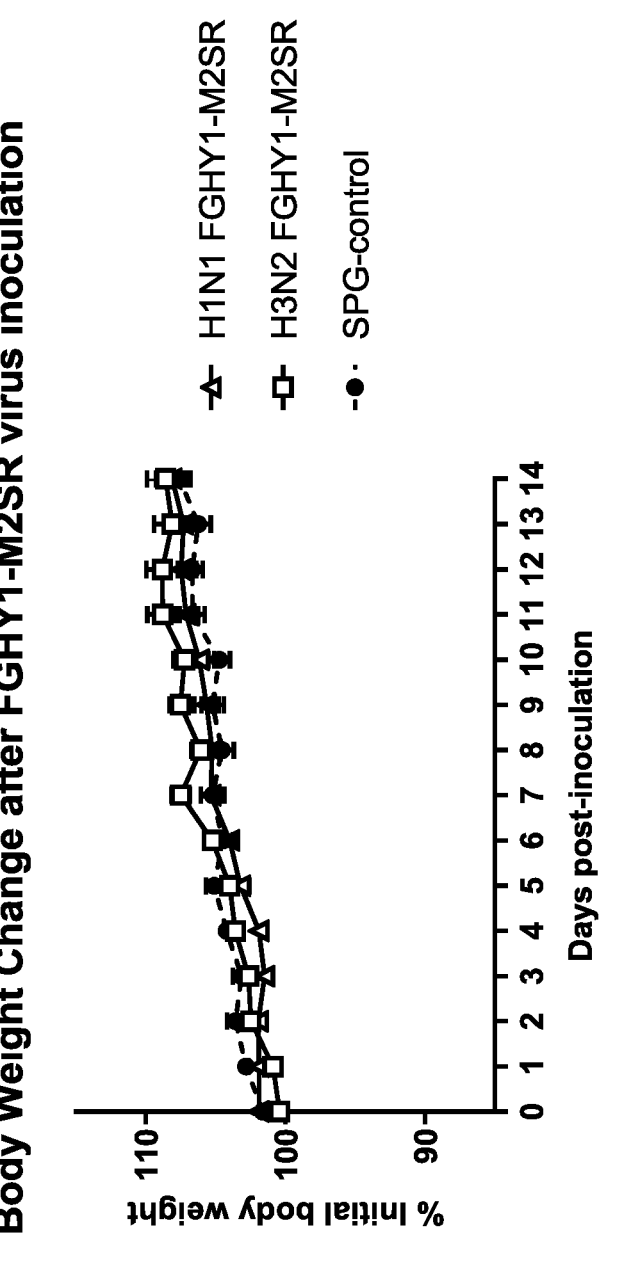
FIG. 10 is a graph depicting the mouse percent body weight change after inoculation with FGHY1-M2SR mutants versus time (days post-infection). Mean % body weights of groups with standard error of the mean are shown.

No clinical symptoms of infection or body weight loss were observed in mice immunized with the FGHY1-M2SR mutants or SPG control over the 14-day period FIG. 10 depicts the mouse percent body weight change after immunization. Moreover, the change in body weight between the groups was comparable over the 14-day period. These results indicate that the FGHY1-M2SR viruses are attenuated and not pathogenic in mice.

Example 10

A backbone that confers growth advantages in cells from one species may be expected to display host restriction and not replicate and/or produce antigen in the target host. However, this example demonstrates that the antigen production of FGHY1-M2SR viruses is not restricted in human cell lines.

The following human cell lines were tested: A549 (ATCC#CCL-185) human lung carcinoma; Calu-3 (ATCC#HTB-55) human lung adenocarcinoma; and MRC-5 (ATCC#CCL-171) human lung fibroblast. These cell lines are from the human respiratory tract and represent the target substrate for an influenza vaccine virus. Control cell lines used for growth of influenza viruses were MDCK (Sigma#84121903) cells and Vero (ATCC#CCL-81) cells.

Cells were seeded in 60 mm dishes one day before infection and were immunized with an approximate MOI=0.5 of the following viruses: Ori indicating UW-PR8 ("HG") backbone, FGHY1, and IVR-147, a replicating vaccine reassortant virus from CDC comprising backbone gene segments from A/Puerto Rico/8/1934. All of these viruses expressed the HA and NA from A/Brisbane/10/2007. A subset of cells were infected with viruses comprising Ori and FGHY1 expressing the HA and NA from A/Singapore/INFIMH-16-0019/2016. The culture medium was supplemented with 10% FCS for 1 or 2 days after virus infection at 35° C. Cells in the culture medium and on the culture surface were harvested and fixed with 10% buffered formalin. Cells were permeabilized in BD Cytofix/Cytoperm solution (BD, Cat #554714) and influenza NP protein was stained by FITC labeled anti-influenza A NP mouse monoclonal antibody (D67J, Invitrogen, Cat #MA1-7322). Fluorescein intensity was measured by BD LSRII and analyzed by FlowJo software.

Single cell population was gated on a forward scatter height (FSC-H) versus forward scatter area (FSC-A), and FITC positive and negative cells were separated on a side scatter area (SSC-A) versus FITC. FITC positive cells are considered virus infected cells and strength of FITC intensity reflects amount of NP expression in the cell.

The resulting NP expression level data are presented in FIGS. 8A, 8B, 9A, and 9B.

Figure 8A:
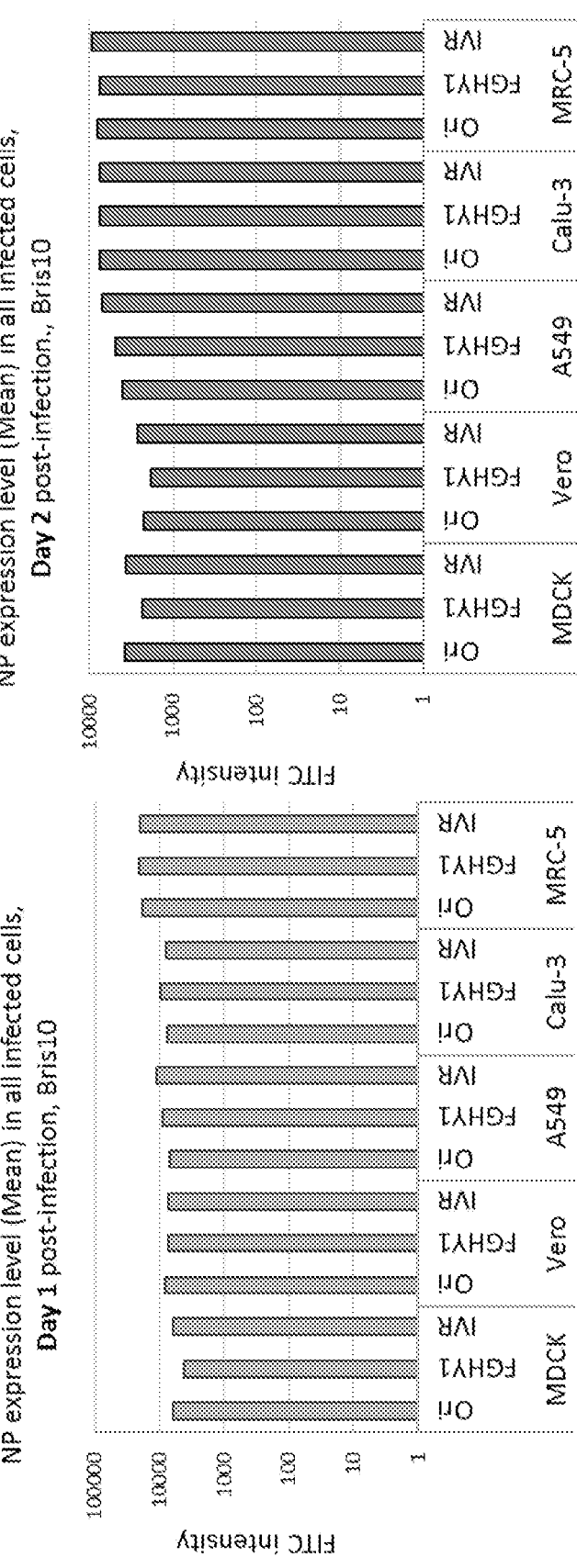
FIG. 8A depicts NP antigen production (i.e., NP expression levels) for viruses having different backbones (i.e., FGHY1, UW-PR8 ("HG"), and IVR-147) and comprising HA and NA from A/Brisbane/10/2007 (i.e., Bris10 viruses) in human cell lines, i.e., A549, MRC-5 and CALU, on Day 1 and Day 2 post-infection.
Figure 8B:
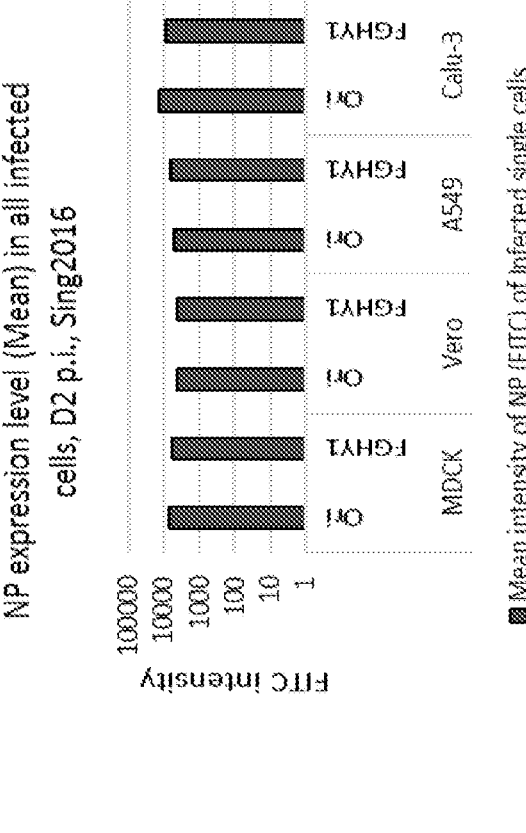
FIG. 8B depicts NP antigen production (i.e., NP expression levels) for viruses having different backbones (i.e., FGHY1, UW-PR8 ("HG")) and comprising HA and NA from A/Singapore/INFIMH-16-0019/2016 (i.e., Sing2016 viruses) in human cell lines, i.e., A549, MRC-5 and CALU, on Day 1 and Day 2 post-infection.

FIGS. 8A and 8B show that the FGHY1 viruses express similar levels of NP in the different cell lines as compared to the IVR-147 or HG viruses.

Figure 9A:
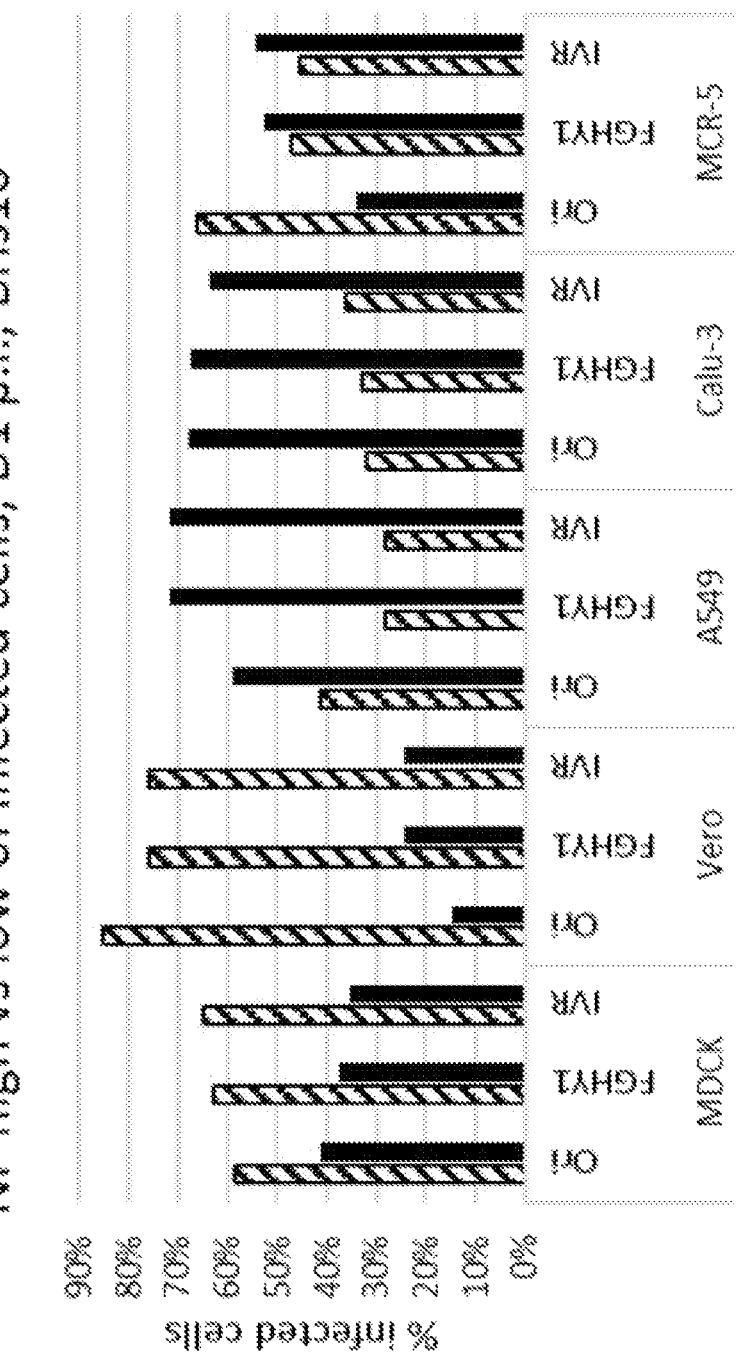
FIG. 9A depicts the proportion of cells expressing high NP levels to cells expressing low NP levels in different cell lines after infection with Bris10 viruses having different backbones (i.e., FGHY1, UW-PR8 ("HG"), and IVR-147) on Day 1 post-infection.
Figure 9B:
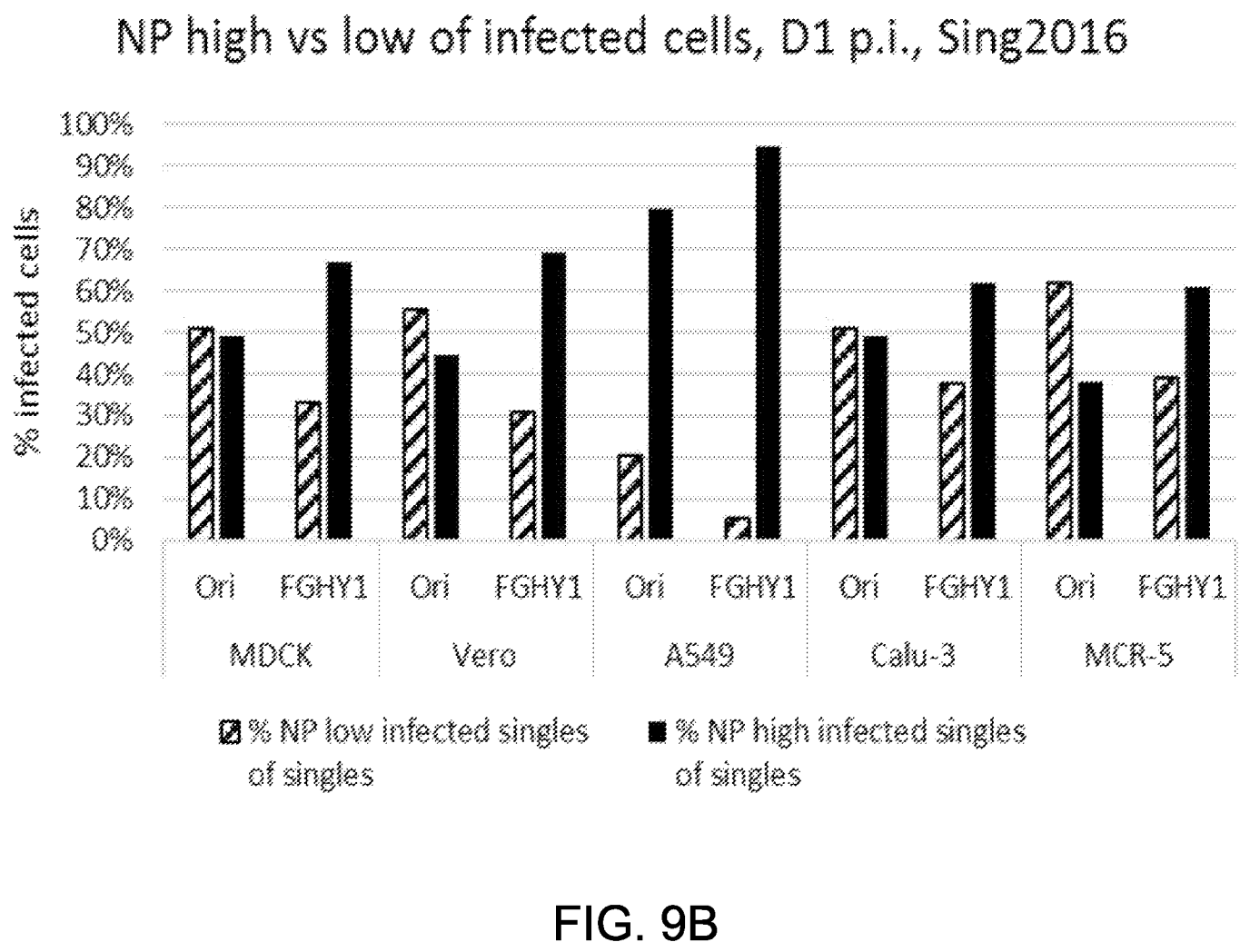

FIGS. 9A and 9B show that the FGHY1-M2SR viruses have similar or higher proportions of cells expressing high NP levels in the human cell lines compared to the other viruses. These results demonstrate that the FGHY1 viruses can infect human cell lines and produce influenza antigens. Therefore, FGHY1-M2SR viruses are expected to induce immunity when administered to human subjects.

Example 11

This example demonstrates that the FGHY1-M2SR vaccine elicits antibody responses in vivo that are increased upon repeat dosing with no toxicity to the host.

A. Summary

To demonstrate that the FGHY1-M2SR vaccine virus elicits immune responses against the component without causing toxicity to the host, 15 male and 15 female ferrets were immunized intranasally with the FGHY1-M2SR vaccine at a dose level of $1 \times 10^8$ $TCID_{50}$ (low dose) or $1 \times 10^9$ $TCID_{50}$ (high dose). A third group of ferrets was mock immunized intranasally with SPG as a placebo control. A three-dose vaccination regimen was utilized for each treatment group. Ferrets were administered the prime immunization (study day 1) and the 2 boost immunizations 13 and 27 days later (study days 14 and 28). Following each immunization, ferrets were observed for 7 days for mortality, with body weights, body temperatures and clinical signs measured daily. Blood was collected to assess clinical pathology pre-study and on study days 14, 16, 30, and 49 from all surviving ferrets. Serum samples were collected pre-study, and on study days 14, 30, and 49 to evaluate antibody levels over time by ELISA, hemagglunination inhibition (HAI) assay, and virus neutralization (VN) assay. Necropsy was performed on 5 males and 5 females per group on study days 3, 30, and 49, including examination of the external surface of the body, all orifices, the cranial, thoracic and peritoneal cavities, and their contents.

B. Materials and Methods

Vaccine Virus Immunization. Ferrets were immunized intranasally with three doses of an H3N2 FGHY1-M2SR vaccine at either a dose of $1 \times 10^8$ $TCID_{50}$ or a dose of $1 \times 10^9$ $TCID_{50}$. Vials of frozen vaccine virus stock were thawed at room temperature for at least 10 minutes and then stored refrigerated, or on wet ice, until use. Ferrets were anesthetized with ketamine/xylazine and the virus dose administered intranasally in a volume of 500 µL (250 µL per nare).

The H3N2 FGHY1-M2SR vaccine virus is a recombinant influenza A virus that does not express a functional M2 protein, encoding the HA and NA genes of Influenza A/Singapore/INFIMI-I-16-0019/2016 (H3N2). The M gene segment of the influenza A virus is represented by SEQ ID NO: 11.

Experimental Design. Ninety (90) ferrets (Triple F Farms, Sayre PA), 45 males and 45 females, 16 to 22 weeks old at the time of study initiation, were utilized for the study. All animal procedures were performed in an animal biosafety level-2 facility in accordance with the protocols approved by the animal care and use committee at IIT Research Institute. Prior to immunization, ferrets were monitored for 4 days to establish baseline body temperatures. Temperature readings were recorded daily through a transponder (BioMedic data systems, Seaford, DE) implanted subcutaneously in each ferret. Blood was collected prior to study initiation, and serum tested for influenza antibodies. Pre-immunization serum samples were treated with receptor destroying enzyme (RDE) (Denka Seiken, Tokyo, Japan) to remove nonspecific inhibitors, then serially diluted, tested against a defined amount of influenza A/Michigan/45/2015 (H1N1), A/Singapore/INFIMI-I-16-0019/2016 (H3N2), B/Phuket/3073/2013 (Yamagata lineage), and B/Colorado/06/2017 (Victoria lineage) viruses and mixed with 0.5% turkey red blood cells. Antibody titers were defined by the lowest serum dilution causing inhibition of red blood cell agglutination. Only ferrets with HAI titers less than 40 were considered seronegative and used in this study. Study animals were randomized and divided into 3 groups (15 male and 15 female ferrets/group).

To assess the vaccine efficacy and toxicity, ferrets were immunized intranasally with three doses of $1 \times 10^8$ $TCID_{50}$ or three doses of $1 \times 10^9$ $TCID_{50}$ of the H3N2 FGHY1-M2SR on study days 1, 14, and 28. The control group was mock immunized intranasally with SPG on study days 1, 14, and 28. Ferret body temperatures, weights, and clinical symptoms were monitored daily for 7 days post-immunizations. Blood was collected to assess clinical pathology on study days −5, 14, 16, 30, and 49 from all surviving ferrets. Serum samples were collected on study days −5, 14, 30, and 49 and kept at approximately −70° C. until measurement of antibody titer by ELISA, virus neutralization assay and HAI assay. All study animals were euthanized on their scheduled dates (Day 3, 30, or 49, 5 males and 5 females per group) and necropsied. Necropsy consisted of examination of the external surface of the body, all orifices, and the cranial, thoracic and peritoneal cavities and their contents. The tissues were collected, fixed, and evaluated histopathologically by a board-certified veterinary pathologist.

C. Results

Moribundity/Mortality and Clinical Observations: All ferrets survived until their scheduled date of sacrifice. The most common clinical sign observed in groups that received H3N2 FGHY1-M2SR was diarrhea; however, animals in the SPG control group also exhibited diarrhea. All ferrets had an activity level score of "0" (alert and playful) for all time points measured during Days 1-49, except for one male and one female from the SPG control group that were given a score of "1" (alert, but playful only when stimulated) on Day 20.

Body Weights and Body Weight Changes: Although statistically significant differences in mean body weight change compared to the SPG control occurred in some groups, these differences appeared to be distributed randomly and were unremarkable.

Body Temperatures: Although statistically significant increase and decrease in mean body temperature in comparison to the SPG control group occurred in some groups, these differences appeared to be distributed randomly and were unremarkable.

Enzyme-linked immunosorbent assay (ELISA): Anti-HA IgG antibody titers from serum samples were determined by ELISA. ELISA plates were coated by recombinant HA protein from A/Singapore/INFIMI-1-16-0019/2016 (H3N2) (Immune Technology Corp., New York, NY), blocked by skim milk, and samples were applied. Ferret IgG antibodies were detected by horseradish peroxidase labeled anti-ferret IgG goat antibodies (SeraCare Life Sciences, Milford, MA) and 1-Step™ Ultra TMB-ELISA (Thermo Fisher Scientific Inc., Maltham, MA) substrate.

Figure 11:
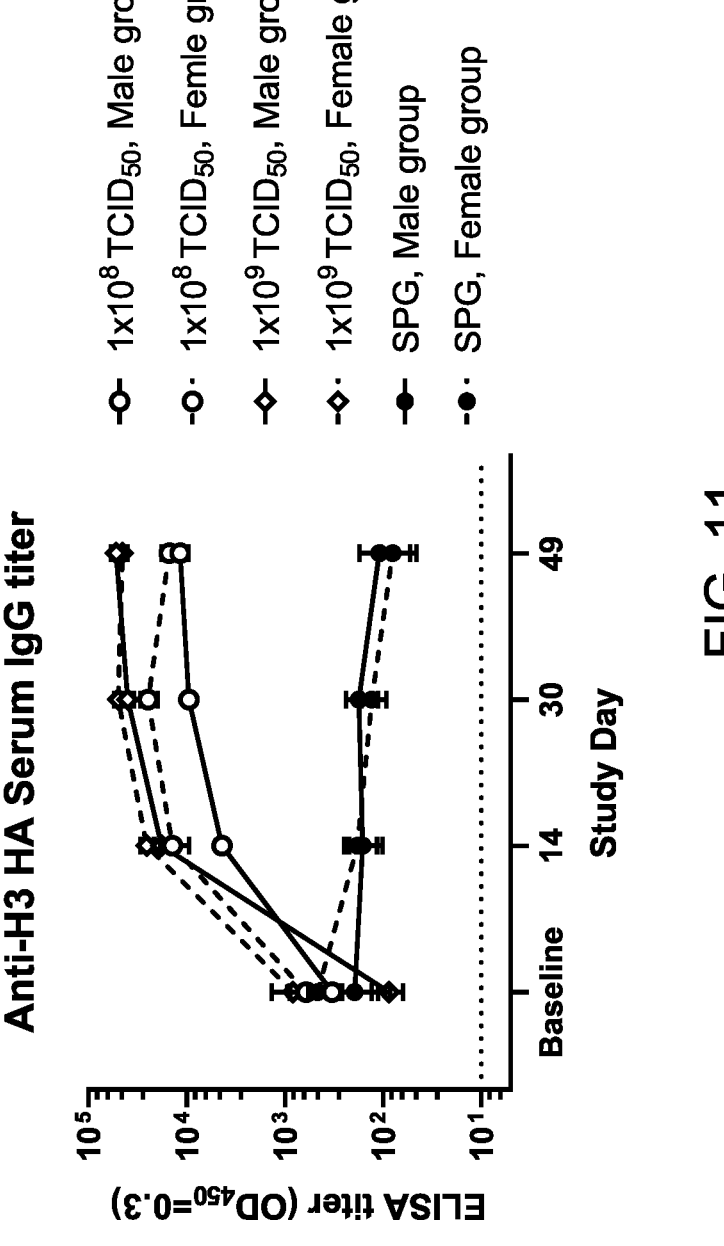
FIG. 11 is a graph depicting the anti-H3 HA ELISA IgG titer in sera of ferrets immunized with $1\times10^8$ $TCID_{50}$ H3N2 FGHY1-M2SR, $1\times10^9$ H3N2 FGHY1-M2SR, or SPG (control) on study days 14, 30, and 49.

The resulting anti-H3 HA ELISA IgG titer in sera data is shown in FIG. 11. Ferrets in each of the immunized groups showed significant elevation of anti-H3 HA antibody in serum, while antibody levels in animals that received SPG only did not change from baseline. Anti-H3 HA antibody titers were higher in immunized groups than SPG control groups two weeks after the prime dose. Mean antibody titers per immunized group increased further following first and second administrations of the vaccine.

Hemagglutination Inhibition (HAI) Assay: To demonstrate the functional activity of antibodies detected by ELISA, serum samples were analyzed by HAI assay. Serum samples were treated with RDE to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. A solution comprised of 0.85% NaCl was added to each sample to a final serum dilution of 1:10 after the RDE treatment. The samples were then further diluted two-fold (1:10 to 1:1280) in PBS and incubated with 4 hemagglutinating units of influenza A/Singapore/INFIMI-1-16-0019/2016 (H3N2) viruses. After incubation, 0.5% avian red blood cells were added to each sample and incubated for 30±5 minutes. Presence or absence of hemagglutination was then scored.

Figure 12:
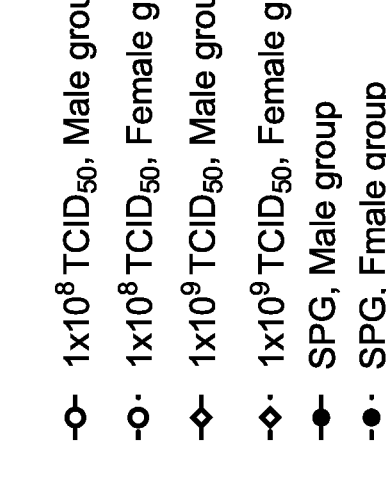
FIG. 12 is a graph depicting the anti-H3 HAI titer in sera of ferrets immunized with $1\times10^8$ $TCID_{50}$ H3N2 FGHY1-M2SR, $1\times10^9$ H3N2 FGHY1-M2SR, or SPG (control) on study days 14, 30, and 49.
Figure 12:
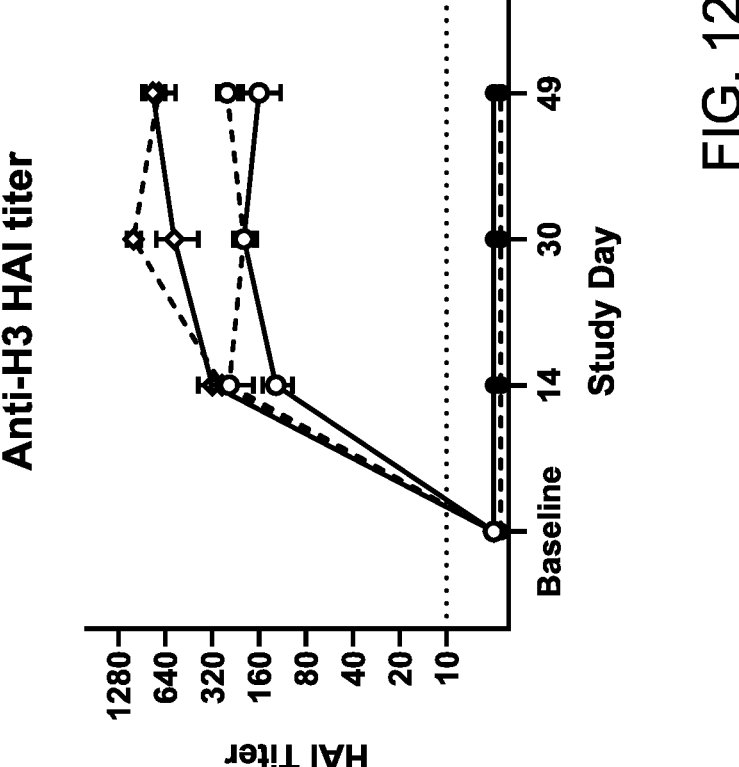

The resulting anti-H3 HAI titer in sera data is showing in FIG. 12. High dose ($1 \times 10^9$ TCID$_{50}$) groups tended to show higher HAI titer than low dose ($1 \times 10^8$ TCID$_{50}$) groups. The SPG (control) group did not elicit any HAI titers. All H3N2 FGHY1-M2SR immunized ferrets, except one male in $1 \times 10^9$ TCID$_{50}$, demonstrated equal to or higher than 80 HAI titers against test virus. The CDC states that serum HAT antibody titers of 40 are associated with at least a 50% reduction in risk for influenza infection or disease in populations. Therefore, these results suggest that FGHY1-M2SR virus is able to elicit protective immune responses.

Virus Neutralization Assay: Pre-study and treatment phase serum samples (from study days 3, 14, 30, and 49) were tested against A/Singapore/INFIMH-16-0019/2016 (H3N2) influenza virus in a virus neutralization assay. The serum samples were inactivated at 56° C. for 30 minutes. The sera were then serially diluted 2-fold and incubated with standardized virus (concentration of 80-140 PFU) at 37±2° C. in 5.0±1% CO$_2$ for 60 minutes. One hundred microliter (100 μL) of each serum and virus mixture was then transferred into the respective wells of a 96-well plate containing a monolayer of MDCK cells. The plate (with samples) was then incubated for 18-22 hours at 37±2° C. in 5.0±1% CO$_2$. After incubation, the cells were fixed with paraformaldehyde and stained with an anti-influenza A nucleoprotein monoclonal antibody pool (1 part MAB8257: 1 part MAB8258 (Millipore; Billerica, MA)) followed by peroxidase-conjugated goat anti-mouse IgG. The spots were developed using TrueBlue Peroxidase Substrate (Kirkegaard and Perry Laboratories; Gaithersburg, MD). The plaques were visualized and counted using an ELISPOT instrument (AID GmbH, Strassberg, Germany). The 50% plaque reduction neutralization titer (PRNT$_{50}$) was calculated by counting plaques and reporting the titer as the reciprocal of the last serum dilution to show 50% reduction of the input control virus plaque count as based on the back-titration of control plaques.

Figure 13:
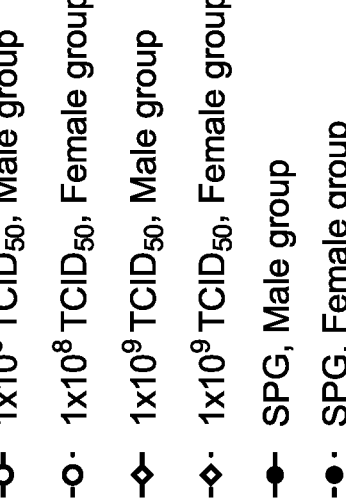
FIG. 13 is a graph depicting the anti-$H_3$ $PRNT_{50}$ titer in sera of ferrets immunized with $1\times10^8$ $TCID_{50}$ H3N2 FGHY1-M2SR, $1\times10^9$ H3N2 FGHY1-M2SR, or SPG (control) on study days 14, 30, and 49.
Figure 13:
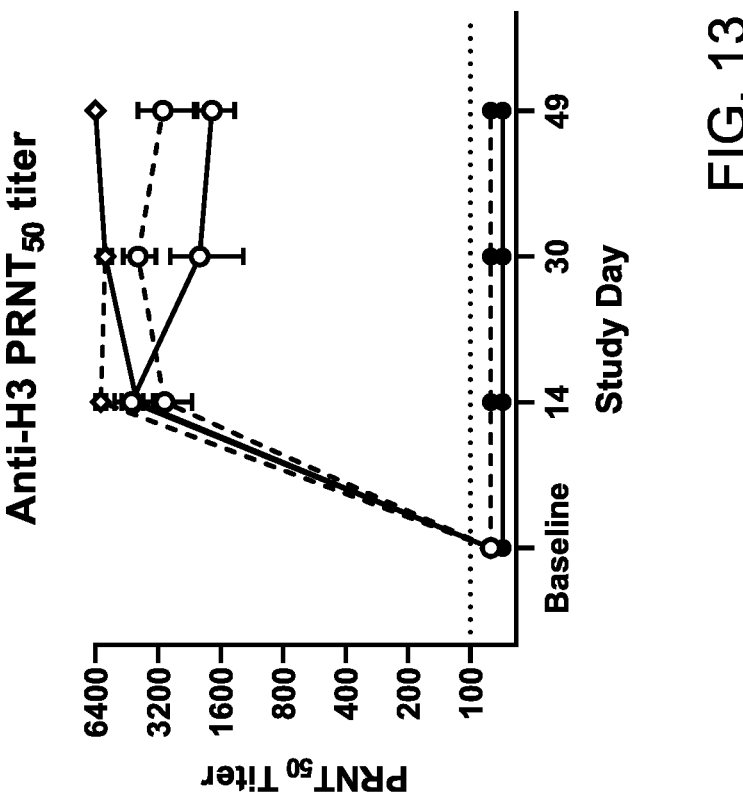

The resulting anti-H3 PRNT50 titer in sera data is showing in FIG. 13. All ferrets within the SPG group remained negative (titers<100) for the duration of the study. Ferrets who were immunized with H3N2 FGHY1-M2SR at a dose of $1 \times 10^8$ TCID$_{50}$ had geometric mean titre (GMT) VN titers of 1916, 1838 and 1970 on Days 14, 30 and 49, respectively. Ferrets who were immunized with H3N2 FGHY1-M2SR at a dose of $1 \times 10^9$ TCID$_{50}$ had GMT VN titers of 4434, 5572 and 6400 on Days 14, 30 and 49, respectively. Because sera was diluted up to 1:6400, PRNT$_{50}$ titers higher than 6400 were not specifically measured. All ferrets who were immunized with 3 doses of H3N2 FGHY1-M2SR at $1 \times 10^9$ TCID$_{50}$ exhibited PRNT$_{50}$ titers of 6400 or higher.

Clinical Pathology: For all surviving ferrets, blood samples for the analysis of clinical chemistry, hematology and coagulation parameters were collected from the jugular vein or vena cava pre-study and on days 3, 14, 16, 30, and 49. Animals were fasted for 4-6 hours prior to blood collection. EDTA was used as the anticoagulant for hematology samples, while sodium citrate was used for coagulation samples. Samples for clinical chemistry were collected without an anticoagulant. Urine samples were collected directly from the bladder of each ferret at necropsy.

No treatment-related or toxicologically significant findings were noted for any of the clinical chemistry or hematology parameters evaluated during the study. The increase in fibrinogen observed in vaccine-treated groups was considered an "expected inflammatory response" following treatment with immunogenic substances. Fibrinogen returned to control levels after the 14-day and 21-day recovery periods suggesting this effect was acute and reversible. The decreases in prothrombin time (PT) were reversible following cessation of dosing; therefore, this effect was considered to be of minimal toxicological significance.

Gross Necropsy and Histopathology: Gross necropsy and histopathology were carried out on study days 3, 30 and 49 for 5 males and 5 females per group. Intranasal immunization of H3N2 FGHY1-M2SR to ferrets at a dose of $1 \times 10^8$ TCID$_{50}$ resulted in no gross findings, with microscopic findings noted in the lung (mixed cell infiltrates) on Day 3 and Day 30. At a dose of $1 \times 10^9$ TCID$_{50}$, gross findings were noted in the lung (pigmentation, dark or mottled) and microscopic findings were noted in the lung (mixed cell infiltrates) on Day 3 and 30. After a 3-week recovery, on study day 49, no test article-related gross lesions were observed.

Therefore, this example shows that intranasal immunization of the H3N2 FGHY1-M2SR vaccine virus does not spread in the vaccinated host and is not associated with any vaccine-related adverse events (e.g., elevated body temperature, loss of weight, or clinical signs). These results indicate that the H3N2 FGHY1-M2SR virus elicits protective immune responses against homologous test virus after a single dose that can be further elevated with repeat dosing and is useful as an intranasal influenza vaccine.

Example 12

This example demonstrates that FGHY1-M2SR viruses elicit antibody responses against influenza A viruses formulated in multivalent vaccines.

Influenza A H1N1 or H3N2 FGHY1-M2SR viruses elicit antibody responses when formulated as a monovalent, bivalent, trivalent, or quadrivalent vaccine.

Seven-week-old BALB/c female mice (N=8) were immunized intranasally with monovalent H1N1 FGHY1-M2SR, monovalent H3N2 FGHY1-M2SR, bivalent H1N1 and H3N2 FGHY1-M2MR, trivalent H1N1 and H3N2 FGHY1-M2SR and BM2SR Victoria or Yamagata, or quadrivalent H1N1 and H3N2 FGHY1-M2SR and BM2SR Victoria and Yamagata vaccines. A control group of mice were mock immunized with SPG. 28 days after vaccination, the mice were immunized intranasally with a boost immunization consisting of the same vaccine administered for the prime immunization. Serum samples were taken on days 7, 14, and 21 following prime immunization and on days 35, 42 and 49 following the boost immunization (day 28). Anti-H1 HA and anti-H3 HA serum IgG antibody titers from the serum samples were determined by ELISA.

Figure 14A:
FIG. 14A is a graph depicting the anti-H1 HA titer in sera from mice immunized with monovalent H1N1 FGHY1-M2SR, monovalent H3N2 FGHY1-M2SR, bivalent FGHY1-M2SR, trivalent FGHY1-M2SR+BM2SR-Vic, trivalent FGHY1-M2SR+BM2SR-Yam, quadrivalent, or SPG (control) versus time (days post-immunization).
Figure 14B:
FIG. 14B is a graph depicting the anti-H3 HA titer in sera from mice immunized with monovalent H1N1 FGHY1-M2SR, monovalent H3N2 FGHY1-M2SR, bivalent FGHY1-M2SR, trivalent FGHY1-M2SR+BM2SR-Vic, trivalent FGHY1-M2SR+BM2SR-Yam, quadrivalent, or SPG (control) versus time (days post-immunication).
Figure 14B:

The resulting anti-H1 HA data is shown in FIG. 14A. The resulting anti-H3 HA data is shown in FIG. 14B. The results demonstrated that all vaccines were able to elevate anti-influenza virus antibodies above SPG control and that these increases were comparable across vaccine formulations. These results demonstrate that there is no interference between the monovalent components when formulated into multivalent vaccines.

Example 13

This example shows that the intranasally administered monovalent or quadrivalent FGHY1-M2SR vaccine protects mice from lethal influenza A virus that is not contained in the vaccine.

Figure 15:
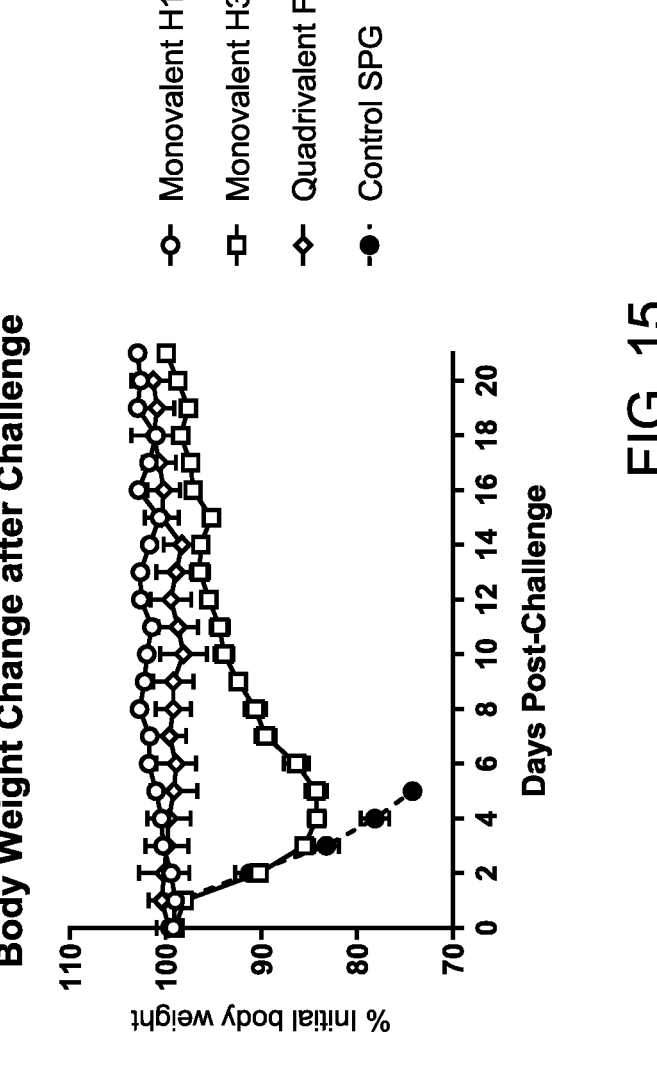
FIG. 15 is a graph depicting mouse percent body weight change after challenge with influenza A/California/07/2009 (H1N1) virus of mice immunized with monovalent H1N1 FGHY1-M2SR, monovalent H3N2 FGHY1-M2SR, quadrivalent FGHY1-M2SR, or SPG (control) versus time (days post-challenge).

The BALB/c female mice described in Example 12 were challenged with a lethal dose of influenza A/California/07/2009 (H1N1) virus (>10 mouse 50% lethal dose (MLD$_{50}$)) 70 days after the first immunization (6 weeks after the boost immunization). All mice immunized with the monovalent H1N1 (influenza A/Montana/50/2016) or H3N2 (influenza A/Singapore/INFIM11-16-0019/2016) FGHY1-M2SR and quadrivalent FGHY1-M2SR and BM2SR vaccines survived the challenge. The mice immunized with monovalent H1N1 FGHY1-M2SR and quadrivalent FGHY1-M2SR and BM2SR vaccines remained healthy with no body weight loss. The resulting body weight lost data is showing in FIG. 15. Mice who were immunized with monovalent H3N2 FGHY1-M2SR lost transient weight, but fully recovered. The control mice that were mock immunized with only SPG lost body weight and sucumbed to infection within 5 days post-challenge. On day 3 post-challenge, lungs were obtained from 3 mice per group, and viral load was determined via plaque assay in MDCK cells. As shown in Table 8, virus titers in the lungs of mice that were immunized with monovalent H1N1 FGHY1-M2SR and quadrivalent vaccine were below the limit of detection (less than 76 plaque forming units (PFU) per lung). Viral load was detected in mice immunized with H3N2 FGHY1-M2SR (6.60 log PFU/g). However, average virus titer from 3 mice were approximately 1 log lower than naï control SPG mice (7.52 log PFU/g). These results indicate that the M2SR monovalent and quadrivalent vaccines confer cross-protection and limit the replication of a challenge virus that does not match any vaccine component.

TABLE 8

Challenge Virus Titer in Lungs, 3 Days Post-Challenge

| Vaccine | Mouse | Lung virus titer (log PFU/g) | Average lung virus titer ± SD (log PFU/g) |
|---|---|---|---|
| H1N1 FGHY1-M2SR | 1 | —* | — |
| | 2 | — | |
| | 3 | — | |
| H3N2 FGHY1-M2SR | 1 | 6.7 | 6.60 ± 0.1 |
| | 2 | 6.6 | |
| | 3 | 6.4 | |
| Quadrivalent | 1 | — | — |
| | 2 | — | |
| | 3 | — | |
| Control SPG | 1 | 7.5 | 7.52 ± 0.1 |
| | 2 | 7.4 | |
| | 3 | 7.6 | |

*—: Below detection limit (76 PFU/g)

Example 14

This example shows that the quadrivalent FGHY1-M2SR provides a favorable safety profile compared to licensed intranasal influenza vaccine as well as superior protection to licensed intramuscular inactivated influenza vaccines against influenza viruses that are not contained in the vaccine. The antigenically shifted monovalent H3N2 FGHY1-M2SR vaccine provides comparable protection to antigenically matched licensed vaccine in protection of mice from lethal influenza A virus.

Seven-week-old BALB/c female mice (N=13) were immunized with one of the following vaccines: monovalent H3N2 FGHY1-M2SR, quadrivalent FGHY-M2SR, Flu-Mist® Quadrivalent (AstraZeneca, Wilmington, DE), Flu-zone® Quadrivalent (Sanofi, Bridgewater, NJ) or Fluzone® High Dose (Sanofi). Strain components for each vaccine are shown in Table 9. FGHY1-M2SR and FluMist were intra-nasally dosed while both Fluzone vaccines were intramus-cularly dosed. A control group of mice were intranasally mock immunized with SPG. The mice were observed for 14 days after immunization for any change in body weight.

TABLE 9

Strain Components for Each Vaccine

| | | | Influenza B | |
|---|---|---|---|---|
| | Influenza A | | Yamagata | Victoria |
| Vaccine | (H1N1pdm) | (H3N2) | Lineage | Lineage |
| H3N2 FGHY1-M2SR | None | A/SINGAPORE/INF IMH-16-0019/2016 | None | None |
| Quadrivalent FGHY1-M2SR | A/MI/45/2015-like A/MT/50/2016 | A/SINGAPORE/INF IMH-16-0019/2016 | B/Phuket/3073/ 2013-like B/CA/12/2015 | B/CO/06/2017 |
| FluMist | A/MI/45/2015-like A/Slovenia/2903/ 2015 | A/SINGAPORE/INF IMH-16-0019/2016 | B/Phuket/3073/ 2013 | B/CO/06/2017 |
| Fluzone Quadrivalent | A/MI/45/2015 | A/SINGAPORE/INF IMH-16-0019/2016 | B/Phuket/3073/ 2013 | B/MD/15/2016 |
| Fluzone High Dose | A/MI/45/2015 | A/SINGAPORE/INF IMH-16-0019/2016 | None | B/MD/15/2016 |

Figure 16:
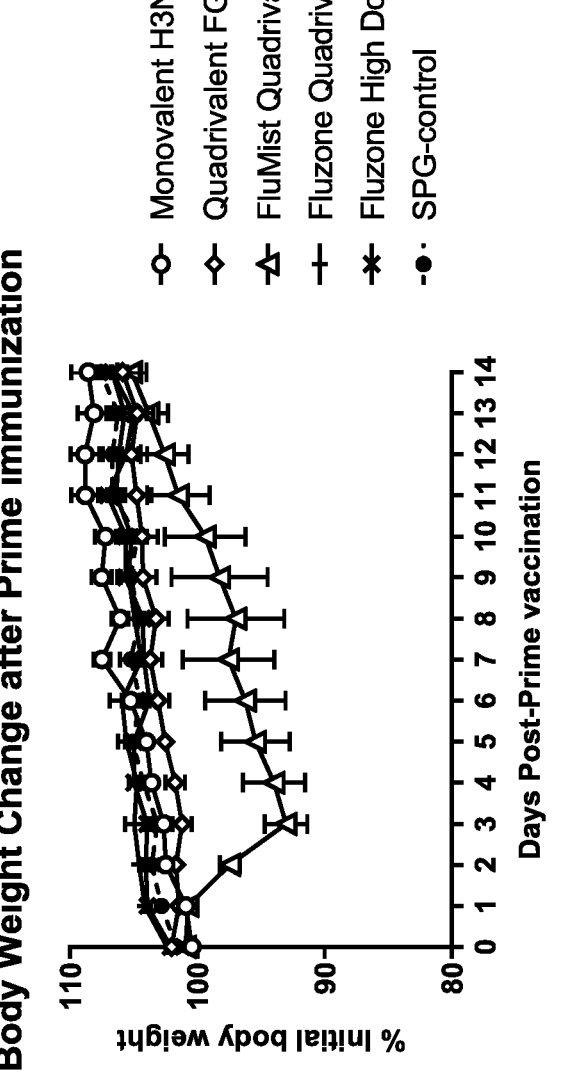
FIG. 16 is a graph depicting mouse percent body weight change after immunization with monovalent H3N2 FGHY1-M2SR, quadrivalent FGHY1-M2SR, FluMist Quadrivalent, Fluzone Quadrivalent, Fluzone High Dose, or SPG (control) versus time (days post-vaccination).

The resulting weight-loss data is shown in FIG. 16. Mice that were immunized with monovalent H3N2 FGHY1-M2SR, quadrivalent FGHY1-M2SR, Fluzone Quadrivalent, Fluzone High Dose, or SPG control experienced no body weight loss over the 14-day period. However, mice that were immunized with FluMist lost an average of 7% body weight on day 3 post-vaccination and took 14 days to recover. These data indicate that FGHY1-M2SR vaccines have a better safety profile than the licensed live attenuated influenza vaccine, FluMist.

Figure 17A:
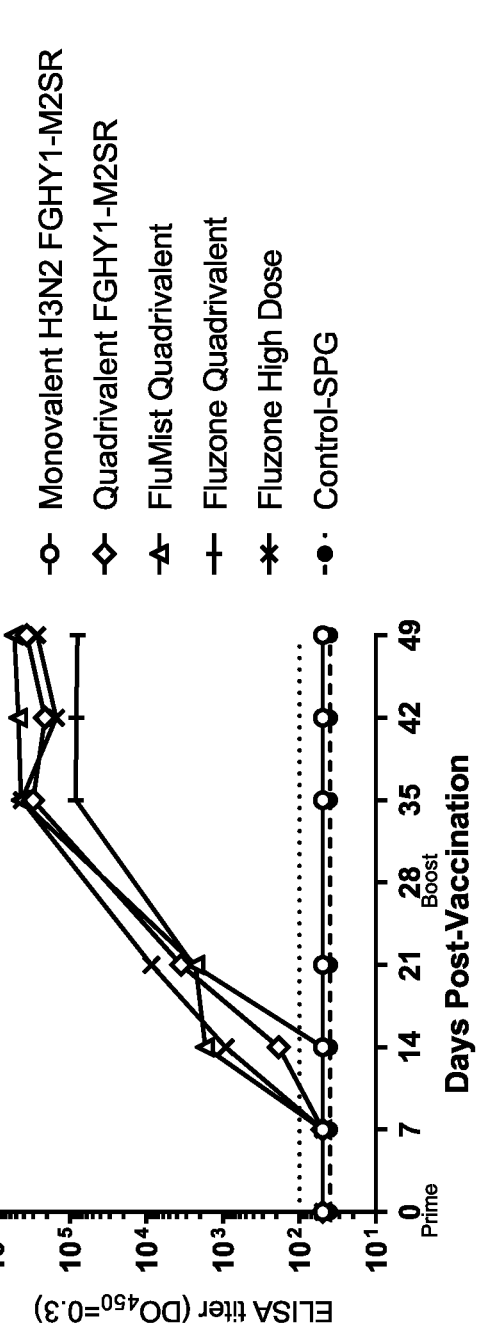
FIG. 17A is a graph depicting the anti-influenza A/H1 HA serum IgG ELISA titers in sera of mice immunized with monovalent H3N2 FGHY1-M2SR, quadrivalent FGHY1-M2SR, FluMist Quadrivalent, Fluzone Quadrivalent, Fluzone High Dose, or SPG (control) versus time (days post-vaccination).
Figure 17B:
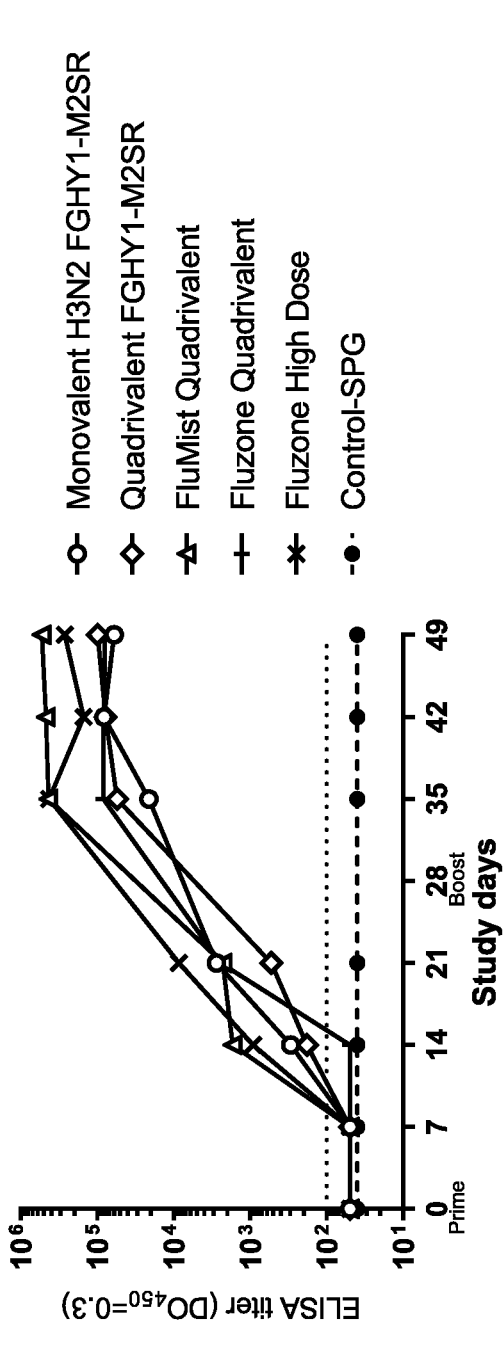
FIG. 17B is a graph depicting the anti-influenza A/H3 HA serum IgG ELISA titers in sera of mice immunized with monovalent H3N2 FGHY1-M2SR, quadrivalent FGHY1-M2SR, FluMist Quadrivalent, Fluzone Quadrivalent, Fluzone High Dose, or SPG (control) versus time (days post-vaccination).
Figure 17C:
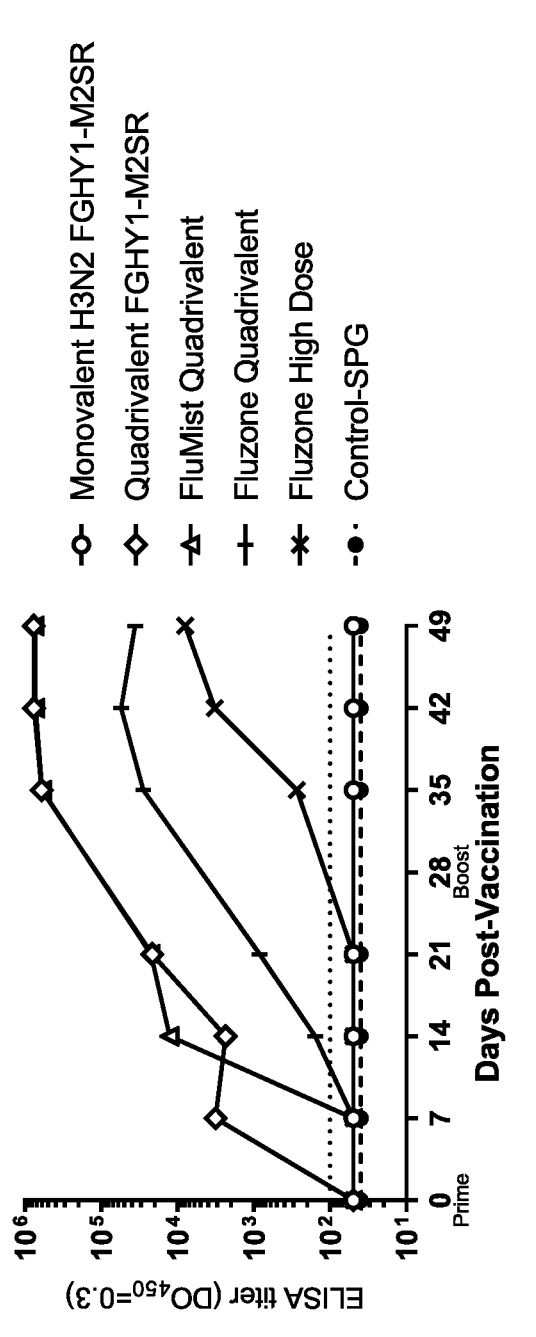
FIG. 17C is a graph depicting the anti-influenza B/Yam HA serum IgG ELISA titers in sera of mice immunized with monovalent H3N2 FGHY1-M2SR, quadrivalent FGHY1-M2SR, FluMist Quadrivalent, Fluzone Quadrivalent, Fluzone High Dose, or SPG (control) versus time (days post-vaccination).
Figure 17D:
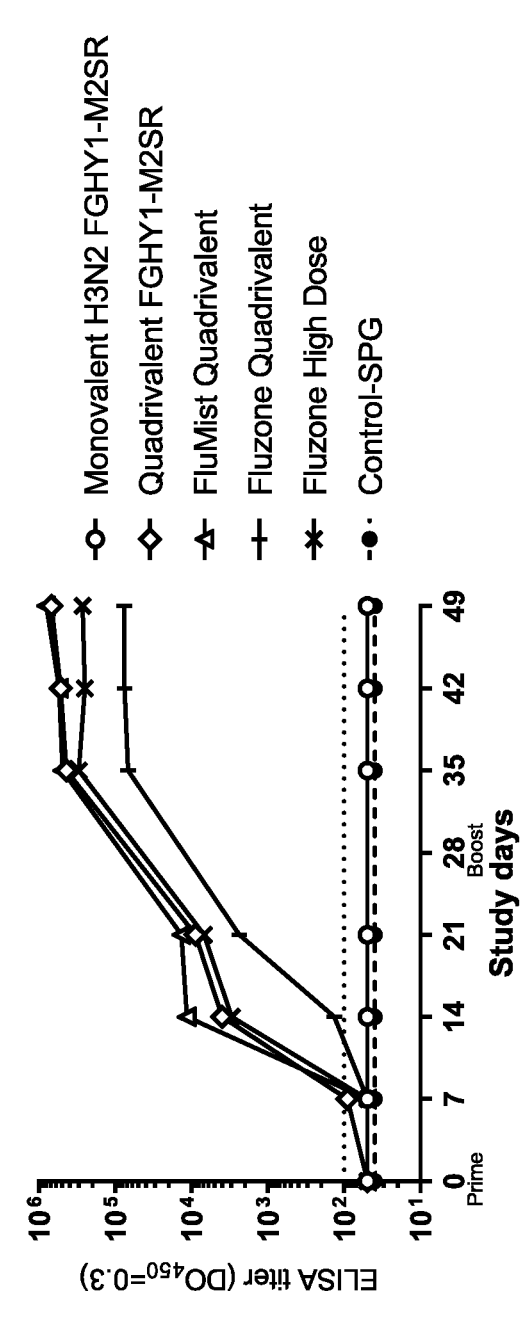
FIG. 17D is a graph depicting the anti-influenza B/Vic HA serum IgG ELISA titers in sera of mice immunized with monovalent H3N2 FGHY1-M2SR, quadrivalent FGHY1-M2SR, FluMist Quadrivalent, Fluzone Quadrivalent, Fluzone High Dose, or SPG (control) versus time (days post-vaccination).

The mice were immunized with a boost immunization on day 28 post-prime immunization. The boost immunization consisted of the same vaccine the mice were immunized with in the prime immunization. Serum samples were collected weekly after prime and boost immunizations, and pooled serum IgG titers against each of the vaccine components were determined by ELISA. Resulting anti-influenza A/H1 HA serium IgG ELISA titers data are showing in FIG. 17A. Resulting anti-influenza A/H3 HA serium IgG ELISA titers data are shown in FIG. 17B. Resulting anti-influenza B/Yam HA serum IgG ELISA titers data are shown in FIG. 17C. Resulting anti-influenza B/Vic HA serum IgG ELISA titers data are shown in FIG. 17D. The results demonstrate that all vaccines except monovalent H3N2 FGHY1-M2SR were able to elevate serum IgG titers against influenza A H1 and H3 HA above SPG control, and that these increases were comparable across vaccine formulations. Fluzone Quadrivalent and Fluzone High Dose elicited lower serum IgG titers against influenza B HA antigens compared to live vaccines. Monovalent H3N2 FGHY1-M2SR vaccine caused serum IgG elevation only against H3 HA antigen as expected.

Figure 18A:
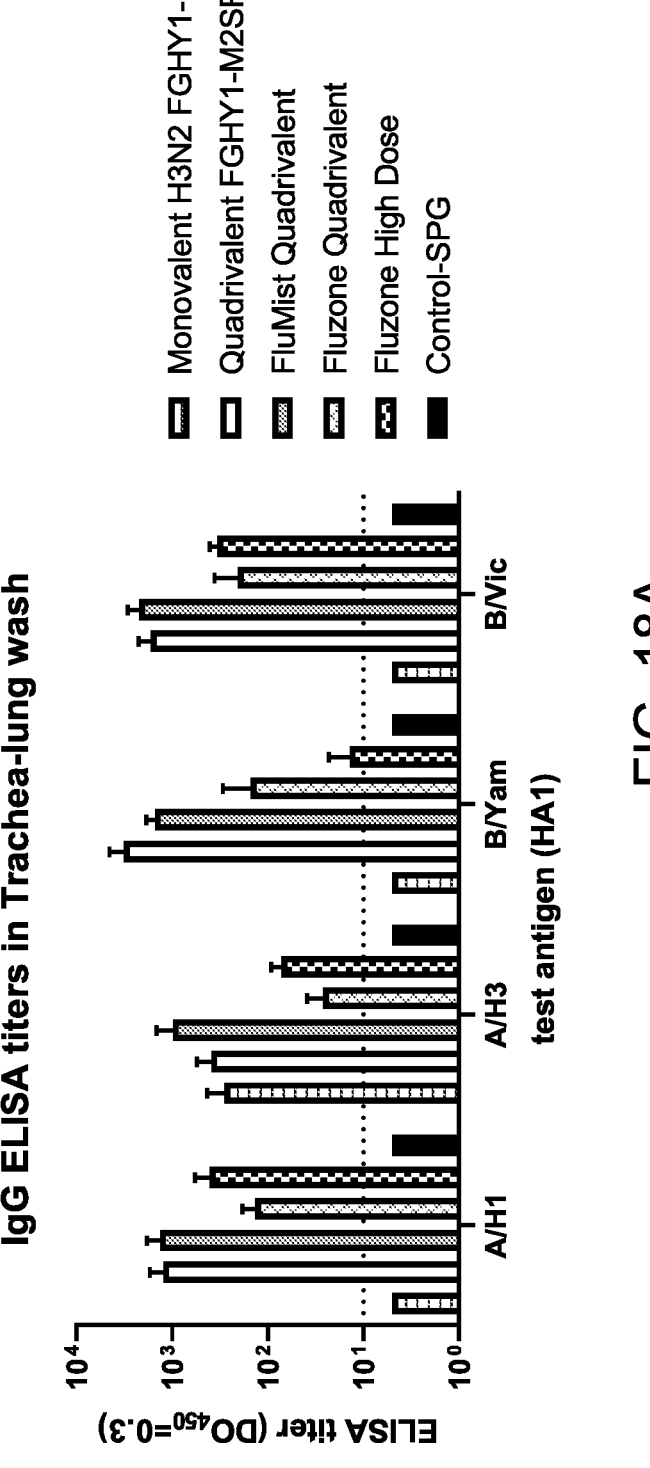
FIG. 18A is a graph depicting IgG ELISA titers in trachea-lung wash of mice immunized with monovalent H3N2 FGHY1-M2SR, quadrivalent FGHY1-M2SR, FluMist Quadrivalent, Fluzone Quadrivalent, Fluzone High Dose, or SPG (control) versus HAI test antigen (A/H1, A/H3, B/Yam, or B/Vic).
Figure 18B:
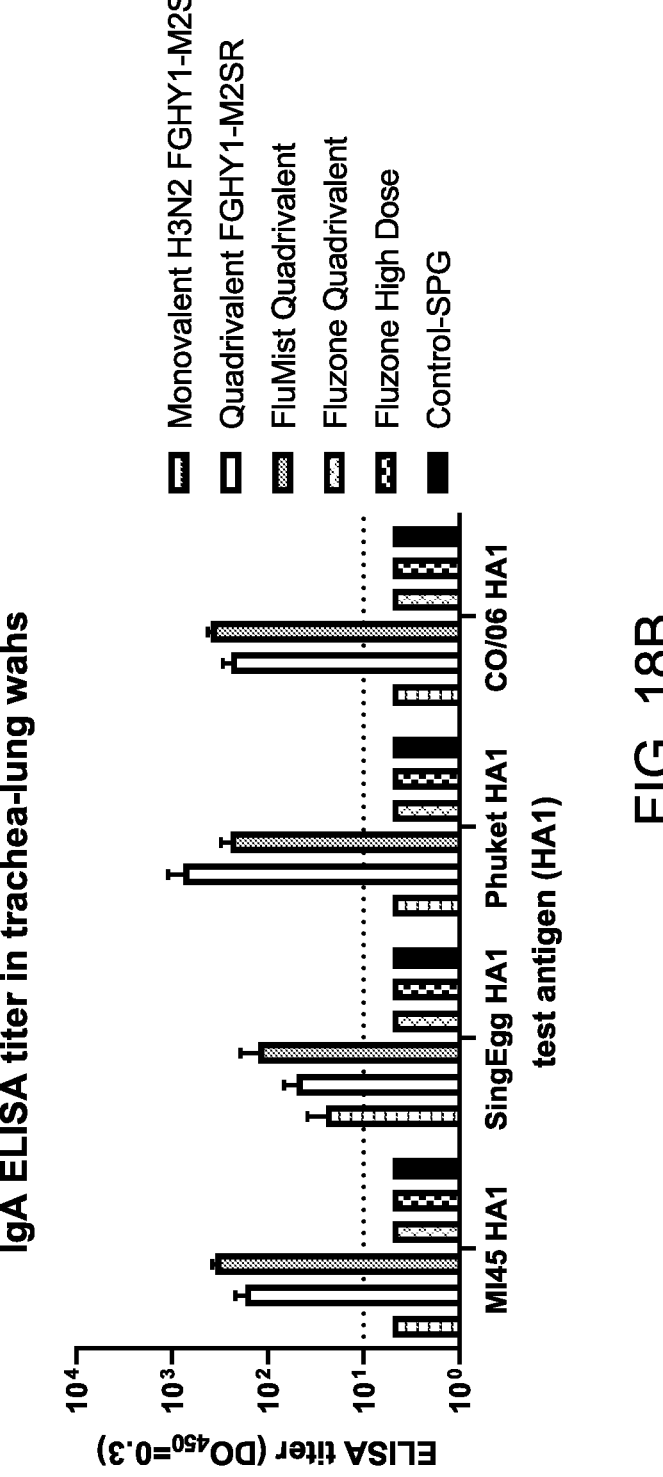
FIG. 18B is a graph depicting anti-influenza HAI IgA ELISA titers in trachea-lung wash of mice immunized with monovalent H3N2 FGHY1-M2SR, quadrivalent FGHY1-M2SR, FluMist Quadrivalent, Fluzone Quadrivalent, Fluzone High Dose, or SPG (control) versus HAI test antigen (MI45, SingEgg, Phuket or CO/06).

Trachea-lung washes were obtained from 4 mice per group on day 49 post-prime immunization (21 days post-boost) and IgG and IgA titers were determined by ELISA to evaluate mucosal immune responses. The resulting IgG titers data is shown in FIG. 18A and resulting IgA titers data is shown in FIG. 18B. Quadrivalent FGHY1-M2SR and FluMist elicited both IgG and IgA titers against all test antigens. Mice immunized with monovalent H3N2 FGHY1-M2SR exhibited IgG and IgA titers against H3 HA antigen, but not against H1 or influenza B HA antigens. IgG titers against all four antigens were elevated in groups that were immunized with Fluzone Quadrivalent and Fluzone High Dose vaccine, however, no IgA antibody titer was detected to any antigen. These data indicate that FGHY1-M2SR vaccines elicit mucosal immune responses comparable to licensed live attenuated influenza vaccine, FluMist, whereas licensed intramuscular influenza vaccines do not elicit any mucosal immune responses.

Figure 19:
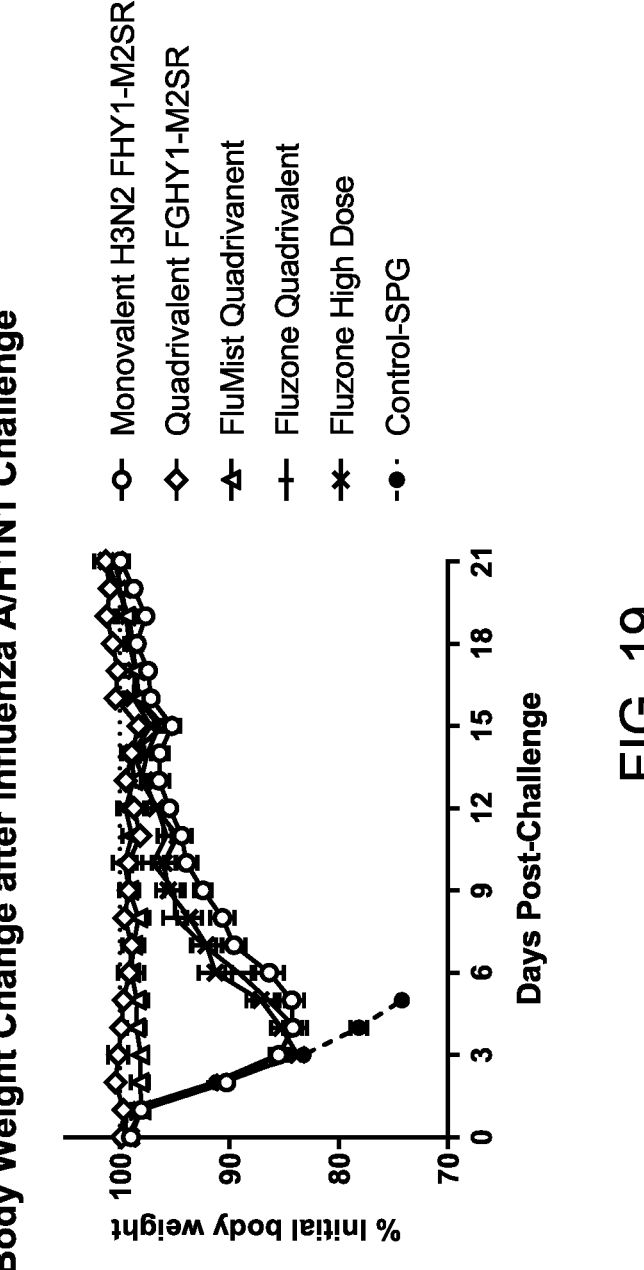
FIG. 19 is a graph depicting mouse percent body weight change after challenge with influenza A/H1N1 of mice immunized with H3N2 FGHY1-M2SR, quadrivalent FGHY1-M2SR, FluMist Quadrivalent, Fluzone Quadrivalent, Fluzone High Dose, or SPG (control) versus time (days post-challenge).

Mice were challenged with a lethal dose of influenza A/California/07/2009 (H1N1pdm) 6 weeks after the boost immunization. Mice that were mock immunized with SPG control succumbed to infection by day 5 post-challenge, while all vaccine groups survived. The resulting body weight change after challenge is shown in FIG. 19. Quadrivalent FGHY1-M2SR and FluMist groups did not lose any body weight and challenged virus was not detected in lungs or nasal turbinate on day 3 post-challenge, as seen in Table 10, suggesting these intranasal vaccines provided sterilizing immunity against lethal infection with a drifted influenza virus. Mice in the monovalent H3N2 FGHY1-M2SR (heterosubtypic to challenge virus), Fluzone Quadrivalent, and Fluzone High Dose groups lost more than 15% mean body weight on day 3 or 4 post-challenge and then recovered by day 21 post-challenge. Infectious virus was detected in lungs and nasal turbinate of mice vaccinated with monovalent H3N2 FGHY1-M2SR and Fluzone Quadrivalent. Mice immunized with the Fluzone High Dose vaccine had comparable body weight loss to mice immunized with monovalent H3N2 FGHY1-M2SR and Fluzone Quadrivalent vaccines, however, no infectious virus was recovered from lungs or nasal turbinate. These data indicate that the intranasally administered monovalent heterosubtypic H3N2 FGHY1-M2SR (i.e., lacking an H1N1 component) vaccine protects mice as well as the intramuscularly administered licensed inactivated vaccines that contain an H1N1 component.

TABLE 10

Virus Titers in Mouse Organs After Influenza A/CA/07/2009 (H1N1)

| Vaccine | Virus Titers[a] in | |
| --- | --- | --- |
| | Lungs | NT |
| H3N2 FGHY1-M2SR | 6.60 ± 0.13 | 4.33 ± 0.12 |
| Quadrivalent FGHY1-M2SR | —[b] | — |
| FluMist | — | — |
| Fluzone Quadrivalent | 6.61 ± 0.27 | 5.73 ± 0.19 |
| Fluzone High Dose | — | 4.98, 4.38 |

[a]Organs were collected from 3 mice per group on day 3 post-challenge. Oragans were homogenized in 1 mL of 0.3% BSA-MEM, and titrated in MDCK cells. Titers are shown in log PFU/g, average ± SD or individual organ titers if not all mice had titers.
[b]—: Below detection limit 1 PFU/0.1 mL

Example 15

This example shows that FGHY1-M2SR virus manufacturing is scalable in M2VeroA cells and host cell DNA levels are reduced to levels recommended by WHO and FDA guidelines for vaccines produced in cell substrates.

M2VeroA cells (Vero cells that stably express influenza A M2 protein) were cultured in humidified incubators at 37° C. at 5% $CO_2$ atmosphere using OptiVero medium (InVitria, Aurora, CO). Approximately 242 million cells in a Cell-STACK®-5 Chamber (CS5; Corning, Corning, NY), 3 or 4 CellSTACKs per lot, were infected in OptiVero medium with H3N2 FGHY1-M2SR virus, encoding the HA and NA genes of Influenza A/Singapore/INFIMI-1-16-0019/2016I (H3N2) at multiplicity of infection (MOI) of 0.01. After 2-3 days at 35° C., 5% $CO_2$, when the HA titer of the supernatant was at least 32 HAU/50 the culture medium was harvested and cells and cell debris were removed by low speed centrifugation. The supernatant was further clarified and sterilized by vacuum filtration through a 0.2 μM pore PES membrane. The clarified supernatant was then treated with non-specific RNA and DNA nuclease (Benzonase, 5 units/mL) for 2 hours at 37° C. to digest/hydrolize residual cellular RNA and DNA. The Benzonase digested material was then purified by tangential flow filtration (TFF) using a 235 $cm^2$ 300 kD MWCO Modified Polyethersulfone (mPES) MidiKros® hollow fiber filter module (Repligen, Waltham, MA). The material was concentrated 10 to 20-fold. Then contaminating host cell proteins (HCP) and residual DNA fragments were removed by diafiltration using at least 15 column volumes SPG. The purified virus in SPG buffer was further concentrated 10 to 100-fold by ultracentrifugation at 25,000 rpm through a 25% sucrose PBS cushion. Resultant virus pellets were resuspended in SPG, aliquoted and then flash frozen in liquid $N_2$ followed by storage at −80° C.

The sequence homology of concentrated and purified H3N2 FGHY1-M2SR genes were compared against those of the reference sequences of the H3N2 FGHY1-M2SR virus seed stock. Viral RNA extracted from the purified viruses was subjected to reverse transcriptase-polymerase chain reaction (RT-PCR) to generate cDNA followed by Sanger sequencing. Analyses of open reading frames (ORFs) encoded by the 8 viral segments indicated that all segments had 100% nucleotide sequence identity to the reference.

The infectious titer of concentrated and purified H3N2 FGHY1-M2SR virus was determined by the 50% tissue culture infectious dose (TCID50) assay by at least three independent measurements using M2CK cells (MDCK cells that stably express influenza A M2). In the procedure, serial dilutions of the vaccine sample were applied to replicate M2CK cells in 96 well plates and cultured 4 days at 35° C. at 5% $CO_2$ atmosphere. At 4 days post-inoculation, the cell monolayers are visually examined and scored for CPE. The titer of the virus was calculated using the Reed and Muench method and expressed as the $TCID_{50}$/mL. Additionally, HA activity were tested in aliquots of each well supernatant to verify the virus titer determined by CPE. As shown in Table 11, after concentration and purification, H3N2 FGHY1-M2SR viruses consistantly reached a high titer of over $10^{9.8}$ $TCID_{50}$/mL.

TABLE 11

Virus titer after concentration and purification

| Lot # | Virus Culture Scale | Beginning Sample Volume | End Sample Volume | Mean Virus Titer ± s.d. (Log $TCID_{50}$/mL) |
|---|---|---|---|---|
| 18K01DM120-017 | 3 CS5 | 2.25 L | 10 mL | 9.81 ± 0.23 |
| 19C25DM120-072 | 4 CS5 | 3.00 L | 11 mL | 9.87 ± 0.35 |
| 19D10MM129-008 | 4 CS5 | 3.00 L | 11 mL | 9.89 ± 0.36 |

To confirm that the H3N2 FGHY1-M2SR vaccine virus maintained a replication-deficient phenotype after concentration and purification, the existence of any replicating virus was evaluated by three serial passages of the test article in MDCK cells which are permissive for wild-type influenza viruses but non-permissive for M2SR virus. In the first round of infection, test virus was serially diluted and inoculated onto the cell monolayer. Infected cells were then cultured for 4 days at 35° C. at 5% $CO_2$ atmosphere. Infected cell culture supernatant was then transferred to a fresh MDCK monolayer and incubated for 4 days at 35° C. at 5% $CO_2$ atmosphere. For the third and final round of passage, this infected cell culture media was transferred to another fresh MDCK monolayer and incubated for an additional 4 days at 35° C. at 5% $CO_2$ atmosphere. MDCK cells were observed for CPEs after every 4-day 35° C. culture and HA activity in culture supernatants were determined to confirm existence of progeny virions. For each round of infection, a replication-deficient reference virus, Bris10 M2SR was tested as a positive control. Negative control inoculum was media only. The results indicated that the controls performed as expected, and that no infectious progeny were detected after inoculation of normal cells with any of the four test articles. Thus, the H3N2 FGHY1-M2SR vaccine virus preparations were demonstrated to be replication incompetent, not capable of replication.

The fragment sizes of residual host cell DNA in the concentrated, purified FHGY1-M2SR was measured by use of capillary electrophoresis on a 2100 BioAnalyzer instrument (Agilent, Santa Clara, CA). Total sample DNA was extracted using Axygen® magnetic silica beads (Corning, Corning, NY). DNA purified from the sample was loaded onto a DNA High Sensitivity Chip (Agilent) and subjected to automated capillary electrophoresis. The 2100 Expert software was used to analyze data to detect fragments, obtain fragment concentrations, relative percentage of total DNA and measure sizes in base pairs (bp) for the extracted residual DNA. Results obtained from quadruplicate measurements of three lots of concentrated, purified FGHY1-M2SR demonstrated low to no fluorescence signal intensity on the 2100 Expert indicating that they contained insufficient residual DNA for accurate size determination.

The commercially available ELISA kit (Cygnus Technologies part number F500, Southport, NC) was used for the quantification of Vero host HCP present in the concentrated, purified H3N2 FGHY1-M2SR vaccine lots. The resulting data of HCP present is shown in Table 12. The antibodies in the kit were generated and affinity purified using Vero lysate and have been shown to detect HCPs from many commercially available Vero cell lines that were used to produce viral products. Thus, this kit can be used as a tool to monitor levels of Vero HCP contaminants. The kit was used according the manufacturers assay protocol. Multiple dilutions of each sample were prepared with sample diluent (Cygnus Cat #I028) and analyzed (in duplicate) to ensure that the samples display dilutional linearity (i.e. the High Dose Hook Effect is absent) within the range of the standards provided with the kit. A standard curve was constructed using 4-parameter logistic regression and was used to interpolate values for the samples.

TABLE 12

Host Cell Protein (HCP) content of concentrate and purified vaccine virus.

| Lot # | Vero HCP (µg/mL) | % Reduction in HCP Content (Harvest to vaccine) |
|---|---|---|
| 18K01DM120-017 | 2.72 | 99.99% |
| 19C25DM120-072 | 0.34 | 99.99% |
| 19D10MM129-008 | 0.88 | 99.98% |

The average amount of HCPs in vaccine preparations tested was 1.4±1.0 µg/mL. These values are in line with levels of HCP previously detected in clinical trial material (Bris10 M2SR, lot #15100251). The HCP for the three vaccine preparations was reduced by 99.98% to 99.99%.

Sterility of the vaccine preparations was verified by a procedure based upon WHO specifications for pharmaceutical preparations. Vaccine preparations were inoculated under aseptic conditions into three types of liquid medium, Luria-Bertani broth (LB), tryptic soy broth (TSB), and thioglycolate medium (TGM). Cultures were grown at 37° C. (LB and TSB) and at ambient temperature (TGM). The cultures were grown for 14 days and then examined visually for microbial growth. All of the preparations tested were negative for microbial growth in all growth conditions.

The osmolality values of the H3N2 FGHY1-M2SR vaccine lots were measured using a Fiske Model 210 Micro-Osmometer (Fiske Associates, Norwood, MA). The resulting osmolality data is shown in Table 13. A three point (50, 850, and 2000 mOsm/kg) calibration was performed prior to use each day and a five point linearity check (100, 500, 900, 1500, and 2000 mOsm/kg) was evaluated weekly to assure that these standards fell within expected values as specified by the manufacturer. Calibration and measurements were performed according the Fiske Model 210 Micro-Osmometer User's Guide. All the vaccine samples tested were found within a range of 604 to 616 mOsm/kg, osmolality measurements that were similar to that found with the SPG vehicle 595 to 626 mOsm/kg. These values are in line with those obtained for clinical trial material (Bris10 M2SR, lot #15100251).

TABLE 13

| Osmolality of Vaccine Preparations Ferret Vaccination Aliquot Retains | | |
| --- | --- | --- |
| Test Article | Lot | Sample Osmolality (mOsm/kg) |
| SPG Buffer | 120-072 | 595 |
| Sing2016 M2SR | 18K01DM120-017 | 616 |
| Sing2016 M2SR | 19C25DM120-072 | 604 ± 11 |
| Sing2016 M2SR | 19D10MM129-008 | 609 |

The H3N2 FGHY1-M2SR vaccine lots were manufactured in the M2VeroA cells using a similar process as the intended clinical material and formulated in SPG buffer as the intended clinical material. The characterization tests showed that the purification process was successful in removal of the host cell impurities (DNA and protein) and simulated the purity of clinical material, yet infectious titers were kept high and vaccine virus genome sequences and replication-deficient phenotype was maintained.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B")

is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. An influenza virus comprising PB1, PB2, PA, NP, and NS gene segments, wherein (a) the PB1 gene segment encodes a PB1 protein having the amino acid sequence of SEQ ID NO: 7, the PB2 gene segment encodes a PB2 protein having the amino acid sequence of SEQ ID NO: 15, the PA gene segment encodes a PA protein having the amino acid sequence of SEQ ID NO: 17, the NP gene segment encodes an NP protein having the amino acid sequence of SEQ ID NO: 6, and the NS gene segment encodes an NS1 protein having the amino acid sequence of SEQ ID NO: 19, or (b) the PB1 gene segment encodes a PB1 protein having the amino acid sequence of SEQ ID NO: 9, the PB2 gene segment encodes a PB2 protein having the amino acid sequence of SEQ ID NO: 10, the PA gene segment encodes a PA protein having the amino acid sequence of SEQ ID NO: 17, the NP gene segment encodes an NP protein having the amino acid sequence of SEQ ID NO: 8, and the NS gene segment encodes an NS1 protein having the amino acid sequence of SEQ ID NO: 19.

2. The influenza virus of claim 1, wherein the PB1 gene segment encodes a PB1 protein having the amino acid sequence of SEQ ID NO: 7, the PB2 gene segment encodes a PB2 protein having the amino acid sequence of SEQ ID NO: 15, the PA gene segment encodes a PA protein having the amino acid sequence of SEQ ID NO: 17, the NP gene segment encodes an NP protein having the amino acid sequence of SEQ ID NO: 6, and the NS gene segment encodes an NS1 protein having the amino acid sequence of SEQ ID NO: 19.

3. The influenza virus of claim 2, wherein the PB1 gene segment has the nucleotide sequence represented by SEQ ID NO: 2.

4. The influenza virus of claim 2, wherein the NP gene segment has the nucleotide sequence represented by SEQ ID NO: 1.

5. The influenza virus of claim 2, wherein the PB2 gene segment has the nucleotide sequence represented by SEQ ID NO: 14.

6. The influenza virus of claim 2, wherein (a) a leucine at position 40, a tryptophan at position 180, and an asparagine at position 464 in SEQ ID NO: 7 or (b) a leucine at position 116 and a lysine at position 294 in SEQ ID NO: 6 are conserved in after at least ten serial passages in a Vero cell line.

7. The influenza virus of claim 2, wherein (a) a leucine at position 40, a tryptophan at position 180, and an asparagine at position 464 in SEQ ID NO: 7 or (b) a leucine at position 116 and a lysine at position 294 in SEQ ID NO: 6 are conserved after at least ten serial passages in a Vero cell line that stably expresses the M2 ion channel protein of influenza A virus.

8. The influenza virus of claim 2, wherein the influenza virus is an influenza A virus, and (a) a leucine at position 40, a tryptophan at position 180, and an asparagine at position 464 in SEQ ID NO: 7 or (b) a leucine at position 116 and a lysine at position 294 in SEQ ID NO: 6 are conserved after at least ten serial passages in a Vero cell line that stably expresses the BM2 ion channel protein of influenza B virus.

9. The influenza virus of claim 1, wherein (b) the PB1 gene segment encodes a PB1 protein having the amino acid sequence of SEQ ID NO: 9, the PB2 gene segment encodes a PB2 protein having the amino acid sequence of SEQ ID NO: 10, the PA gene segment encodes a PA protein having the amino acid sequence of SEQ ID NO: 17, the NP gene segment encodes an NP protein having the amino acid sequence of SEQ ID NO: 8, and the NS gene segment encodes an NS1 protein having the amino acid sequence of SEQ ID NO: 19.

10. The influenza virus of claim 9, wherein the PB1 gene segment has the nucleotide sequence represented by SEQ ID NO: 4.

11. The influenza virus of claim 9, wherein the PB2 gene segment has the nucleotide sequence represented by SEQ ID NO: 5.

12. The influenza virus of claim 9, wherein the NP gene segment has the nucleotide sequence represented by SEQ ID NO: 3.

13. The influenza virus of claim 9, wherein (a) a leucine at position 40, a tryptophan at position 180, and a serine at position 607 in SEQ ID NO: 9, (b) a valine at position 504, an isoleucine at position 467, and a valine at position 529 in SEQ ID NO: 10, or (c) a leucine at position 116 and an arginine at position 311 in SEQ ID NO: 8 are conserved after at least ten serial passages of the virus in a Vero cell line.

14. The influenza virus of claim 9, wherein (a) a leucine at position 40, a tryptophan at position 180, and a serine at position 607 in SEQ ID NO: 9, (b) a valine at position 504, an isoleucine at position 467, and a valine at position 529 in SEQ ID NO: 10, or (c) a leucine at position 116 and an arginine at position 311 in SEQ ID NO: 8 are conserved after at least ten serial passages in a Vero cell line that stably expresses the M2 ion channel protein of influenza A virus.

15. The influenza virus of claim 1, wherein at least one of the PB1, PB2, and PA genes segments comprises a cytosine to uracil promoter mutation at nucleotide position 4.

16. The influenza virus of claim 1, wherein the influenza virus is a recombinant influenza virus.

17. The influenza virus of claim 1, wherein the virus further comprises an NA gene segment and an HA gene segment.

18. The influenza virus of claim 17, wherein the HA gene segment encodes an HA protein having the amino acid sequence comprising at least one amino acid mutation in HA1.

19. The influenza virus of claim 17, wherein the HA gene segment encodes an HA protein having the amino acid sequence comprising at least one amino acid mutation in HA2.

20. The influenza virus of claim 19, wherein the at least one amino acid mutation in HA2 is an asparagine at position 107.

21. The influenza virus of claim 17, wherein the PB1, PB2, PA, NP, and NS gene segments are from a single influenza strain.

22. The influenza virus of claim 21, wherein the HA gene segment is derived from an influenza strain different from the single influenza strain from which the PB1, PB2, PA, NP, and NS gene segments are from.

23. The influenza virus of claim 21, wherein the NA gene segment is derived from an influenza strain different from the single influenza strain from which the PB1, PB2, PA, NP, and NS gene segments are from.

24. The influenza virus of claim 1, further comprising a mutant M gene segment.

25. The influenza virus of claim 24, wherein the influenza virus does not encode a functional M2 protein.

26. The influenza virus of claim 1, wherein the virus is capable of replication in human cells.

27. The influenza virus of claim 1, wherein, if the influenza virus is the influenza virus of (a), the influenza virus has enhanced growth as compared to an influenza virus that is the same except without a leucine at position 40, a tryptophan at position 180, and an asparagine at position 464 in SEQ ID NO: 7 and a leucine at positions 116 and a lysine at position 294 in SEQ ID NO: 6 in Vero cells under the same conditions, and, if the influenza virus is the influenza virus of (b), the influenza virus has enhanced growth as compared to an influenza virus that is the same except without a leucine at position 40, a tryptophan at position 180, and a serine at position 607 in SEQ ID NO: 9, a valine at position 504, an isoleucine at position 467, and a valine at position 529 in SEQ ID NO: 10, and a leucine at position 116 and an arginine at position 311 in SEQ ID NO: 8 in Vero cells under the same conditions.

28. A pharmaceutical formulation comprising the influenza virus of claim 1.

29. The pharmaceutical formulation of claim 28, wherein the pharmaceutical formulation is a vaccine.

30. The pharmaceutical formulation of claim 29, wherein the vaccine is formulated as a monovalent vaccine, a bivalent vaccine, a trivalent vaccine, or a quadrivalent vaccine.

31. A method of eliciting an immune response in a mammal, the method comprising administering the influenza virus of claim 1 to the mammal, thereby eliciting an immune response to the influenza virus in the mammal.

32. The method of claim 31, wherein the mammal is a human.

33. A method of generating the influenza virus of claim 1, the method comprising serially passaging an influenza virus in a Vero cell line.

* * * * *